United States Patent [19]

Hsu et al.

[11] Patent Number: 5,563,230

[45] Date of Patent: Oct. 8, 1996

[54] CHIRAL SMECTIC LIQUID CRYSTALLINE POLYMERS

[75] Inventors: Chain-Shu Hsu; Jhy-Horung Lin; Li-Jen Shih; Ging-Ho Hsiue, all of Hsinchu, Taiwan

[73] Assignee: National Science Council, Taipei, Taiwan

[21] Appl. No.: 303,748

[22] Filed: Sep. 9, 1994

[51] Int. Cl.[6] .................. C08G 77/14; C09K 19/52; C09K 19/12
[52] U.S. Cl. .................. 528/25; 528/26; 528/31; 252/299.01; 252/299.65; 556/457
[58] Field of Search .................. 252/299.01, 299.65; 556/457; 528/25, 26, 31

[56] References Cited

U.S. PATENT DOCUMENTS

| | | | |
|---|---|---|---|
| 4,904,066 | 2/1990 | Gray et al. | 359/103 X |
| 5,138,010 | 8/1992 | Keller et al. | 528/26 |
| 5,252,695 | 10/1993 | Niciri et al. | 528/30 |
| 5,259,987 | 10/1993 | McArdle et al. | 252/299.01 |
| 5,332,251 | 7/1994 | Yuasa et al. | 252/299.01 |
| 5,350,538 | 9/1994 | Moriwaki et al. | 252/299.01 |
| 5,399,290 | 3/1995 | Haberle et al. | 252/299.01 |

FOREIGN PATENT DOCUMENTS 0293911 12/1988 Japan.
4040417 2/1992 Japan.

OTHER PUBLICATIONS

Suzuki et al., Makromol. Chem., RapidCommun, 9, 755–760, 1988.

Chen et al., Ferroelectrics, vol. 147, 1993, pp. 241–253.

"Synthesis and Characterization of Ferroelectric Liquid Crystalline Polysiloxanes and Polymethacrylates Containing [(S)–2–Methyl–1–butoxyphenyl 4–(Alkyloxy)biphenyl–4'–carboxylate Side Groups", Chain–Shu Hsu, et al., Macromolecules, vol. 25, No. 26, 1992, pp. 7126–7134.

"Synthesis of Liquid Crystalline Polysiloxanes and Polymethacrylates with Broad Temperature Ranges of the Chiral Smectic C Phase", Chain–Shu Hsu, et al., Macromolecules, vol. 26, No. 12, 1993, pp. 3161–3167.

Primary Examiner—C. H. Kelly
Attorney, Agent, or Firm—Hitt Chwang & Gaines, P.C.

[57] ABSTRACT

A chiral smectic liquid crystalline polymer having the following formula is disclosed:

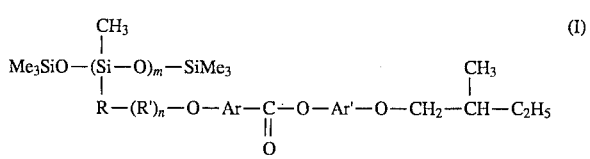

wherein m is an integer of about 40–80;

n is an integer of about 1–12;

R is ethylene or trimethylene;

R' is methylene or oxyethylene;

Ar is phenylene, chlorophenylene or

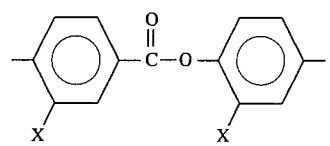

wherein x is chlorine or hydrogen; and

Ar' is phenylene or phenylenecarbonyl.

2 Claims, 55 Drawing Sheets

CHIRAL SMECTIC LIQUID CRYSTALLINE POLYMERS

FIELD OF THE INVENTION

The file of this patent contains at least one drawing executed in color. Copies of this patent with color drawings will be provided by the Patent and Trademark Office upon request and payment of the necessary fee.

The present invention is related to chiral smectic liquid crystalline polymers, in particular to side-chain chiral smectic liquid crystalline polymers.

BACKGROUND OF THE INVENTION

Recently, the synthesis of liquid crystalline polymers has attracted an increasing interest among various macromolecular compounds, because of their versatile applications, such as liquid crystal display (LCD) devices, optical filtering lens, reflection lens, linear optical polarizing lens (Displ. Technol., 1, 81 (1985)), and stationary phase materials used in high performance chromatography (J. Org. Chem., 49, 4947 (1984)). In addition, researchers have focused on their use as an optical memory material in the fabrication of erasable optical discs, for examples articles published in Mol. Cryst. Liq. Letters., 102, 78 (1984); Mol Cryst. Liq. Cryst., 102, 78(1984).

The potential applications of ferroelectric liquid crystals in fast-switching, high resolution electrooptical devices is well documented. [ Clark, N. A. and Lagerwall, S. T. appl. Phys. Lett. 1980, 36, 899; Lagerwall, S. T. and Dahl, I. Mol. Crys. Liq. Crys.. 1984, 114, 151; Lagerwall, S. T., et al. Mol. Cryst. 1987, 152, 503]

A number of ferroelectric liquid crystalline side-chain polymers have been prepared during the past few years. Among them there are liquid crystalline polymers having a backbone based on acrylates or acrylate derivatives [V. P. Shibaev, et al. Polymer Bulletin, 12, 299 (1984); J. C. Dubois, et al. Mol. Cryst. Liq. Cryst., 1986, Vol. 137, pp. 349–364;.S. Esselin, et al. Mol. Cryst. Liq. Cryst., 1988, Vol. 155, pp. 371–387; S. Bualek, et al. Mol. Cryst. Liq Cryst., 1988, Vol. 155, pp. 47–56; S. Uchida, et al. Mol. Cryst. Liq. Cryst., 1988, Vol. 155, pp. 93–102; K. Shiraishi et al., Makromol. Chem., 190, 2235–2243 (1989); V. Percec, et al. Journal of Polymer Science: Part A: Polymer Chemistry, Vol. 27, 2367–2384 (1989); S. Esselin, et al. Liquid Crystal, 1987, Vol. 2, No. 4, 505–518; B. Messner, et al. Makromol. Chem. 192, 2383–2390 (1991); E. C. Bolton, et al. Liquid Crystal, 1992, Vol. 12, No. 2, 305–318; J. Bomelburg, et al. Makromol. Chem., Rapid Commun. 12, 483–488 (1991); G. Scherowsky, et al. Liquid Crystal, 1991, Vol. 10, No. 6, 809–819], liquid crystalline polymers having a backbone of polylaurates [J. M. Guglieminetti, et al. Polymer Bulletin 16, 411–418 (1986)], liquid crystalline polymers having a backbone based on diazo-compounds or derivatives thereof [R. Zentel, et al. Liq. Cryst., 1987, 2(1), 83–89; S. Bualek, et al. Makromol. Chem., 189, 797–804(1988); H. Kapitza, et al. Makromol. Chem., 189, 1793–1807 (1988); R. Zentel Makromol. Chem., 190, 2869–2884 (1989); H. Kapitza, et al. Makromol. Chem., 192, 1859–1872 (1991 ); S. U. Vallerien, et al. Makromol. Chem., Rapid Commun., 10, 333–338 (1989)], liquid crystalline polymers having a backbone of polytartrates [S. Ujiie, et al. Polymer Journal, Vol. 23, No. 12, pp. 1483–1488 (1991)], and liquid crystalline polymers having a backbone of polysuccinates [K. Fujishiro, et al. Liquid Crystals, 1992, Vol. 12, No. 4, 561–573]. The above-mentioned liquid crystalline polymers do not have a segment of polysiloxane in the backbones thereof.

B. Hahn, et al. in their articles, Mol, Cryst. Liq. Cryst. Inc. Nonlin. Opt., 1988, Vol. 157, pp. 125–150; and Macromolecules, Vol. 20, No. 12, 1987, disclose liquid crystalline polymers having a backbone of polysiloxane. The mesogenic groups of these liquid crystalline polysiloxanes contain 1,3-dioxanyl. C. Destrade, et al. in their article, Liquid Crystals, 1991, Vol. 10, No. 4, pp. 457–493, disclose liquid crystalline polysiloxanes containing α-chloroalkyl carboxylic acid or aromatic ester of alkyl carboxylic acid mesogenic groups. The present invention is directed to liquid crystalline polysiloxanes containing mesogenic groups of alkoxy aromatic ester or alkoxy carbonyl aromatic ester of aromatic carboxylic acid.

An object of the present invention is to provide novel liquid crystalline polymers.

Another object of the present invention is to provide liquid crystalline polysiloxanes.

Still another object of the present invention is to provide mesogenic monomers for synthesizing liquid crystalline polymers.

SUMMARY OF THE INVENTION

A liquid crystalline polysiloxane having the following formula (I) is disclosed:

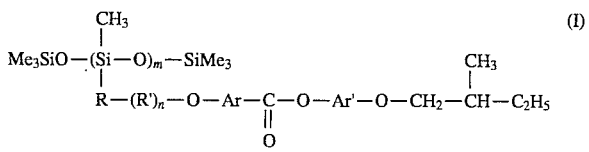

wherein Me is methyl;

m represents the degree of polymerization of polymer backbone and is an integer of about 40–80;

n represents the spacer between the backbone and the side chain mesogenic groups and is an integer of about 1–12;

R is ethylene or trimethylene;

R' is methylene or oxyethylene;

Ar is phenylene, substituted phenylene or

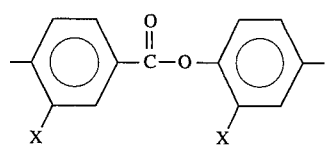

wherein x is chlorine or hydrogen;

Ar' is phenylene or phenylenecarbonyl.

Preferably, Ar is para-phenylene and substituted para-phenylene, wherein the substituent is preferably chlorine.

Preferably, Ar' is para-phenylenecarbonyl.

DETAILED DESCRIPTION OF THE INVENTION

Figure 1:
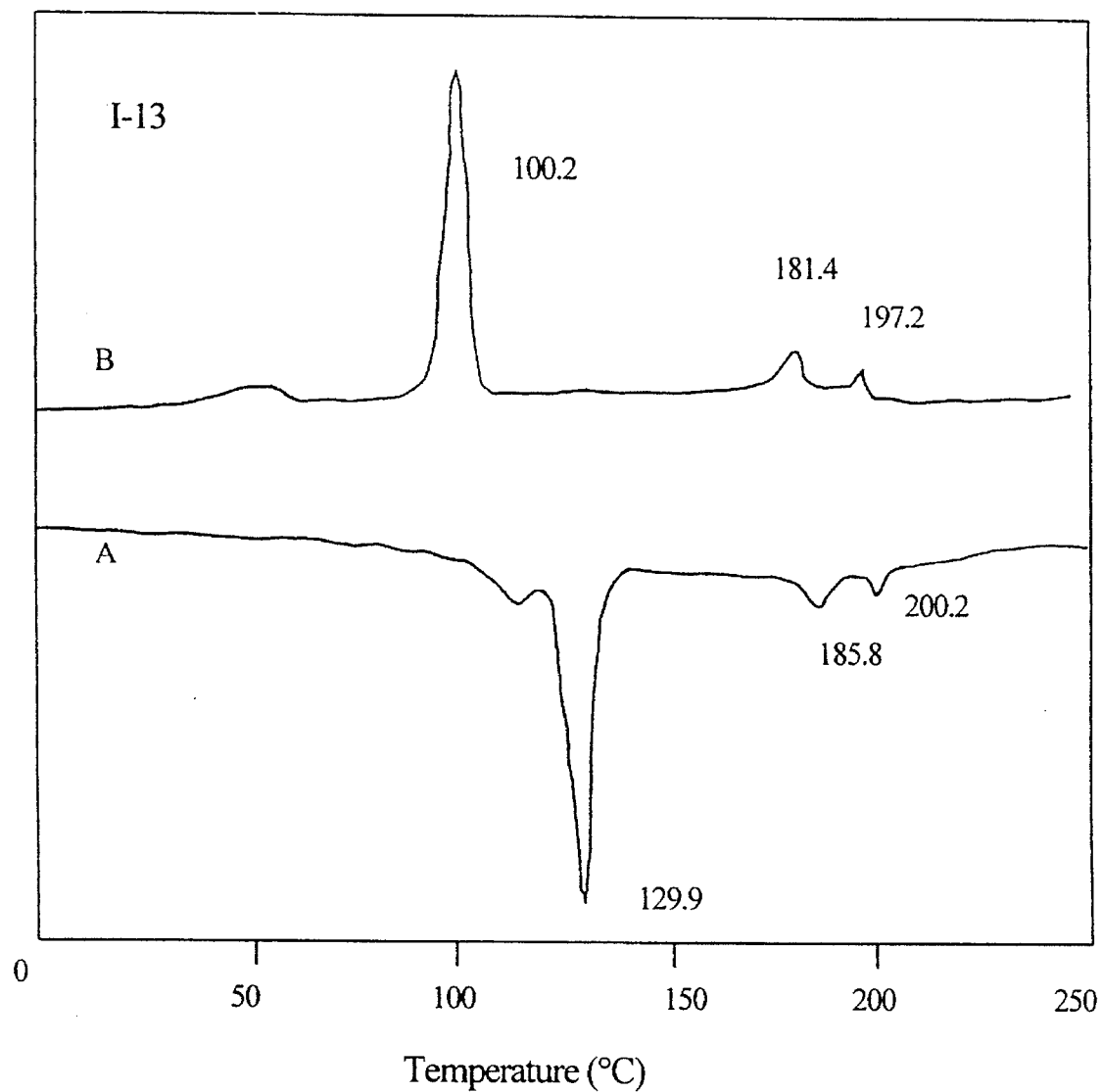
FIG. 1 is a Differential Scanning Calorimeter (DSC) thermogram (10° C./min) for monomer I-13: A) heating scan; B) cooling scan.

A suitable method of synthesizing the liquid crystalline polymer of the above formula (I) comprises graft polymerizing the following monomer (IIA):

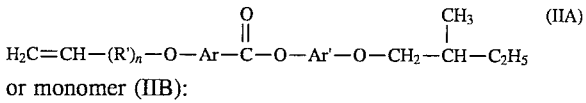

or monomer (IIB):

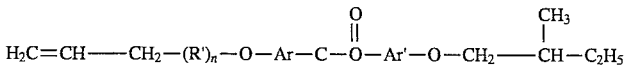

wherein R', Ar and Ar' are defined same as in the formula (I), onto a polymer backbone having the following formula (III) in a suitable solvent and under suitable reacting conditions:

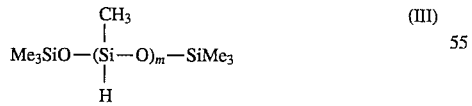

wherein Me and m are defined same as in the formula (I).

Said suitable solvent includes any organic solvent which renders the compounds of the above formulas (I), (IIA) (IIB) and (III) soluble or dispersible therein, and does not reacted with the compounds of the above formulas (I), (IIA), (IIB) or (III), such as aromatic solvent: benzene, toluene, dimethylbenzene, and the like. The organic solvent is preferably dehydrated to an anhydrous form before use.

Said suitable reacting conditions mainly includes a suitable catalyst and a suitable reacting temperature under which the graft polymerization of the compounds (IIA) or (IIB) and (III) can be carried out. Said suitable catalyst can be any catalyst which catalyzes the graft polymerization of polymethylhydrosiloxane and monomer having vinyl group, such as platinum-divinyltetramethyldisiloxane complex. Said suitable reacting temperature means a temperature which is not higher than the boiling point of said suitable solvent, preferably ranging from about 60° C. to about 150° C., and most preferably ranging from 80° C. to 110° C. A refluxing apparatus is preferably adopted when the graft polymerization undergoes at the boiling temperature of said organic solvent.

The polymer backbone of formula (III) can be prepared by any known methods disclosed in the art or purchased directly from the market, namely Petrarch Systems Inc., Bristal, Pa., U.S.A.

The mesogenic monomers of formulas (IIA) and (IIB) can be synthesized according to, but not limited to, the methods disclosed in the following Preparation Examples.

In the following examples, the organic solvents used are preferably in anhydrous form. Anhydrous ethyl ether was prepared by drying over sodium particles and distilling under nitrogen with refluxing, wherein dibenzyl ketone was used as an indicator. Toluene, benzene and ethanol were dried over sodium metal. Anhydrous dichloromethane was prepared by drying over calcium chloride, refluxing under nitrogen for several hours, and then distillation. The organic solvents were dehydrated immediately before use or the dehydrated organic solvents were sealed in containers which were then stored in a drier.

The following apparatuses were used in the analysis and identification of the characteristics of the intermediates and liquid crystalline polysiloxanes synthesized in the following examples:

1. FT-IR spectrum: Nicolet 520 FT-IR spectrometer was used; a liquid specimen was contained between two KBr tablets and measured; and the unit is $cm^{-1}$.

2. NMR spectrum: Bruker AM 400 MHz NMR was used. d-Chloroform was used as solvent; the chemical shift unit is ppm; the unit of coupling constant is Hz; and $\delta=0.00$ ppm of tetramethylsilane was used as an internal standard. s represents singlet; d represents doublet; t represents triplet; q represents quarlet; and m represent multiplier.

3. Differential Scanning Calorimeter (DSC): Dupont, type 910 DSC equipped with a mechanical cooling accessory and type 2100 Computer/Thermal Analyzer were used. The temperature calibration was carried out by using 5–10 mg In both heating and cooling curves. The heating and cooling rates were 10° C./min. The phase transition temperatures and the thermodynamic function values ($\Delta H$ and $\Delta S$) of the specimens were collected by taking the maximum or minimum values. The glass transition temperatures (Tg's) of polymer specimens were taken at the point of maximum inflection.

4. Optical Polarizing Microscope: Nikon, Microphot-FX optical microscope (40×–800×) was used. Heating and cooling rates were controlled at 10° C./min by using a Mettler FP 82 hot stage and a FP 80 central processor.

5. Digital Polarimeter: JASCO MODEL DIP-140 polarimeter equipped with a sodium lamp was used. The length of the specimen groove is 100 cm; 1% dextrose having $[\alpha]_D^{25}=+52.5~+53$ was used as a calibration standard; and all the specimens were tested at room temperature.

6. Flash Chromatography: EYELA type EF-10 Flash Chromatograph was used. The column used was filled with silicone gel beads of mesh No. 230–240 supplied by Merck Co. This apparatus was used when a purification of a specimen by column chromatography was required.

7. Element Analyzer: Heraeus CHN-O-RAPID apparatus was used.

8. Gel Permeation Chromatography (GPC): 400 Solvent Delivery System (manufactured by Applied Biosystems Inc.) equipped with a Viscotek differential refractometer/viscometer was used. A GPC column, code Ultrastyragel, supplied by American Polymer Standards Corporation was used. The concentration of the specimen was 5.0 mg/ml; polystyrene was used as a standard; tetrafuran (THF) was used as the eluent; and the flow rate of the eluent was 1.0 ml/min.

The present invention will be further understood from the following Preparation Examples 1–37 and Examples 1–12, which are used to illustrate and not to limit the scope of the present invention.

PREPARATION EXAMPLE 1

Synthesis of (S)-(–)-2-Methyl-1-butyl tosylate (I-1)

In a three necks flask 17 ml pyridine was charged, and stirred under nitrogen and at a temperature which was maintained at 10° C. and 4.67 g (0.053 mole) (S)-(–)-2-methylbutanol was added to the stirred liquid, and then 11.2 g (0.054 mole) p-tolysufonyl chloride was added slowly such that the temperature of the stirred mixture was not higher than 20° C. The stirring was maintained for 10 hours at room temperature, 250 ml ice water was added to the stirred mixture and then extracted with ethyl ether. The ethyl ether layer was collected, washed with 50% HCl aqueous solution, dried over anhydrous $MgSO_4$, filtered and then distilled at 33 mmHg, 142°–150° C. to yield 10.88 g colorless liquid. Yield: 84.7%. The optical rotation, $[\alpha]_D^{25}$= +4.605. $^1$H-NMR: 0.97–0.85 (m;6H,—C—C$\underline{H}_3$) 2.49 (s;3H,C$\underline{H}_3$—Ph—) 0 1.47–1.15 (m;2H,—C$\underline{H}_2$—CH$_3$) 3.95–3.84 (m;2H,C$\underline{H}_2$—O—) 1.79–1.71 (m;1H,—C—C $\underline{H}$CH$_3$—C—) 7.84–7.39 (m;4H,aromatic protons)

PREPARATION EXAMPLE 2

Synthesis of 4-(S)-(–)-2-Methyl-1-butoxyphenyl benzyl ether (I-2)

7.84 g (0.0374 mole) of hydroquinone monobenzylether and 150 ml of 95% ethanol were mixed and heated to boil, 2.1 g (0.0375 mole) of KOH and 0.5 g of KI were added to the boiled mixture, and then (S)-(–)-2-Methyl-butanyl tosylate was added dropwise. The mixture was heated to reflux for 3 hours; cooled to room temperature; diluted with ethyl ether; washed with water, 10% NaOH aqueous solution and diluted HCl in sequence; and the ethyl ether layer was collected, dried over anhydrous $MgSO_4$, filtered and concentrated. The concentrated ethyl ether layer was recrystallized from methanol to yield 7.491 g of gray solid; mp=33.6° C.; yield: 89%. $^1$H-NMR: 1.00–0.90 (m;6H,—C—C$\underline{H}_3$) 5.00 (s;3H,C$\underline{H}_3$—Ph—) 1.63–1.18 (m;2H,—C$\underline{H}_2$—CH$_3$) 6.91–6.81 (m;4H,—O—P$\underline{h}$—O—) 1.85–1.78 (m;1H,— C—C$\underline{H}$CH$_3$—C—) 7.42–7.24 (m;5H,—CH$_2$—P$\underline{h}$) 3.77–3.64 (m;2H,—O—C$\underline{H}_2$—C—)

PREPARATION EXAMPLE 3

Synthesis of 4-((S)-(–)-2-Methyl-1-butoxy) phenol (I-3)

In a two necks flask 1.73 g (0.0064 mole) of compound I-2, 50 ml of ethyl acetate and 0.321 g of 10% Pd/C were charged. Hydrogen was introduced into the flask after it was vacuumed. The reaction was stopped when hydrogen consumption ceased. The reaction mixture was filtered, concentrated, and purified by column chromatography (ethyl acetate/n-hexane=1/3) to yield 0.79 g of light yellow solid; mp.=45.6° C.; yield: 68.5%; the optical rotation, $[\alpha]_D^{25}$=– 8.44. $^1$H-NMR: 0.98–0.89 (m;6H,—C—C$\underline{H}_3$) 3.75–3.62 (m;2H,—O—C$\underline{H}_2$—) 1.56–1.18 (m;2H,—C$\underline{H}_2$—CH$_3$) 3.95–3.84 (s;1H,—O$\underline{H}$) 1.82–1.78 (m;1H,—C—C $\underline{H}$CH$_3$—C—) 7.84–7.39 (m;4H, aromatic H)

PREPARATION EXAMPLES 4–6

Synthesis of 4-Bromo-1-butene (I-4)
5-Bromo-1-pentene (I-5) 6-Bromo-1-hexene (I-6)

Compounds I-4–I-6 were prepared by removing HBr from 1,4-dibromobutane; 1,5-dibromopentane and 1,6-dibromohexane, respectively. The synthesis of compound I-6 is described below as an example. 100 ml 1,6-dibromohexane was charged to an 250 ml two necks flask, wherein one neck thereof was equipped with an feeding funnel of 50 ml hexamethyl-phosphorous triamide and the other neck thereof was equipped with a distillation apparatus having an acetone/Dry Ice cold trap. The 1,6-dibromohexane was heated to 195° C. and then hexamethylphosphorous triamide was added with a rate of one drop per second. The reaction product was collected in the cold trap during the addition due to its low boiling point. The temperature was raised to 220° C. as soon as the addition of hexamethyl-phosphorous triamide was completed. The product collected in the cold trap was further subjected to two distillation to yield colorless liquid. The yield of compounds I-4, I-5 and I-6 are 65%, 61.5% and 50.3%, respectively. $^1$H-NMR:
I-4 2.65–2.58 (q;2H,—C$\underline{H}_2$—CH=) 5.16–5.10 (1;2H,— CH=C$\underline{H}_2$) 3.43–3.38 (t;2H,—C$\underline{H}_2$—Br) 5.85–5.73 (m;1H, —C$\underline{H}$=CH$_2$)
I-5 1.96–1.87 (m;2H,—CH$_2$—C$\underline{H}_2$—CH$_2$—) 5.10–4.98 (q;2H,—CH=C$\underline{H}_2$) 2.21–2.15 (q;2H,—C$\underline{H}_2$—CH=) 5.79–5.70 (m;1H,—C$\underline{H}$=CH$_2$) 3.40–3.36 (t;2H,—C $\underline{H}_2$—Br)
I-6 1.89–1.46 (m;4H,—CH$_2$—C$\underline{H}_2$—CH$_2$—) 5.02–4.93 (q;2H,—CH=C$\underline{H}_2$) 2.09–2.02 (q;2H,—C$\underline{H}_2$—CH=) 5.81–5.70 (m;1H,—C$\underline{H}$=CH$_2$) 3.41–3.36 (t;2H,—C $\underline{H}_2$—Br)

PREPARATION EXAMPLE 7

Synthesis of 10-Undecen-1-yl tosylate (I-7)

Nitrogen was introduced into a three necks flask containing 50 ml anhydrous pyridine which was stirred at 10° C. 17 g (0.1 mole) 10-undecen-1-ol was added to the stirred pyridine, and then p-tolysufonyl chloride was added slowly such that the temperature of the stirred mixture was not high than 20° C. The stirring was maintained for 10 hours at room temperature, 250 ml ice water was added to the stirred mixture and then extracted with ethyl ether. The ethyl ether layer was collected, washed with 50% HCl aqueous solution, dried over anhydrous $MgSO_4$, filtered and then concentrated to yield 26.81 g colorless liquid. Yield: 79.6%.

$^1$H-NMR: 1.65–1.11 (m;14H,—CH$_2$—CH$_2$—) 5.05–4.93 (q;2H,—CH=C$\underline{H}_2$) 2.10–2.04 (q;2H,—C$\underline{H}_2$—CH=) 5.88–5.79 (m;1H,—C$\underline{H}$=CH$_2$) 2.49 (s;3H,—Ph—CH$_3$) 7.86–7.49 (q;4H, aromatic H)

PREPARATION EXAMPLES 8–12

Synthesis of

4-Allyloxybiphenyl-4'-carboxylic acid (I-8)
4-(3-Buten-1-yloxy)biphenyl-4'-carboxylic acid (I-9)
4-(4-Penten-1-yloxy)biphenyl-4'-carboxylic acid (I-10)
4-(5-Hexen-1-yloxy)biphenyl-4'-carboxylic acid (I-11)
4-(10-Undecen-1-yloxy)biphenyl-4'-carboxylic acid (I-12)

All the five compounds were prepared by the same method. The compounds I-8, I-9, I-10, I-11 and I-12 were synthesized by separately reacting allyl iodide, compounds I-4, I-5, I-6 and I-7 with 4-hydroxybiphenyl-4'-carboxylic acid. The synthesis of compound I-12 was described below as an example. 3.62 g (0.0157 mole) 4-hydroxylbiphenyl-4'-carboxylic acid, 500 ml ethanol, 50 ml water, 0.5 g KI and 2.02 g (0.036 mole) NaOH were heated to reflux for one hour. 7 g compound I-7 was then added dropwise. The mixture was refluxed for 12 hours and then 100 ml of 10% NaOH aqueous solution was added. The mixture was again heated to reflux for 2 hours, and cooled to room temperature. Water and diluted HCl were poured into the cooled mixture to precipitate, and the precipitated white solid was filtered and recrystallized from acetic acid to obtain 4.43 g of white crystals. mp: I-8: 231.8° C.; I-9: 223.7° C.; I-10: 213.9° C.; I-11: 202.8° C.; I-12: 161.4° C. Yield: I-8: 66.9%;I-9: 84.03%; I-10: 81.4%; I-11: 89.96%; I-12: 80.6%. $^1$H-NMR: I-8 4.65–4.63 (q;2H,—O—C$\underline{H}_2$—C=) 6.12–6.07 (m;1H, —C$\underline{H}$=CH$_2$) 5.46–5.25 (q;2H,—CH=C$\underline{H}_2$) 8.09–7.04 (m;8H,aromatic H)

I-9 2.58–2.52 (q;2H,—C$\underline{H}_2$—CH=) 6.00–5.90 (m;1H,—C$\underline{H}$=CH$_2$) 4.13–4.10 (t;2H,—O—C$\underline{H}_2$—CH$_2$—) 8.09–7.04 (m;8H, aromatic H) 5.21–5.07 (q;2H,—CH=C$\underline{H}_2$)

I-10 1.84–1.79 (m;2H,—C$\underline{H}_2$—CH$_2$—) 4.91–4.89 (q;2H, —CH=C$\underline{H}_2$) 2.18–2.13 (q;2H,—C$\underline{H}_2$—CH=) 5.89–5.80 (m;1H,—C$\underline{H}$=CH$_2$) 4.04–3.86 (t;2H,—O—C$\underline{H}_2$—CH$_2$—) 8.09–7.08 (m;8H aromatic H)

I-11 1.85–1.56 (m;4H,—C$\underline{H}_2$—CH$_2$—) 5.06–4.94 (q;2H,—CH=C$\underline{H}_2$) 2.17–2.12 (q;2H,—C$\underline{H}_2$—CH=) 5.89–5.82 (m;1H,—C$\underline{H}$=CH$_2$) 4.09–4.06 (t;2H,—O—C$\underline{H}_2$—CH$_2$) 8.09–7.04 (m;8H aromatic H)

I-12 1.89–1.27 (m;14H,—C$\underline{H}_2$—CH$_2$—) 5.00–4.89 (q;2H, —CH=C$\underline{H}_2$) 2.21–2.18 (q;2H,—C$\underline{H}_2$—CH=) 5.84–5.77 (m;1H,—C$\underline{H}$=CH$_2$) 4.08–4.04 (t;2H,—O—C$\underline{H}_2$—CH$_2$) 8.09–7.04 (m;8H, aromatic H)

PREPARATION EXAMPLES 13–17

Synthesis of 4-((S)-2-Methyl-1-butoxy)phenyl 4-allyloxybiphenyl-4'-carboxylate (I-13)
4-((S)-2-Methyl-1-butoxy)phenyl 4-(3-buten-1-yloxy)biphenyl-4'-carboxylate (I-14)
4-((S)-2-Methyl-1-butoxy)phenyl 4-(4-penten-1-yloxy)biphenyl-4'-carboxylate (I-15)
4-((S)-2-Methyl-1-butoxy)phenyl 4-(5-hexen-1-yloxy)biphenyl-4'-carboxylate (I-16)
4-((S)-2-Methyl-butoxy)phenyl 4-(10-undecen-1-yloxy)biphenyl-4'-carboxylate (I-17)

All the five compounds were prepared by the same method, which involves converting an carboxylic acid group to acyl chloride group and reacting with the hydroxyl group of compound I-3. The synthesis of compound I-13 was described below as an example. Part (A): 1.524 g (0.006 mole) compound I-8, one drop of dimethylformamide and 4 ml thionylchloride were mixed and stirred at room temperature to obtain a transparent solution. Part (B): 1.08 g (0.006 mole) compound I-3, 1.67 ml triethylamine and a small amount of anhydrous dichloromethane were mixed and stirred in an ice water bath of 0°–5° C. Part (A) solution was poured into part (B) and stirred at room temperature for two hours, and the residual triethylamine and dichloromethane were distilled off. The resulting product was dissolved in 50 ml dichloromethane and purified with column chromatography (silica gel 70–230 mesh, 150 ml dichloromethane as eluent). The resulting product was concentrated and recrystallized from methanol to yield pure product. Elemental analysis: compound I-13: C: 76.90%, H: 6.86%, O:14.68%; compound I-14: C:77.56%, H:6.99%, O:14.59%; compound I-15: C:77.78%, H:7.29%, O:13.77%; compound I-16: C:78.45%, H:7.45%, O:13.89%; compound I-17: C:79.46%, H:8.35%, O:12.07%. The optical rotation and $^1$H-NMR are listed in Table 1.

TABLE 1

Characterization of Monomers I-13 to I-17

| Monomer | Yield % | $[\alpha]^{25}_D$ | 400 MHz $^1$H-NMR (CDCl$_3$, δ, ppm) |
|---|---|---|---|
| I-13 | 77 | +4.087 | 0.88 (t, 3H, —CH$_2$-CH$_3$), 0.96 [(d, 3H, —CH(CH$_3$)-], 1.21–1.52 (m, 2H, —CH$_2$-CH$_3$), 1.86 [m, 1 H, —CH(CH$_3$)-], 3.72 [m, 2H, —OCH$_2$-CH(CH$_3$)-], 4.54 (d, 2H, —CH$_2$-OPh), 5.03 (m, 2H. CH$_2$=), 5,80 (m, 1 H, =CH—), 6.86–8.17 (m, 12H aromatic protons) |
| I-14 | 74 | +4.553 | 0.88 (t. 3H, —CH$_2$-CH$_3$), 0.96 [t, 3H, —CH(CH$_3$)-], 1.19–1.53 (m, 2H, —CH$_2$-CH$_3$), 1.80 [m, 1H, —CH(CH$_3$)-], 2.52 (m, 2H, —CH$_2$-CH=), 3.73[m, 2H, —OCH$_2$-CH(CH$_3$)-], 4.01 (t, 2H, —CH$_2$-OPh), 5.10 (m, 2H, CH@m), 5.88 (m, 1H, =CH—), 6.86–8.17 (m, 12H aromatic protons) |
| I-15 | 75 | +4.470 | 0.88 (t, 3H, —CH$_2$—CH$_3$), 0.96 [t, 3H, —CH(CH-3)- ], 1.17-1.89 [m, 5H, —CH$_2$- and —CH(CH$_3$)—CH$_2$-], 2.20 (m, 2H, —CH$_2$-CH=), 3.72 [m, 2H, —OCH$_2$-CH(CH$_3$)-], 3.97 (t, 2H, —CH$_2$-OPh) , 4.99 (m, 2H, CH$_2$=), 5.81 (m, 1H, =CH-), 6.86–8.17 (m, 12H aromatic protons) |
| I-16 | 71 | +4.967 | 0.88 (t, 3H, —CH$_2$—CH$_3$), 0.95 [(d, 3H, —CH(CH$_3$)-], 1.14–1.81 [m, 7H, -(CH$_2$)$_2$- and —CH(CH$_3$)-CH$_2$-], 2.07 (m, 2H, —CH$_2$-CH=), 3.72 [m, 2H, —OCH$_2$—CH(CH$_3$)-], 3.81 (t, 2H, —CH$_2$-OPh) , 5.10 (m, 2H, CH$_2$=), 5.86 (m, |

TABLE 1-continued

Characterization of Monomers I-13 to I-17

| Monomer | Yield % | $[\alpha]^{25}_D$ | 400 MHz $^1$H-NMR (CDCl$_3$, δ, ppm) |
|---|---|---|---|
| I-17 | 43 | +4.220 | 1H, =CH—), 6.86–8.16 (m, 12H aromatic protons) 0.86 (t, 3H, —CH$_2$—CH$_3$), 0.94 [(d, 3H, —CH(CH$_3$)-], 1.18–1.80 [m, 17H, -(CH$_2$)$_7$- and —CH(CH$_3$)—CH$_2$-], 2.03 (m, 2H, —CH$_2$-CH=), 3.91 [m, 2H, -OCH$_2$-CH(CH$_3$)-], 4.11 (m, 2H, —CH$_2$-OPh) , 4.90 (m, 2H, CH$_2$=), 5.76 (m, 1H, =CH—), 6.90–8.14 (m, 12H aromatic protons) |

PREPARATION EXAMPLES 18–19

Synthesis of 4-(10-Undecen-1-yloxy) benzoic acid (I-18);
3-Chloro-4-(10-undecen-1-yloxy) benzoic acid (I-19)

10-Undecen-1-yl Tosylate (compound I-7) was separately reacted with 4-hydroxybenzoic acid and 3-chloro-4-hydroxy-benzoic acid to synthesize the compounds I-18 and I-19. The synthesis of compound I-18 was described below as an example. 1.75 g (0.0312 mole) KOH, 0.05 g KI and 100 ml of 90% ethanol were mixed and refluxed. To the mixture 2.15 g (0.0156 mole) 4-hydroxybenzoic acid was added dropwise, and refluxed for one hour. 4.433 g (0.013 mole) compound I-7 was added slowly and refluxed for 10 hours. 10% KOH was then added and refluxed again for two hours. Ethanol was removed from the mixture which was then extracted with ethyl ether. The collected ethyl ether layer was dried over anhydrous MgSO$_4$, filtered and concentrated to obtained solid product. The resulting solid product was recrystallized from ethanol. Yield: I-18: 40.6%; I-19: 36.4%. $^1$H-NMR:

I-18 1.74–1.26 (m;14H,—CH$_2$—CH$_2$—CH$_2$—) 5.81–5.74 (m;1H,H$_2$C=CH—) 2.01–1.96 (q;2H,ΔCH$_2$—CH=) 7.78–6.97 (q;4H,aromatic H) 4.03–3.99 (t;2H,—O—CH$_2$—CH$_2$—) 5.00–4.90 (q;2H,H$_2$C=CH—) 12.6 (s;1H,—COOH)

I-19 1.76–1.14 (m;14H,—CH$_2$—CH$_2$—CH$_2$—) 5.81–5.74 (m;1H,—H$_2$C=CH—) 2.01–1.96 (q;2H,—CH$_2$—CH=) 7.89–7.21 (m;3H, aromatic H) 4.13–4.11 (t;2H,—O—CH$_2$—CH$_2$—) 5.00–4.90 (q;2H,—H$_2$C=CH—) 12.9 (s;1H, —COOH)

PREPARATION EXAMPLES 20–21

Synthesis of 4-((S)-2-Methyl-1-butyloxy)phenyl) 4-hydroxy-benzoate (I-20):
4'-(4((S)-2-Methyl-butyloxy)phenyl) 3-chloro-4-hydroxy-benzoate (I-21)

4-((S)-2-methyl-1-butoxy)phenol (compound I-3) was separately reacted with 4-hydroxybenzoic acid and 3-chloro-4-hydroxy-benzoic acid to synthesize the compounds I-20 and I-21. The synthesis of compound I- 20 was described below as an example. In a 10 ml flask equipped with a Dean-Stark trap 1.38 g (0.01 mole) 4-hydroxybenzoic acid, 4.5 g (0.025 mole) compound I-3, 0.05 ml concentrated sulfuric acid and 2 ml anhydrous benzene were charged and refluxed for about two days until all the 4-hydroxybenzoic acid was dissolved. The mixture was cooled to room temperature and extracted with ethyl ether/2% sodium hydrogen carbonate aqueous solution. The ethyl ether layer was collected, dried, and concentrated to obtain solid product. The resulting solid product was recrystallized from ethanol. Yield: I-20: 90.13%; I-21: 91.2. $^1$H-NMR:

I-20 1.84–0.88 (m;9H,—CH$_2$—,—CH—5.82 (s;1H,—OH) and two—CH$_3$) 8.09–6.87 (m;8H, aromatic H) 3.82–3.69 (m;2H,—O—CH$_2$—)

I-21 1.83–0.87 (m;9H,—CH$_2$—,—CH— 6.08 (s;1H,—OH) and two-CH$_3$) 8.14–6.85 (m;7H, aromatic H) 3.78–3.65 (m;2H,—O—CH$_2$—)

PREPARATION EXAMPLES 22–25

Synthesis of

4-[4-((S)-2-methyl-1-butoxy)phenyloxycarbonyl]phenyl 4-(10-undecen-1-yloxy)benzoate (I-22)
2-Chloro-4-[4-((S)-2-methyl-1-butoxy)phenyloxycarbonyl] phenyl 4-(10-undecen-1-yloxy)benzoate (I-23)
4-[4-((S)-2-methyl-1-butoxy)phenyloxycarbonyl]phenyl 3-chloro-4-(10-undecen-1-yloxy)benzoate (I-24)
2-Chloro-4-[4-((S)-2-methyl-1-butoxy)phenyloxycarbonyl] phenyl 3-chloro-4-(10-undecen-1-yloxy)benzoate (I-25)

The four compounds were synthesized by converting compounds I-18 and I-19 to the corresponding acid chlorides, and then reacting separately with compounds I-20 or I-21 in triethylamine and anhydrous dichloromethane. The synthesis method and the monomers used in this example are similar to those of compounds I-13~I-17. Yield: I-22: 81.6%; I-23: 97.4%; I-24: 88.4%; I-25: 89.1%. $^1$H-NMR is listed in Table 2.

TABLE 2

Characterization of Monomers I-22–I-25

| Monomer | 400 MHz $^1$H-NMR (CDCl$_3$, δ, ppm) |
|---|---|
| I-22 | 1.99–0.76 (m, 25H, —CH$_2$-CH$_2$-CH$_2$, —CH— and —CH$_3$), 3.76–3.68 (m; 2H, —O—CH$_2$-CHCH$_3$-), 4.00–3.97 (t, 2H, —O-CH$_2$-CH$_2$-) 4.96–4.86 [q, 2H, H$_2$C=CH—), 5.82–5.73 (m, 1H, H$_2$C=CH—), 8.21–6.86 (m, 12H aromatic protons) |
| I-23 | 2.00–0.76 (m; 25H, —CH$_2$-CH$_2$CH$_2$, —CH— and —CH$_3$), 3.78–3.67 (m; 2H, —O—CH$_2$-CHCH$_3$-), 4.01–3.97 (t, 2H, —O—CH$_2$-CH$_2$-) 4.96–4.86 [q, 2H, H$_2$C=CH—), |

TABLE 2-continued

Characterization of Monomers I-22–I-25

| Monomer | 400 MHz $^1$H-NMR (CDCl$_3$, δ, ppm) |
|---|---|
| I-24 | 5.82–5.68 (m, 1H, H$_2$C=CH—), 8.28–6.86 (m, 11H aromatic protons) 2.01–0.76 (m; 25H, —CH$_2$-CH$_2$-CH$_2$, —CH— and —CH$_3$), 3.78–3.66 (m; 2H, —O—CH$_2$-CHCH$_3$-), 4.08–4.05 (t, 2H, —O—CH$_2$-CH$_2$-) 4.95–4.86 [q, 2H, H$_2$C=CH—), 5.82–5,69 (m, 1H, H$_2$C=CH—), 8.21–6.86 (m, 11H aromatic protons) |
| I-25 | 1.99–0.73 (m; 25H, —CH$_2$-CH$_2$-CH$_2$, —CH— and —CH$_3$), 3.78–3.65 (m; 2H, —O—CH$_2$-CHCH$_3$-), 4.08–4.05 (t, 2H, —O—CH$_2$-CH$_2$-) 4.96–4.86 [q, 2H, H$_2$C=CH—), 5.81–5.69 (m, 1H, H$_2$C=CH—), 8.28–6.85 (m, 10H aromatic protons) |

EXAMPLES 1–9: (P-1~P-9)

Poly[methyl[4-((S)-2-methyl-1-butoxy)phenyl 4-allyloxy biphenyl-4'-carboxylate]siloxane] (P-1)

Poly[methyl[4-((S)-2-methyl-1-butoxy)phenyl 4-(3-buten-1-yloxy)biphenyl-4'-carboxylate]siloxane] (P-2)

Poly[methyl[4-((S)-2-methyl-1-butoxy)phenyl 4-(4-penten-1-yloxy)biphenyl-4'-carboxylate]siloxane] (P-3)

Poly[methyl[4-((S)-2-methyl-1-butoxy)phenyl 4-(5-hexen-1-yloxy)biphenyl-4'-carboxylate]siloxane] (P-4)

Poly[methyl[4-((S)-2-methyl-1-butoxy)phenyl 4-(10-undecen-1-yloxy)biphenyl-4'-carboxylate]siloxane] (P-5)

Poly[methyl[4-[4-((S)-2-methyl-1-butoxy)phenyloxy carbonyl]phenyl 4-(10-undecen-1-yloxy)benzoate]siloxane] (P-6)

Poly[methyl[2-chloro-4-[4-((S)-2-methyl-1-butoxy)phenyloxy carbonyl]phenyl 4-(10-undecen-1-yloxy)benzoate]siloxane] (P-7)

Poly[methyl[4-[4-((S)-2-methyl-1-butoxy)phenyloxy carbonyl]phenyl 4-(10-undecen-1-yloxy)benzoate]siloxane] (P-8)

Poly[methyl[2-chloro-4-[4-((S)-2-methyl-1-butoxy)phenyloxy carbonyl]phenyl 3-chloro-4-(10-undecen-1-yloxy)benzoate]siloxane] (P-9)

Polymethylhydrogensiloxane (Code PS120) having a number average molecular weight of 2270 and platinum-divinyltetramethyldisiloxane complex catalyst were obtained from Petrarch Systems Inc., Bristal, Pa., U.S.A. and used as received. 1.15 equivalent moles of compounds I-13~I-17 and I-22~I-25 were separately dissolved in an suitable amount of toluene together with polymethylhydrogensiloxane. The reactions were carried out at about 110° C. in the presence of platinum divinyltetramethyldisiloxane complex catalyst. FT-IR analysis was run to detect the absorption peak of Si—H bond (2180 cm$^{-1}$) of the reaction mixture. The hydrosilation reaction was complete when the Si—H absorption peak disappeared. The polymers were separated and purified by several reprecipitations from a tetrahydrofuran solution into methanol. The purified polymers were further subjected to preparative GPC or thin layer chromatography (TLC) to detect whether the purified polymers were free of any residual monomers or oligomers. The reprecipitation was repeated until the GPC or TLC showed no residual monomers or oligomers existing in the purified polymers.

Table 3 shows that the monomers used in the syntheses of polymers P-1~P-9, and the relationship between these polymers and the above formula (I).

TABLE 3

| Example | monomer | m | n | Ar | Ar' | x$_1$ | x$_2$ |
|---|---|---|---|---|---|---|---|
| 1 | I-13 | 80 | 1 | biphenylene | phenylene | — | — |
| 2 | I-14 | 80 | 2 | biphenylene | phenylene | — | — |
| 3 | I-15 | 80 | 3 | biphenylene | phenylene | — | — |
| 4 | I-16 | 80 | 4 | biphenylene | phenylene | — | — |
| 5 | I-17 | 80 | 9 | biphenylene | phenylene | — | — |
| 6 | I-22 | 40 | 9 | —C$_6$H$_3$(X$_1$)—C(=O)—O—C$_6$H$_3$(X$_2$)— | phenylene | H | H |
| 7 | I-23 | 40 | 9 | | phenylene | H | Cl |
| 8 | I-24 | 40 | 9 | | phenylene | Cl | H |
| 9 | I-25 | 40 | 9 | | phenylene | Cl | Cl |

The thermal transitions, thermodynamic and mesophases of monomers I-13 to I-17, and polymers P-1 to P-5 are discussed below:

The monomers I-13 to I-17 and polymers P-1 to P-5 were characterized by differential scanning calorimetry and optical polarizing microscopy.

Figure 27:
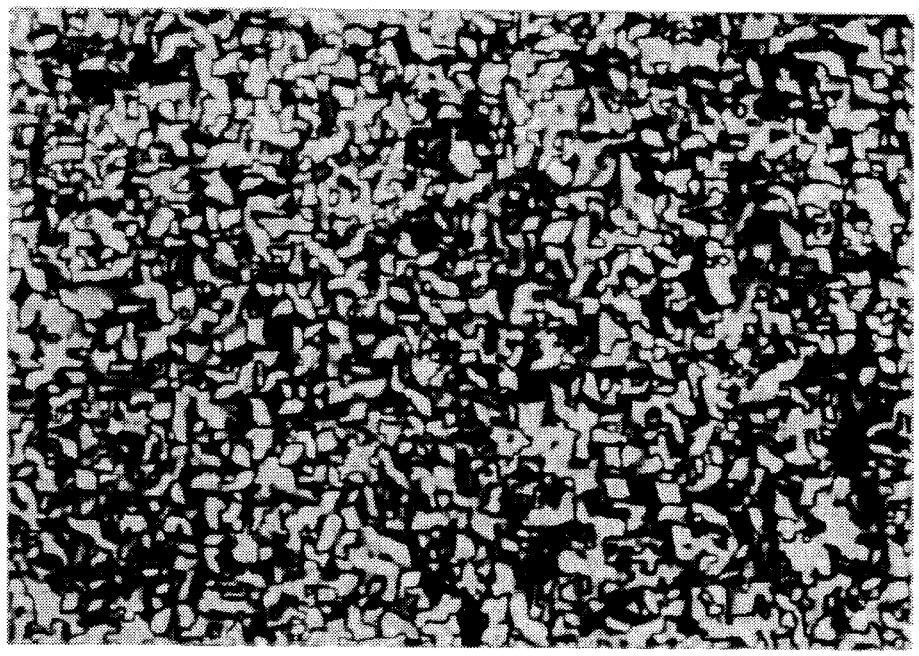
FIGS. 27(A), (B) are typical optical polarizing micrographs (magnification 640×) of monomer I-13: (A) schlieren texture obtained at 199.4° C.; (B) focal-conic texture obtained at 181.4° C.
Figure 27:
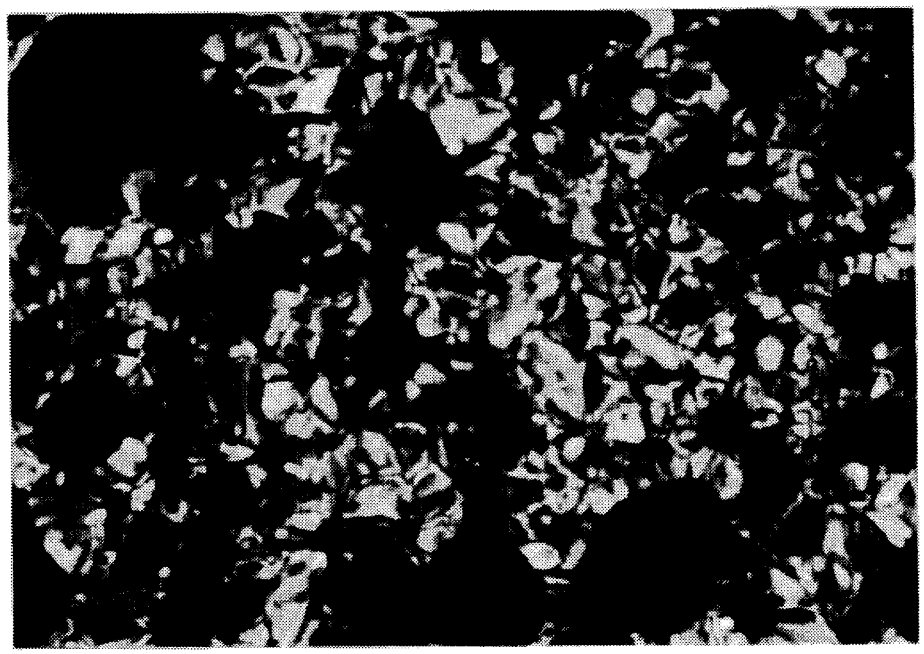

The monomers I-13 to I-17 and polymers P-1 to P-5 have spacers of different numbers of carbon atom, wherein the monomers all exhibit significant liquid crystalline mesophases but some of the polymers does not show significant liquid crystalline mesophases. FIG. 1 presents the DSC heating and cooling traces of monomer I-13. From FIG. 1 and with the help from optical polarizing microscopy, the mesophases of monomer I-13 can be identified. The monomer I-13 exhibits isotropization at 200° C., and the optical polarizing micrograph taken at this temperature displays a dark phase. When the temperature decreases from 200° C., the optical polarizing micrograph displays a schlieren texture and the color thereof gradually changes, and thus it is determined as cholesteric mesophase. FIG. 27(A) is an optical polarizing micrograph (magnification 640x) of the schlieren texture exhibited by monomer I-13 at 199.4° C. As the temperature further drops to 181 ° C., the optical polarizing micrograph (magnification 640x) FIG. 27(B) displays a typical focal-conic fan texture of the smectic A mesophase. Monomer I-13 crystallizes when the temperature is reduced to lower than 100° C.

Figure 2:
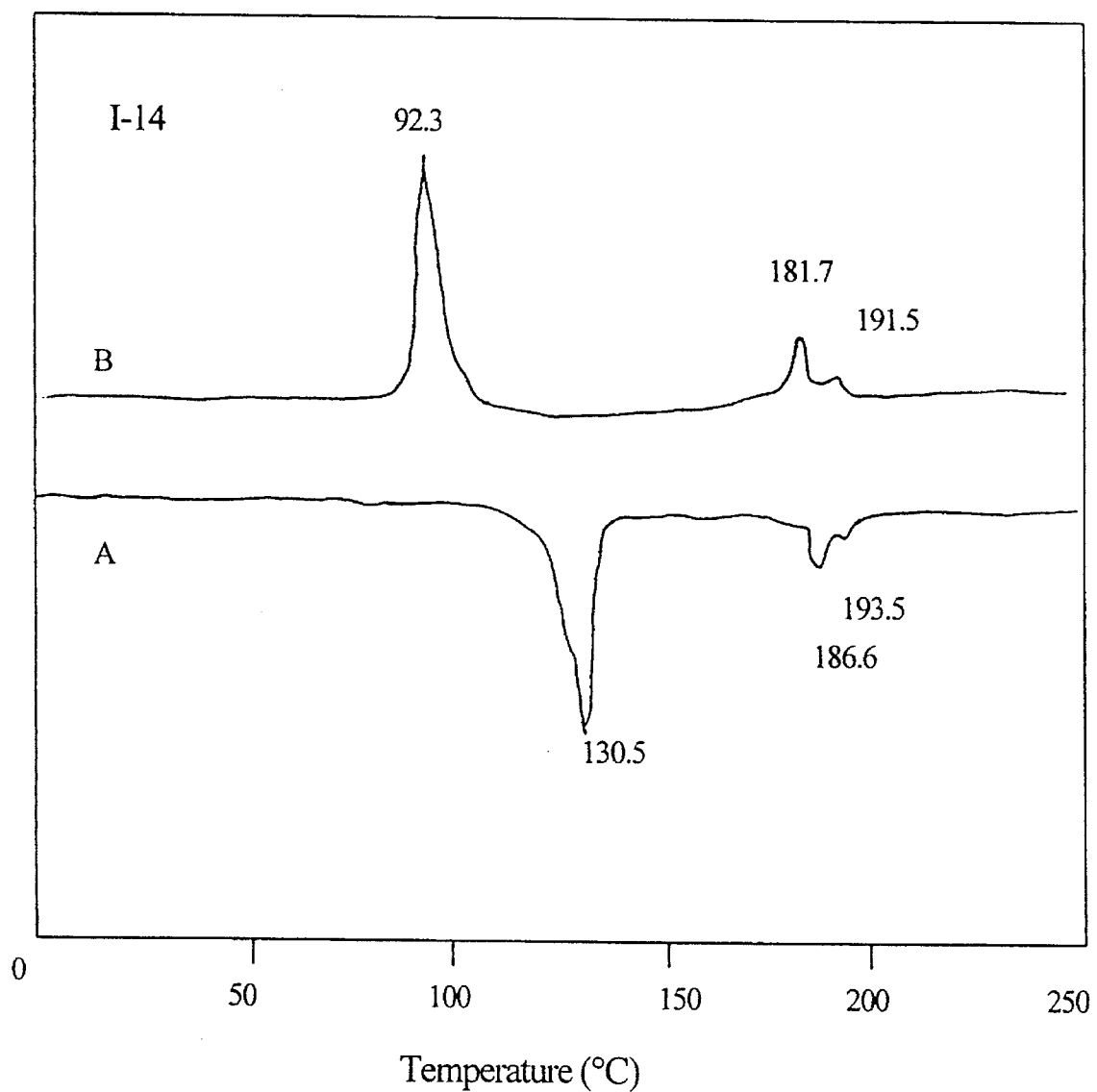
FIG. 2 is a Differential Scanning Calorimeter (DSC) thermogram (10° C./min) for monomer I-14: A) heating scan; B) cooling scan.
Figure 28:
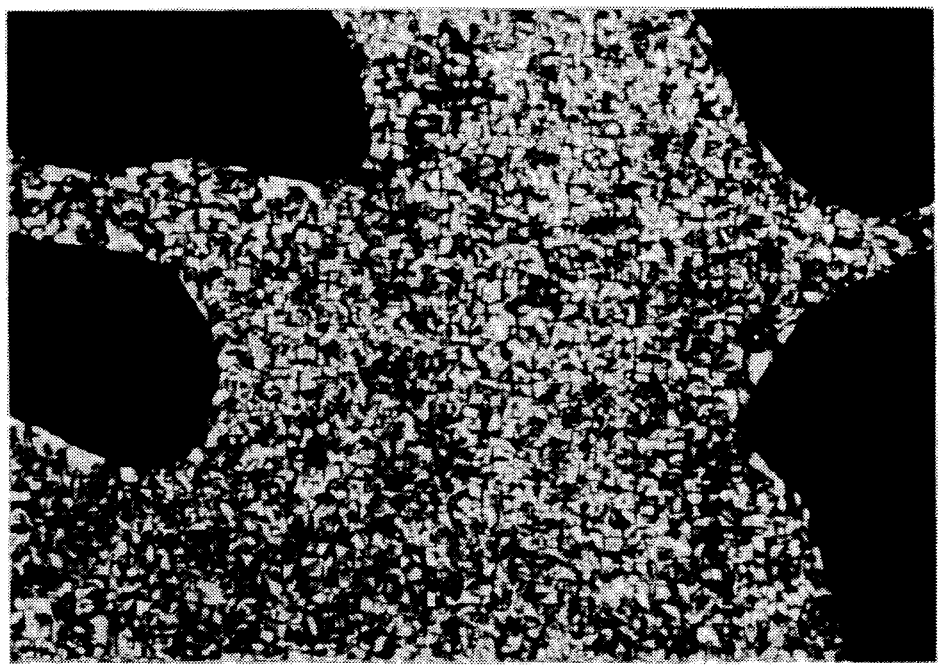
FIGS. 28(A), (B) are typical optical polarizing micrographs (magnification 400×) of monomer I-14: (A) schlieren texture obtained at 193.6° C.; (B) schlieren texture obtained at 192.9° C.
Figure 28:
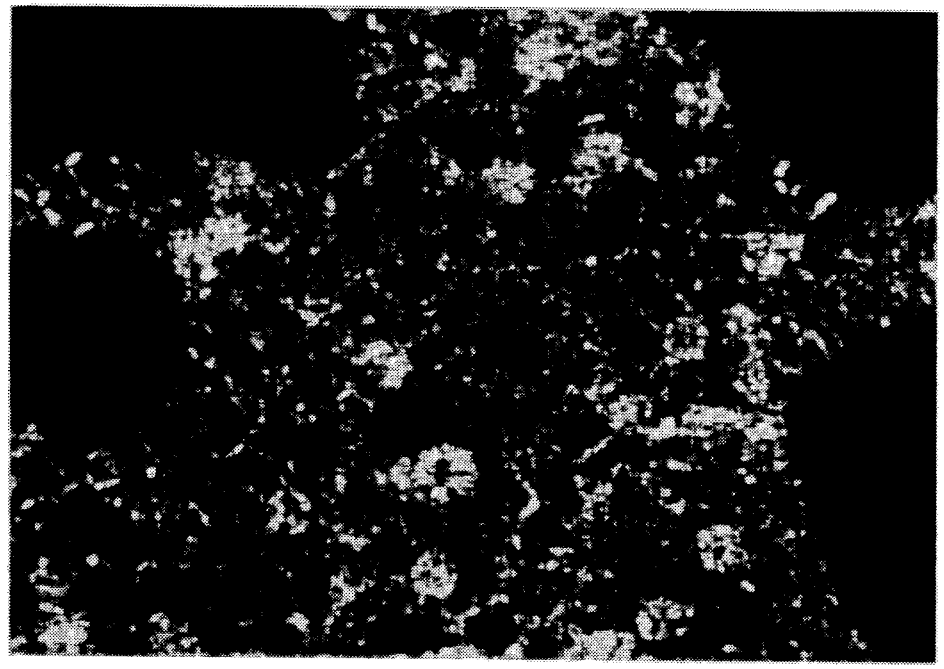

FIG. 2 presents the DSC heating and cooling traces of monomer I-14. The optical polarizing microscopy is again used to identify the mesophases of monomer I-14. The monomer I-14 exhibits isotropization at 194° C. When the temperature decreases from 194° C., the optical polarizing micrograph displays a schlieren texture and the color thereof gradually changes, and thus it is determined as cholesteric mesophase. FIGS. 28(A) and 28(B) are optical polarizing micrographs (magnification 400x) of the schlieren texture exhibited by monomer I-14 at 193.6° C. and 192.9° C. As the temperature further drops to 181.7° C., the optical polarizing micrograph of the monomer I-14 displays a homeotropi phase. Monomer I-14 crystallizes when the temperature is reduced to lower than 92.3° C. The homeotropi phase may be smectic mesophase.

Figure 3:
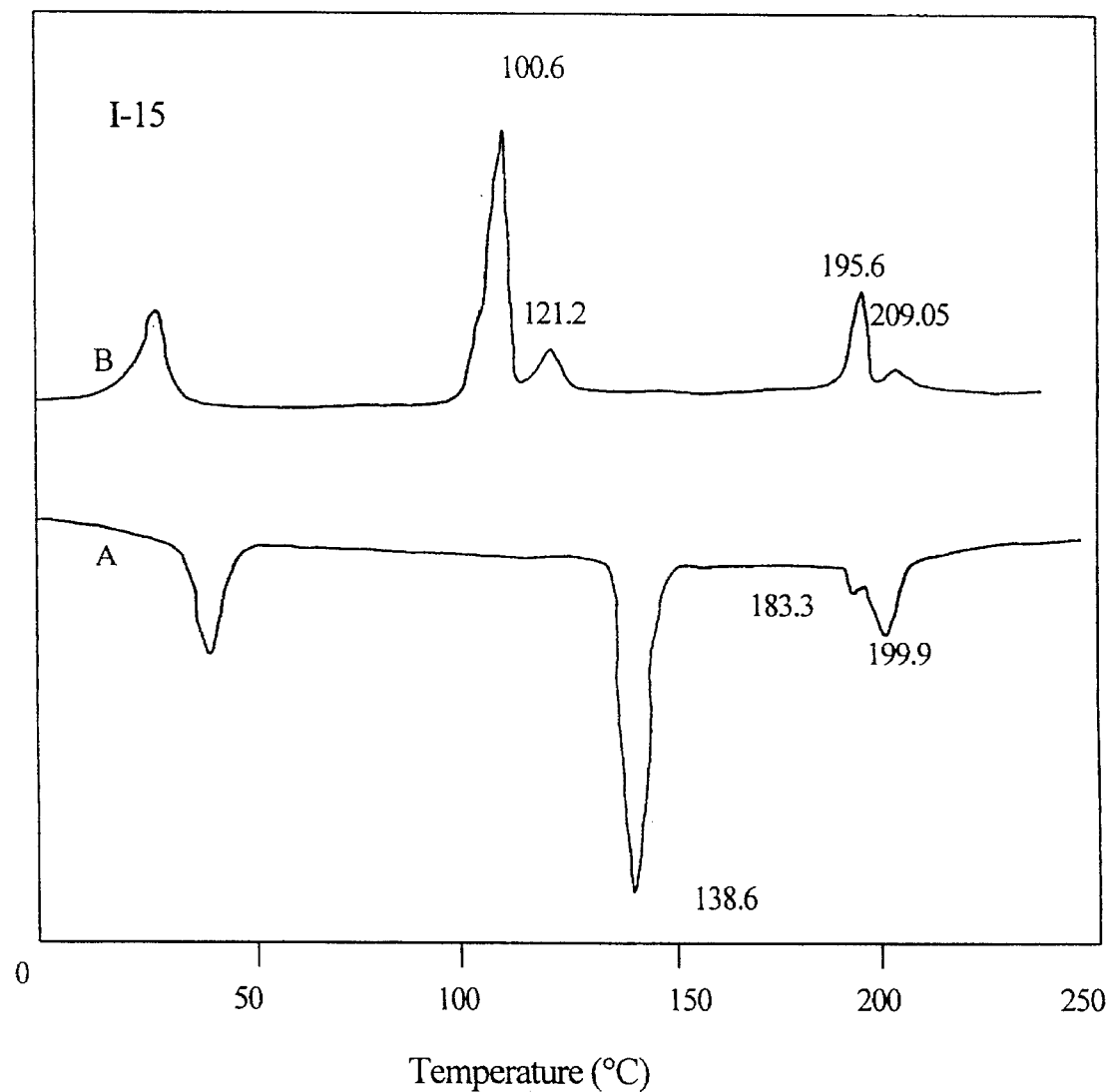
FIG. 3 is a Differential Scanning Calorimeter (DSC) thermogram (10° C./min) for monomer I-15: A) heating scan; B) cooling scan.
Figure 29:
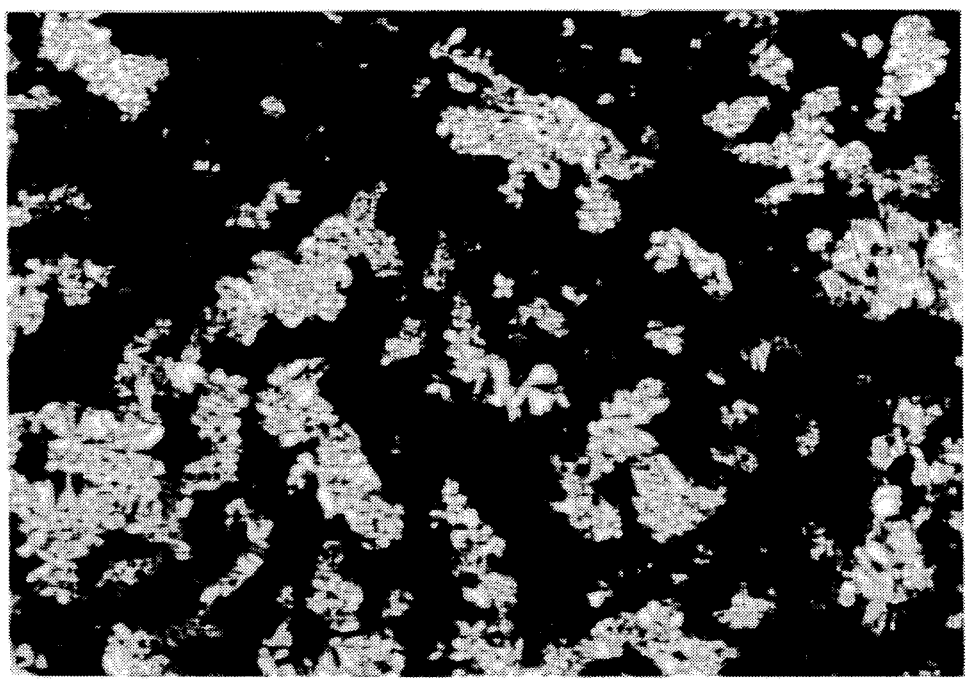
FIG. 29 is a typical optical polarizing micrograph (magnification 640×) of monomer I-15: schlieren and fan texture obtained at 195° C.

FIG. 3 presents the DSC heating and cooling traces of monomer I-15. The optical polarizing micrograph of monomer I-15 taken at 200° C. displays a cholesteric mesophase. When the temperature decreases to 195° C., the optical polarizing micrograph displays a schlieren and fan texture, and thus it is determined as a cholesteric mesophase carrying a smectic A mesophase. FIG. 29 is an optical polarizing micrograph (magnification 640x) of the schlieren and fan texture exhibited by monomer I-15 at 195° C. As the temperature further drops to 121.2° C., the optical polarizing micrograph of the monomer I-15 displays only a fan texture and no schlieren texture. Monomer I-15 crystallizes when the temperature is reduced to lower than 101 ° C.

Figure 4:
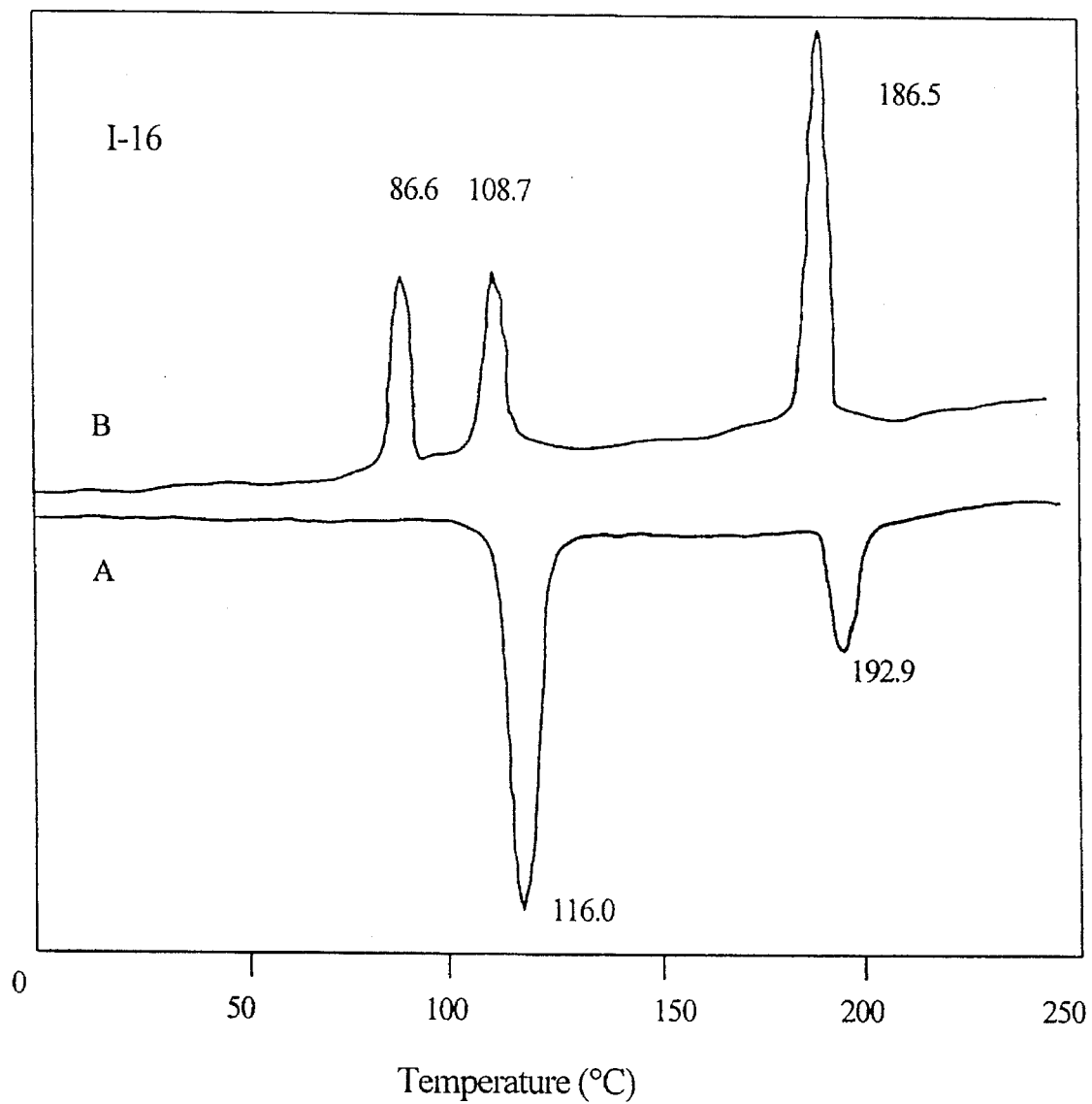
FIG. 4 is a Differential Scanning Calorimeter (DSC) thermogram (10° C./min) for monomer I-16: A) heating scan; B) cooling scan.
Figure 5:
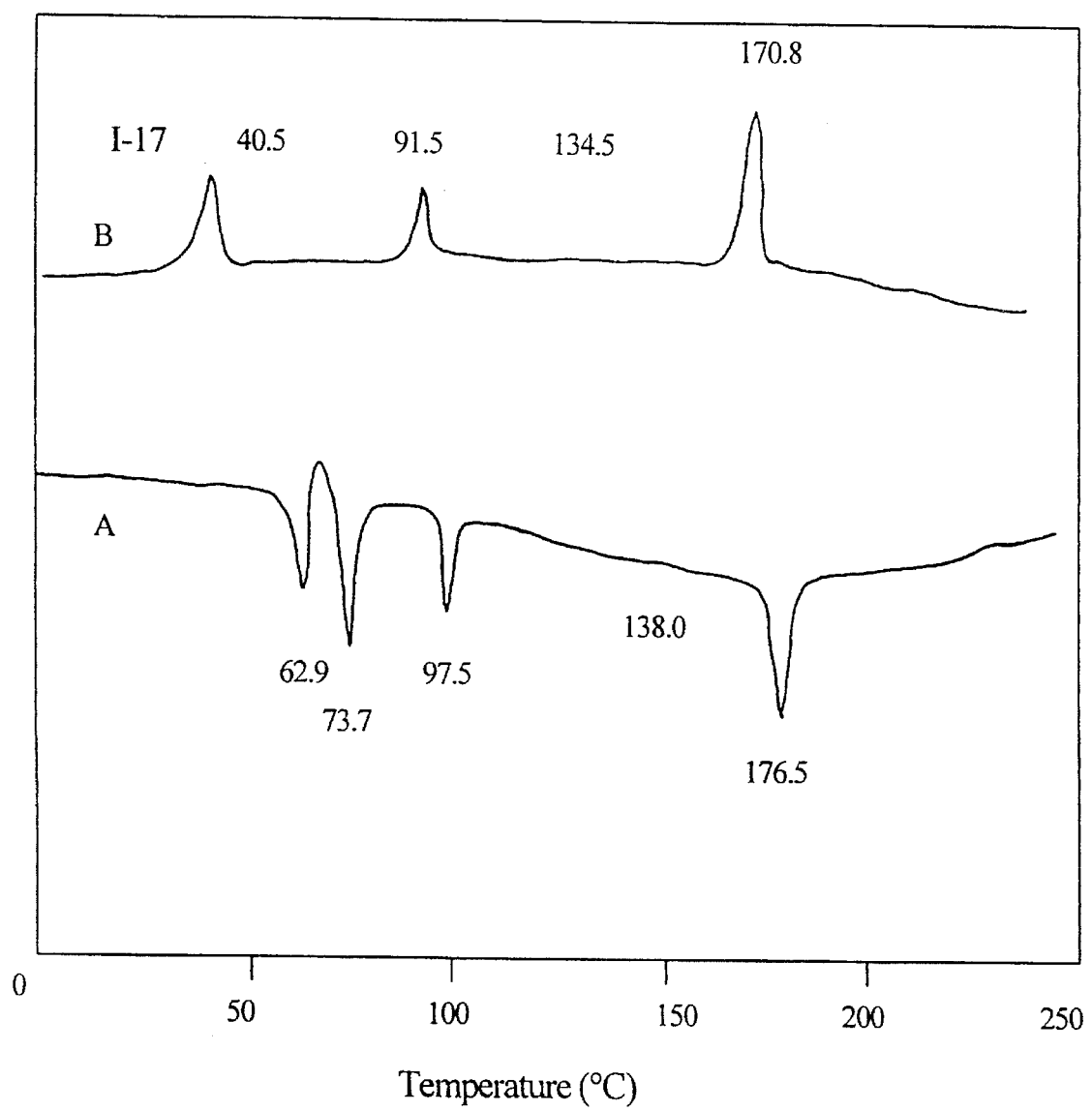
FIG. 5 is a Differential Scanning Calorimeter (DSC) thermogram (10° C./min) for monomer I-17: A) heating scan; B) cooling scan.
Figure 30:
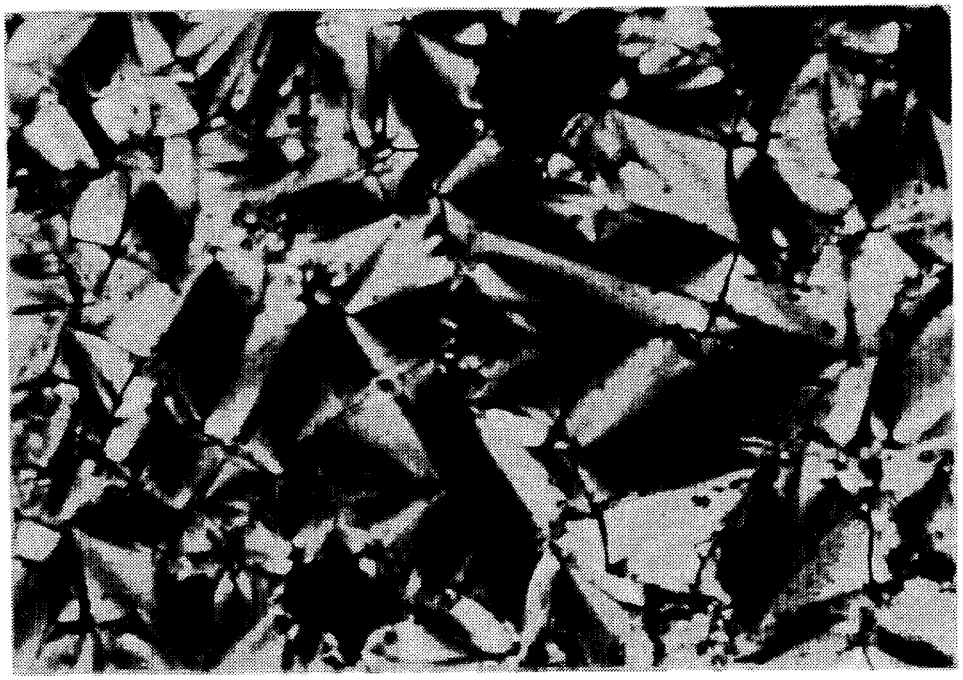
FIGS. 30(A), (B), (C), (D) are typical optical polarizing micrographs (magnification 640×) of monomer I-16: (A) focal-conic fan texture obtained at 187° C.; (B) banded focal-conic fan texture obtained at 109.7° C.; (C) the texture obtained at 86.6° C.; (D) the texture obtained at 64.1 ° C.
Figure 30:
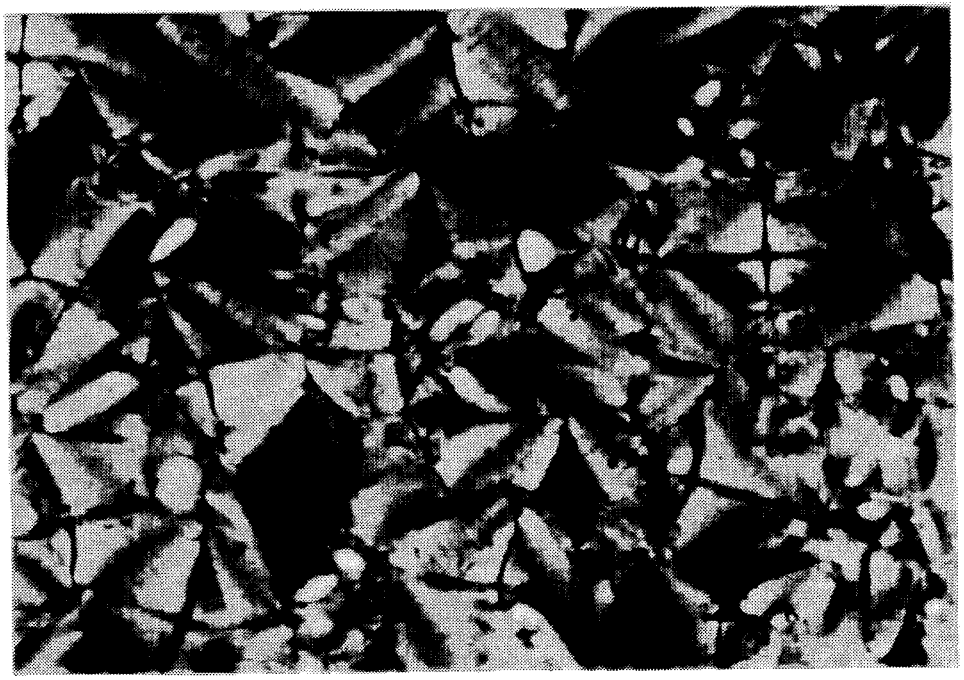
Figure 30:
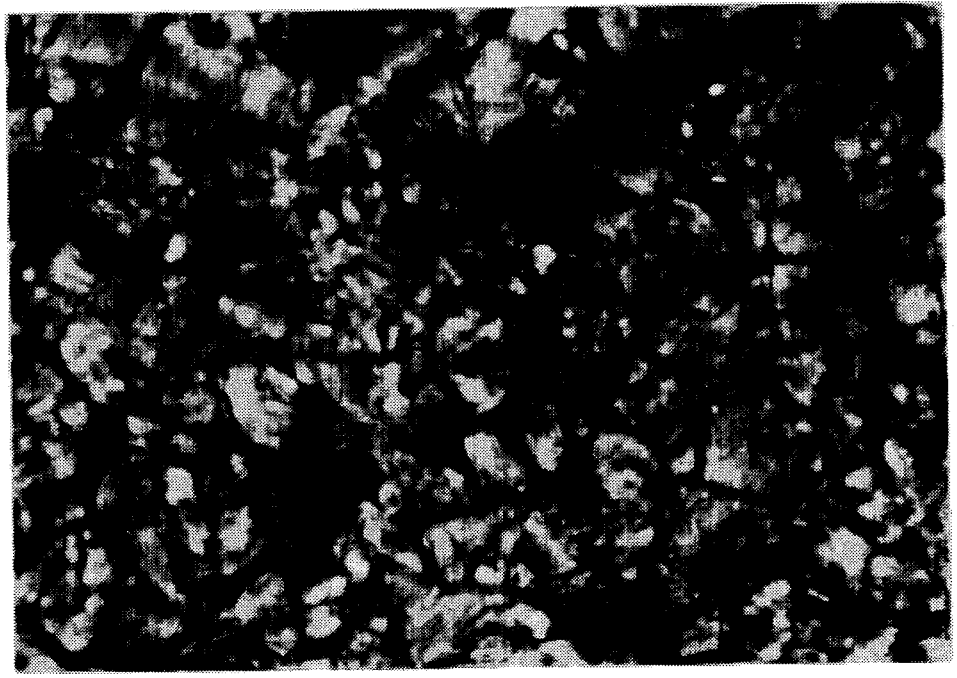
Figure 30:
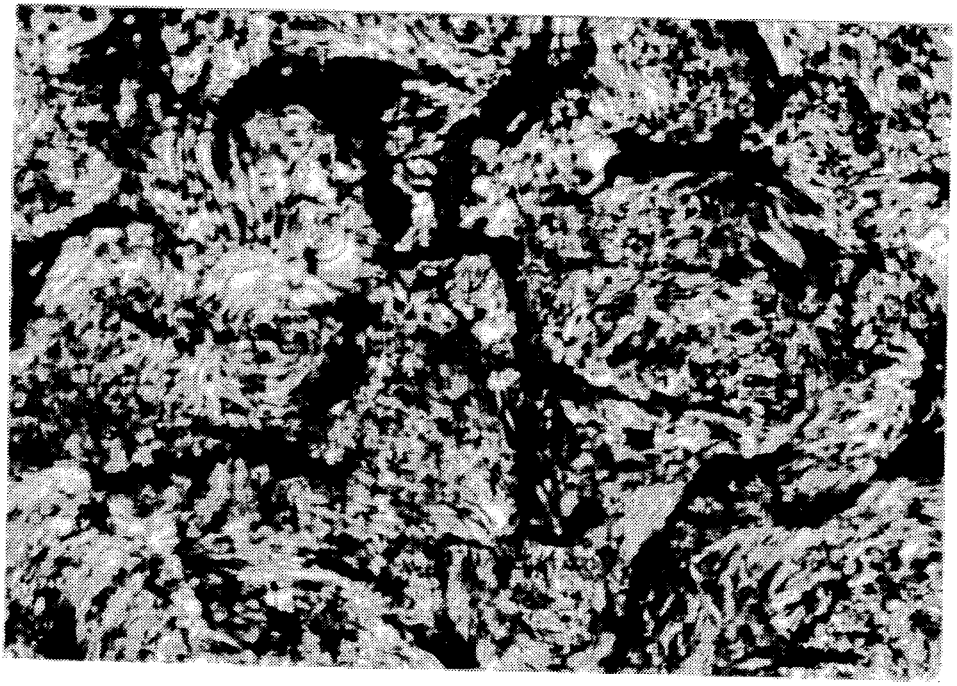
Figure 31:
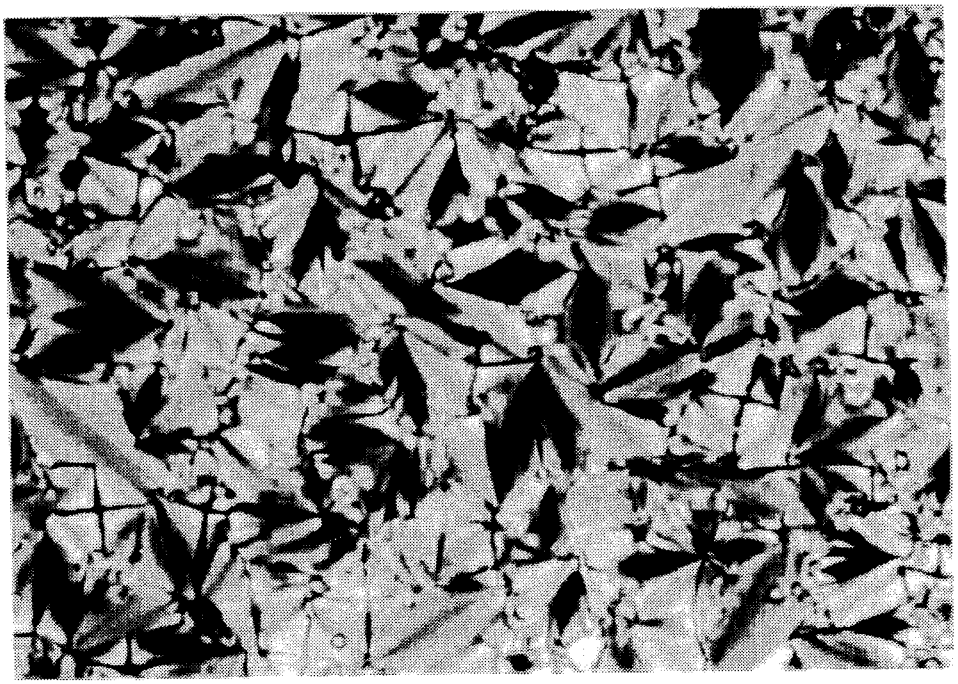
FIGS. 31(A), (B) are typical optical polarizing micrographs (magnification 640×) of monomer I-17: (A) focal-conic fan texture obtained at 171° C.; (B) smectic phase texture obtained at 134° C.
Figure 31:
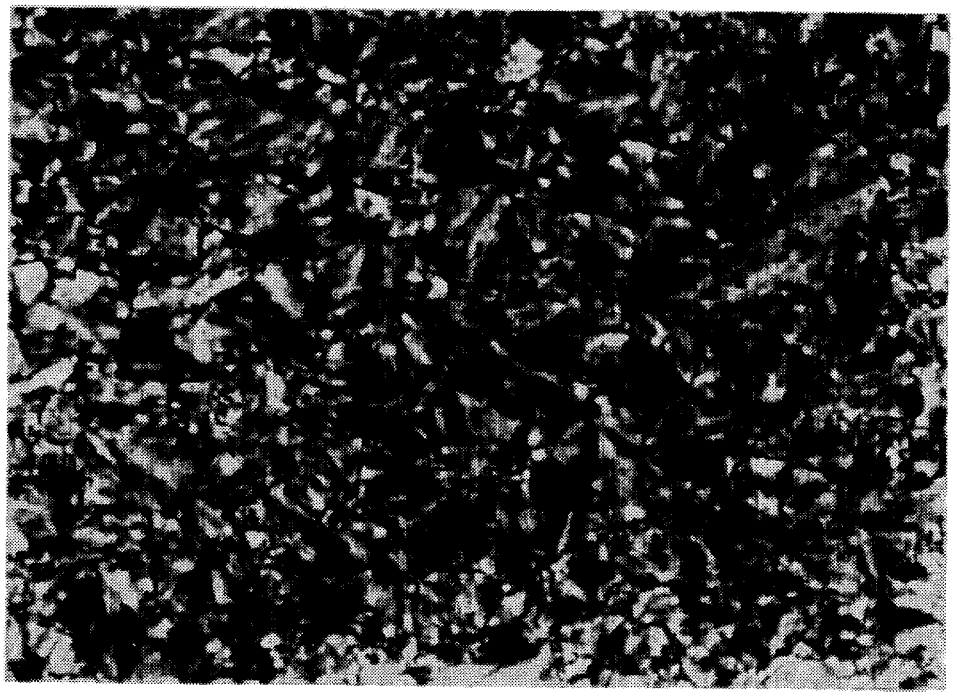

FIG. 4 presents the DSC heating and cooling traces of monomer I-16. The optical polarizing micrograph of monomer I-16 taken at 187° C. displays a focal-conic fan texture of smectic A mesophase [FIG. 30(A)]. When the temperature decreases to 109° C., the optical polarizing micrograph [FIG. 30(B)] displays a banded focal-conic fan texture. FIG. 30(C) is an optical polarizing micrograph (magnification 640x) exhibited by monomer I-16 at 86.6° C., and the texture thereof can not be identified what type of mesophase it pertains to. As the temperature further drops to 64.1° C. , the monomer I-16 crystallizes [FIG. 30(D)]. Monomer I -16 exhibits only one smectic A mesophase on the heating scan, and that is to say chiral smectic C phase is a monotropic phase FIG. 5 presents the DSC heating and cooling traces of monomer I-17. The optical polarizing micrograph of monomer I-17 taken 171° C. displays a focal-conic fan texture of smectic A mesophase [FIG. 31(A)]. When the temperature decreases to 134° C., the optical polarizing micrograph [FIG. 31(B)] displays a chiral smectic C phase. As the temperature further drops to 92° C., the monomer I-17 forms smectic B phase, and crystallizes at 41° C. Monomer I-17 exhibits a relative small peak on the DSC traces when a transition from a smectic A phase to a chiral smectic C phase occurs, because of a small energy jump from a smectic A phase to a chiral smectic C phase. However, the optical polarizing microscopy does clearly show the transitions between the mesophases. Monomer I-17 exhibits a melting point at 63° C. on the heating scan of DSC. Since a melting point is accompanied with a supercool phenomenon and the phase transition is not, one can clearly discriminate the melting point from the mesophase transitions on the DSC traces.

Figure 6:
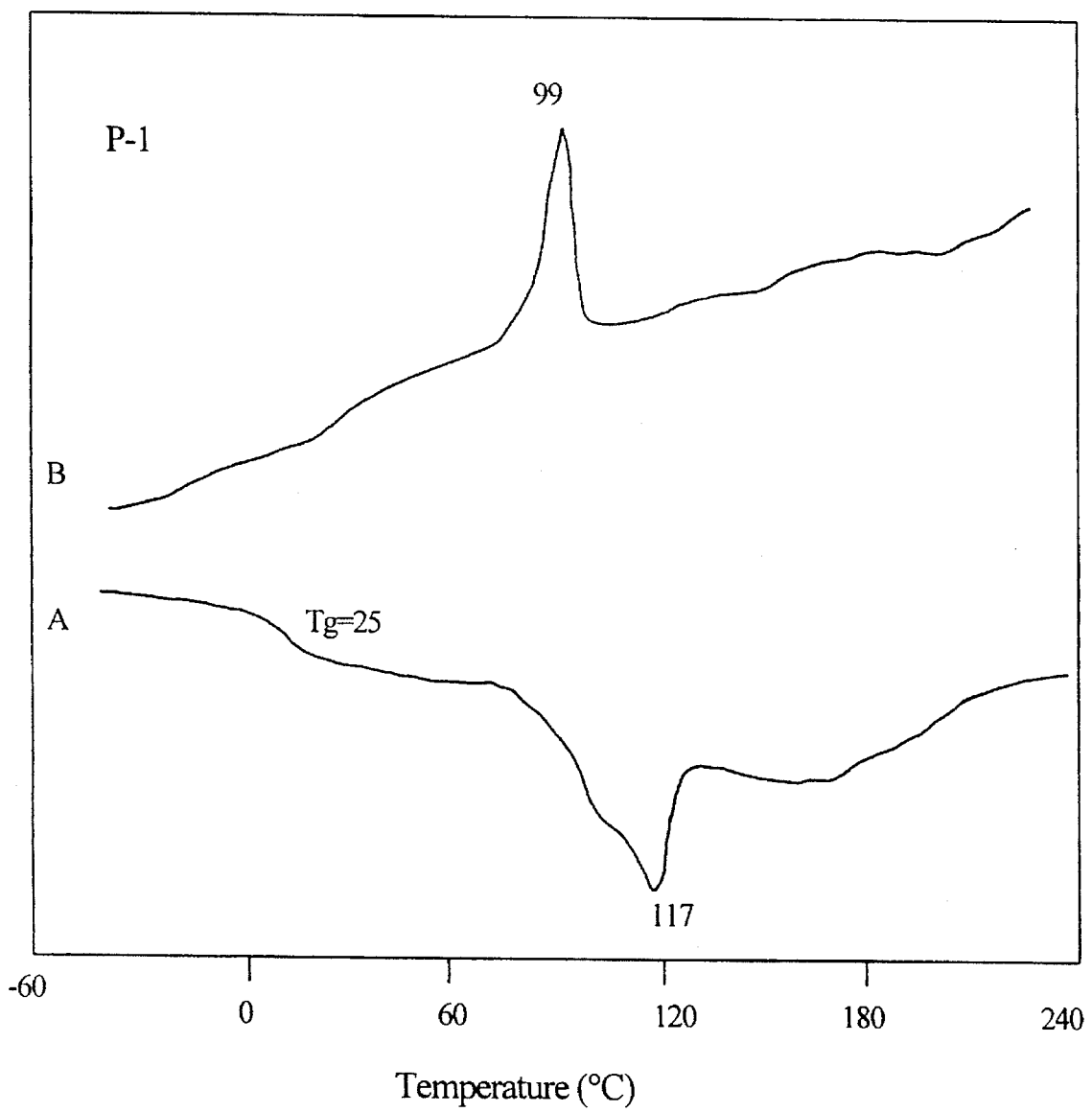
FIG. 6 is a Differential Scanning Calorimeter (DSC) thermogram (10° C./min) for polymer P-1: A) heating scan; B) cooling scan.
Figure 32:
FIG. 32 is typical optical polarizing micrograph (magnification 400×) of polymer P-1: smectic texture obtained at room temperature.

FIG. 6 presents the DSC heating and cooling traces of polymer P-1, which show that polymer P-1 has a glass transition temperature (Tg) of 25° C. and one phase transition temperature. The optical polarizing microscopy shows that polymer P-1 exhibits a smectic A mesophase (FIG. 32).

Figure 7:
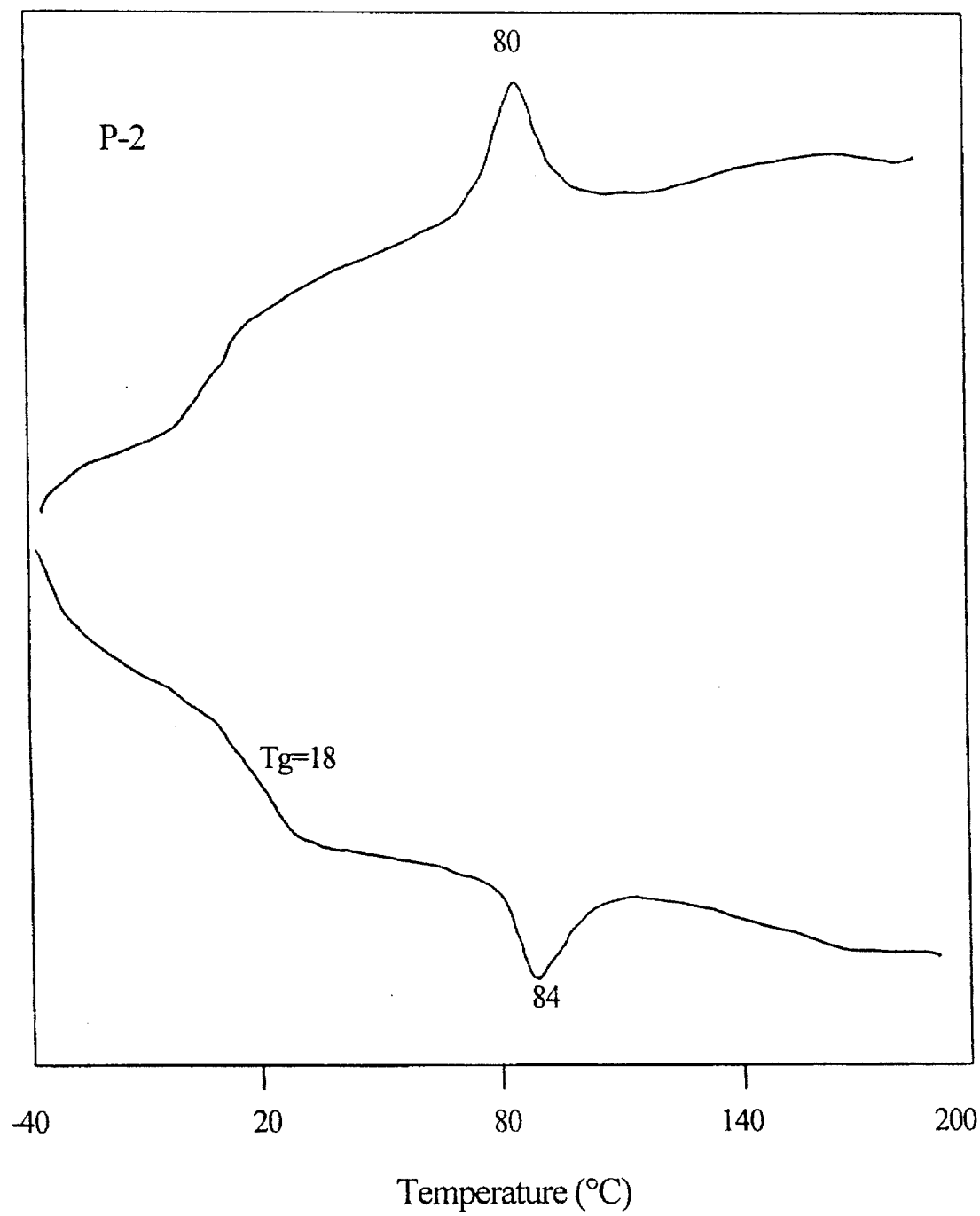
FIG. 7 is a Differential Scanning Calorimeter (DSC) thermogram (10° C./min) for polymer P-2: A) heating scan; B) cooling scan.
Figure 33:
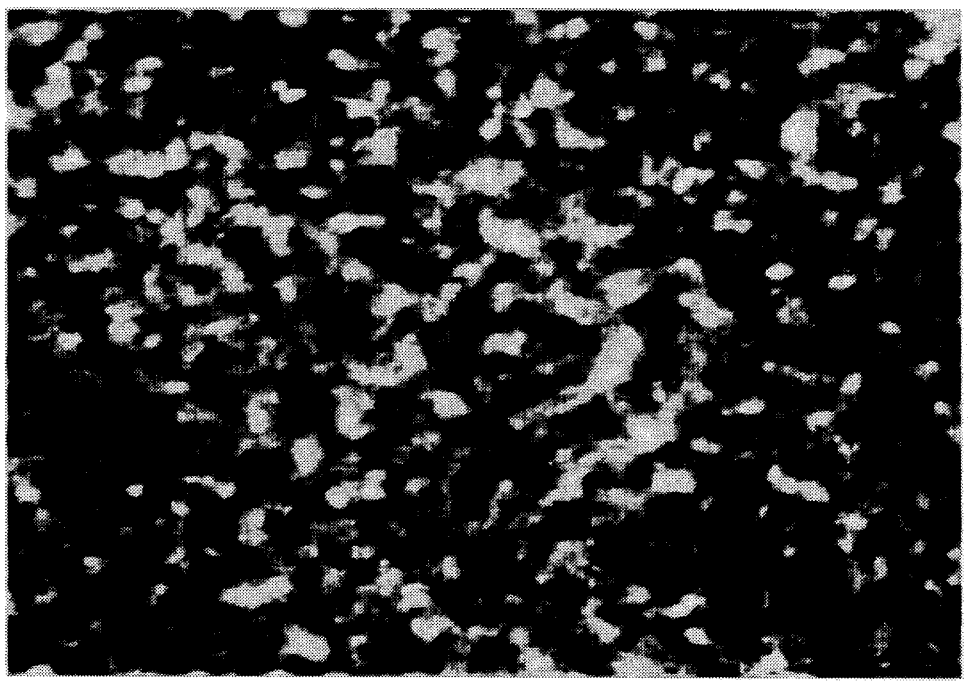
FIG. 33 is typical optical polarizing micrograph (magnification 800×) of polymer P-2: smectic texture obtained at 80° C.

FIG. 7 presents the DSC heating and cooling traces of polymer P-2, which show that polymer P-2 has a glass transition temperature (Tg) of 18° C. and one phase transition temperature. The optical polarizing microscopy shows that polymer P-2 exhibits a smectic A mesophase (FIG. 33).

Figure 8:
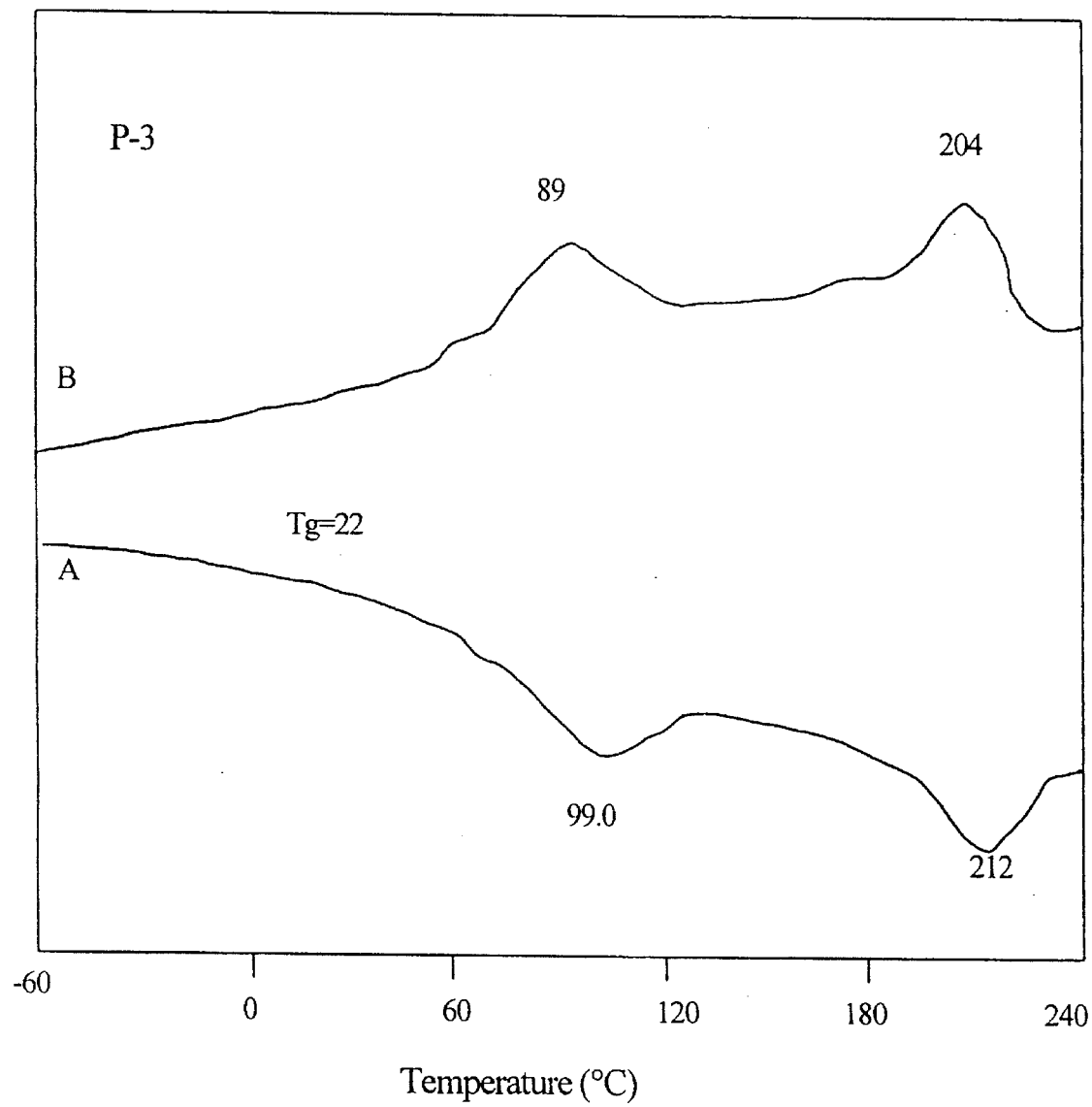
FIG. 8 is a Differential Scanning Calorimeter (DSC) thermogram (10° C./min) for polymer P-3: A) heating scan; B) cooling scan.
Figure 34:
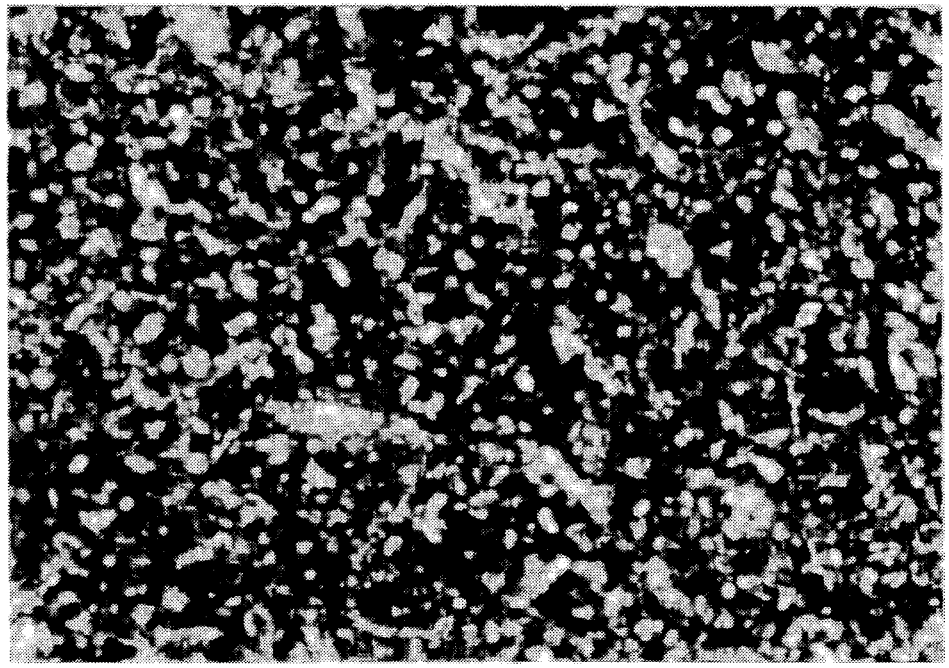
FIGS. 34(A), (B) are typical optical polarizing micrographs (magnification 800×) of polymer P-3: (A) batonnets texture obtained at 203.9° C.; (B) the texture obtained at room temperature.
Figure 34:
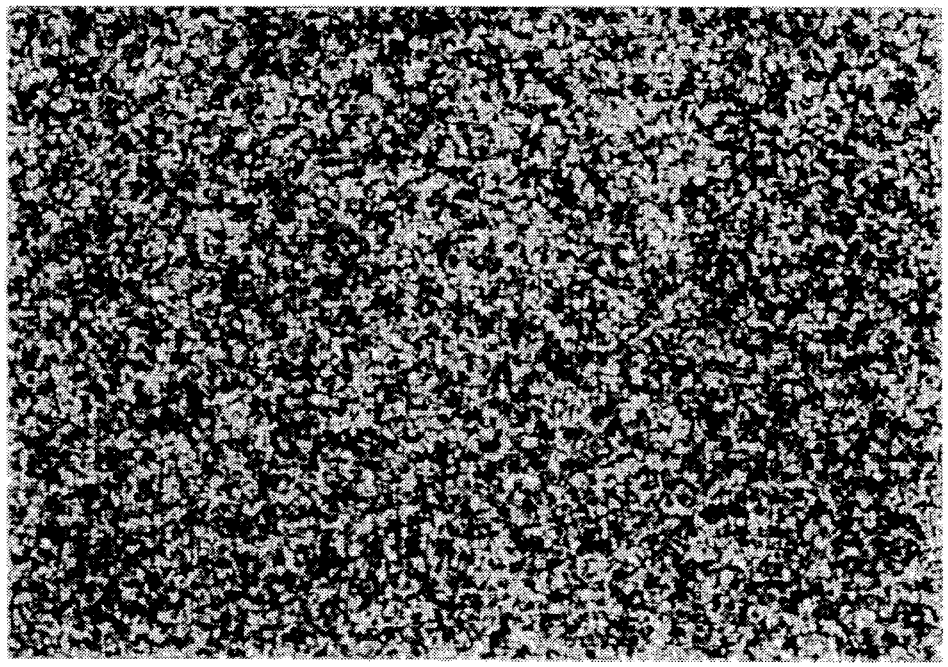

FIG. 8 presents the DSC heating and cooling traces of polymer P-3. FIG. 34(A) displays a batonnetx texture of smectic A phase exhibited by polymer P-3 at 203.9° C. The liquid crystalline polymer P-3 is frozen when the temperature is reduced to room temperature. FIG. 34(B) is an optical polarizing micrograph of polymer P-3 taken at room temperature, and the texture thereof is presumed as a texture exhibited by a smectic phase, probably a smectic B phase.

Figure 9:
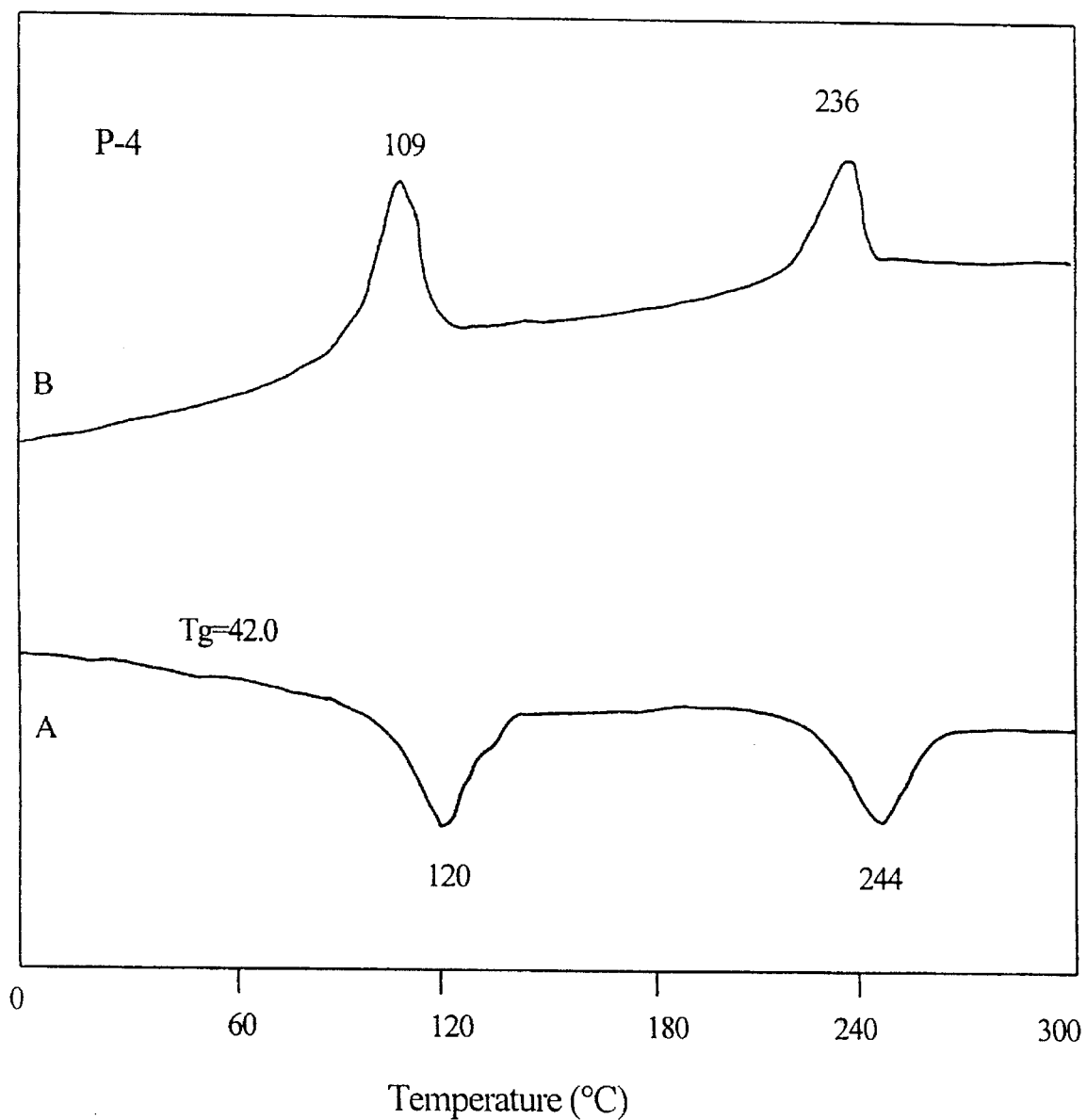
FIG. 9 is a Differential Scanning Calorimeter (DSC) thermogram (10° C./min) for polymer P-4: A) heating scan; B) cooling scan.
Figure 35:
FIGS. 35(A), (B), (C) are typical optical polarizing micrographs (magnification 800×) of polymer P-4: (A) smectic A texture obtained at 236° C.; (B) chiral smectic C texture obtained at 161.8° C.; (C) smectic B texture obtained at 98° C.
Figure 35:
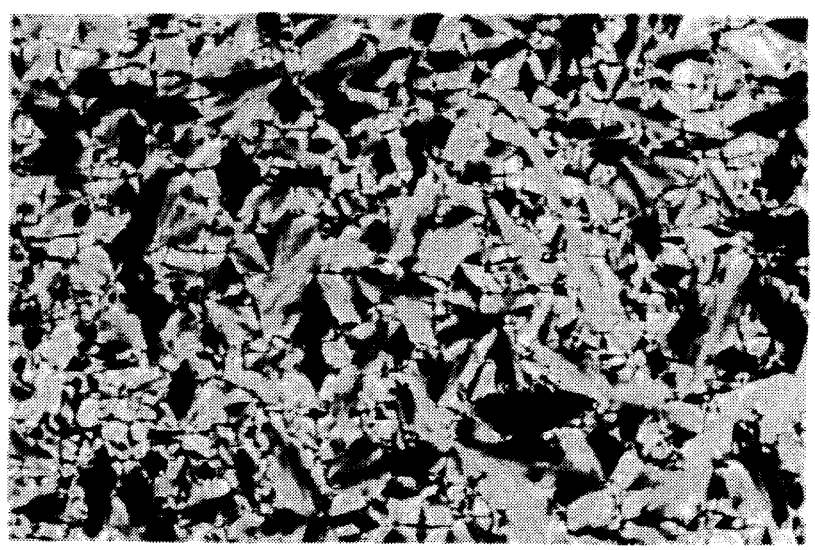
Figure 35C:
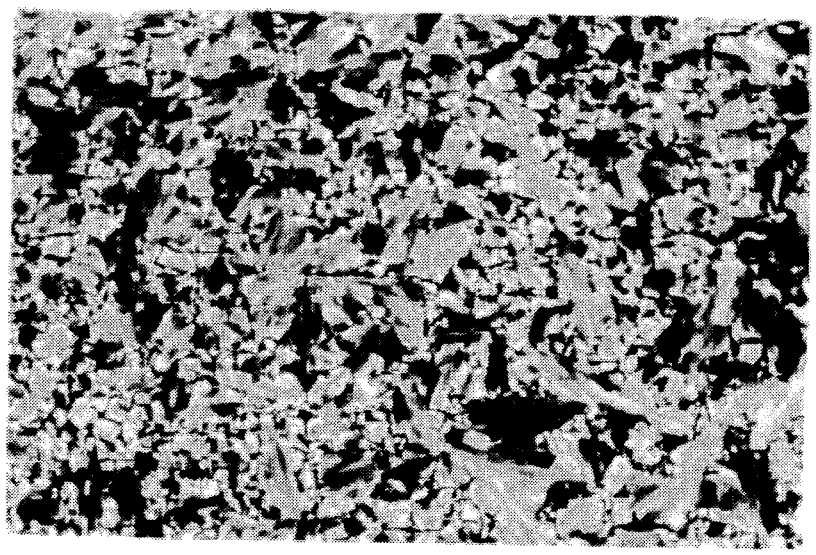

FIG. 9 presents the DSC heating and cooling traces of polymer P-4, which show that polymer P-4 has a glass transition temperature (Tg) of 16° C. The optical polarizing micrograph of polymer P-4 taken at 236° C. displays a focal-conic fan texture of smectic A mesophase [FIG. 35(A)]. When the temperature decreases to 161.8° C., the optical polarizing micrograph [FIG. 35(B)] displays a texture of chiral smectic C phase. When the temperature further decreases to 98° C., the optical polarizing micrograph [FIG. 35(C)] displays a texture of smectic B phase.

Figure 10:
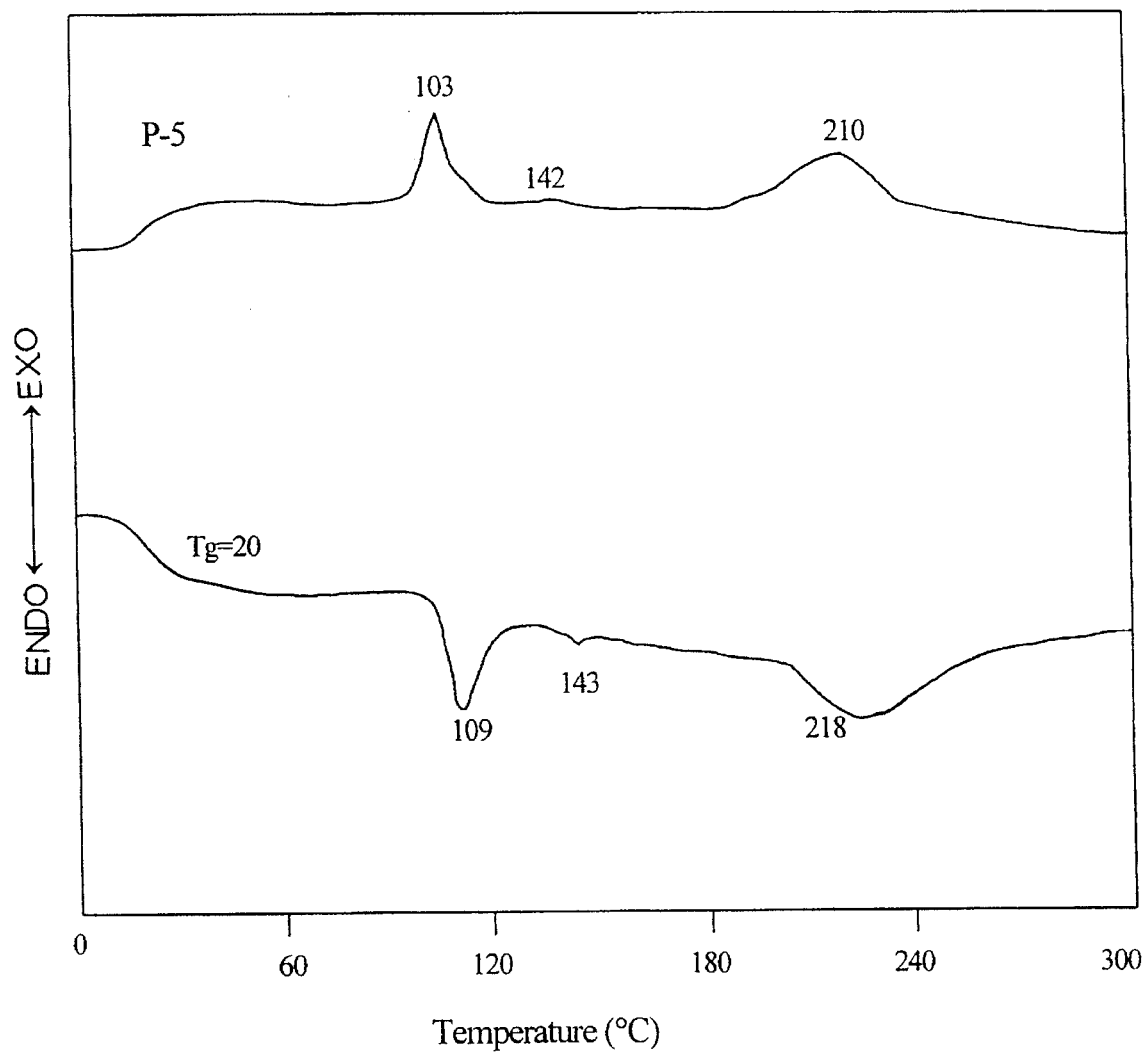
FIG. 10 is a Differential Scanning Calorimeter (DSC) thermogram (10° C./min) for polymer P-5: A) heating scan; B) cooling scan.
Figure 36:
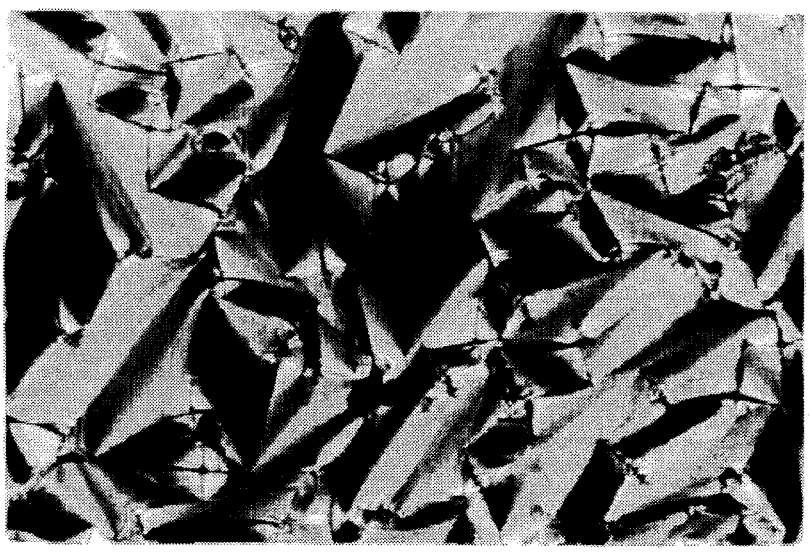
FIGS. 36(A), (B), (C) are typical optical polarizing micrographs (magnification 800×) of polymer P-5: (A) smectic A texture obtained at 180.9° C.; (B) chiral smectic C texture obtained at 134.3° C.; (C) smectic B texture obtained at 106.5° C.
Figure 36:
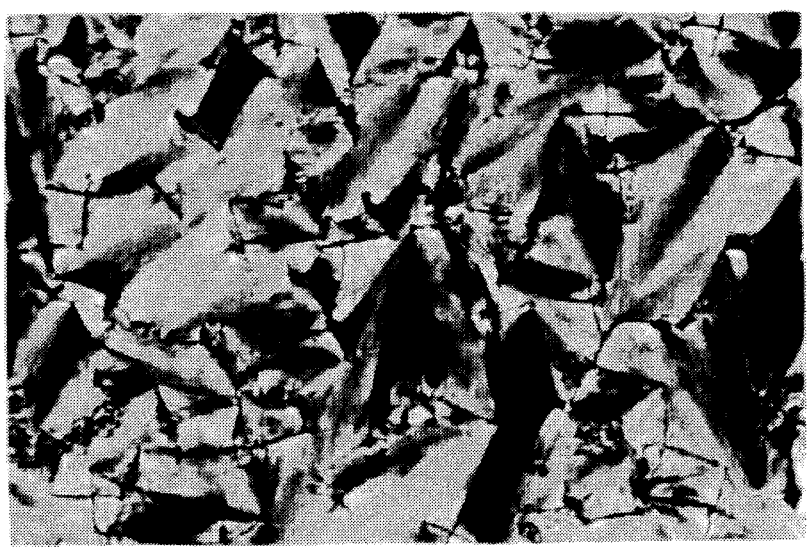
Figure 36C:

FIG. 10 presents the DSC heating and cooling traces of polymer P-5, which show that polymer P-5 has a glass transition temperature (Tg) of 20° C. The optical polarizing micrograph of polymer P-5 taken at 180.9° C. displays a texture of smectic A mesophase [FIG. 36(A)]. When the temperature decreases to 134.3° C., the optical polarizing micrograph [FIG. 36(B)] displays a texture of chiral smectic C phase. When the temperature further decreases to 106.5° C., the optical polarizing micrograph [FIG. 35(C)] displays a texture of smectic B phase. This smectic B phase of polymer P-5 is frozen when the temperature is reduced to room temperature.

Tables 4 and 5 present the thermal transitions and thermodynamic parameters of the synthesized monomers I-13 to I-17 and polymers P-1 to P-5 respectively.

Monomers I-13 to I-17 all exhibit significant liquid crystalline mesophases, and among them the monomer I-17 exhibits a chiral smectic C phase. It is found that a longer flexible spacer (such as carbon atom number 4 or 9) facilitates the formation of a chiral smectic C phase. It is believed that a longer flexible spacer which tends to form a regular arrangement of the side chains such as a smectic B or C phase and the terminal chiral unit are the reasons why the synthesized monomers exhibit the chiral smectic C characteristic. As to the polymers P-1 to P-5, some of them also exhibit liquid crystalline mesophases. Polymers P-4 and P-5 have a significant chiral smectic C phase, and this may be because a longer flexible spacer enhances the decoupling of motions of the side chain and the polymer backbone, and thus the side chain acts like the mesogenic monomer.

TABLE 4

Phase transitions and phase transition
enthalpies for monomers I-13~I-17

Phase transitions, °C. (corresponding enthalpy
changes, Kcal/mol)

| Monomer | n | heating / cooling |
|---|---|---|
| I-13 | 1 | K 130(3.89) $S_A$ 186(0.37) N* 200 (0.14) I |
| | | I 197(0.11) N* 181(0.38) $S_A$ 100(4.08) K |
| I-14 | 2 | K 131(4.56) $S_A$ 187 N* 194(0.34) I |
| | | I 193(0.14) N* 191(0.54) $S_A$ 92(3.79) K |
| I-15 | 3 | K 139(5.98) $S_A$ 183(0.22) N* 200(1.64 ) I |
| | | I 199(0.67) N* 195(0.67) $S_A$ 101(2.89) K |
| I-16 | 4 | K 116(5.25) $S_A$ 193(1.26) I |
| | | I 137(1.43) $S_A$ 109(0.71) $S_B$ 86.6(0.66) K |
| I-17 | 9 | K 63(0.93) $S_B$ 98(0.61) $S_C$* 138(—)$^b$ $S_A$ 176(1.56) I |
| | | I 171(1.34) $S_A$ 134(—)$^b$ $S_C$* 92(0.61) $S_B$ 41(1.05) K |

Enthalpy is very small.

TABLE 5

Thermal transitions and phase transition
transition enthalpies for polymers P-1~P-5

Phase transitions, °C. (corresponding enthalpy
changes, Kcal/mru$^b$)

| Polymer | n | heating / cooling |
|---|---|---|
| P-1 | 1 | g 25 $S_A$ 117(1.82) I |
| | | I 99(1.80) $S_A$ |
| P-2 | 2 | g 18 $S_A$ 94(0.73) I |
| | | I 80(0.42) $S_A$ |
| P-3 | 3 | g 22 $S_B$ 99(0.39) $S_A$212(0.86) I |
| | | I 204(0.68) $S_A$ 89(0.82) $S_B$ |
| P-4 | 4 | g 16 $S_B$ 120(1.73) $S_C$* 166(—)$^c$ $S_A$ 244(1.24) I |
| | | I 236(0.98) $S_A$ 164(—)$^c$ $S_C$* 109(1.47) $S_B$ |
| P-5 | 9 | g 20 $S_B$ 109(0.73) $S_C$* 143 (—)$^c$ $S_A$ 218(0.36) I |
| | | I 210(0.89) $S_A$ 142(—)$^c$ $S_C$* 103(0.74) $S_B$ |

The thermal transitions, thermodynamic and mesophases of monomers I-22 to I-25, and polymers P-6 to P-9 are discussed below:

The monomers I-22 to I-35 and polymers P-6 to P-9 were characterized by differential scanning calorimetry and optical polarizing microscopy.

The monomers I-13 to I-17 and polymers P-1 to P-5 synthesized have different substituents on the Ar in the formulas (IIA) and (I) respectively. These four monomers and four polymers all exhibit significant liquid crystalline mesophases but polymers P-6, P-8 and P-9 exhibit side chain crystallization.

Figure 11:
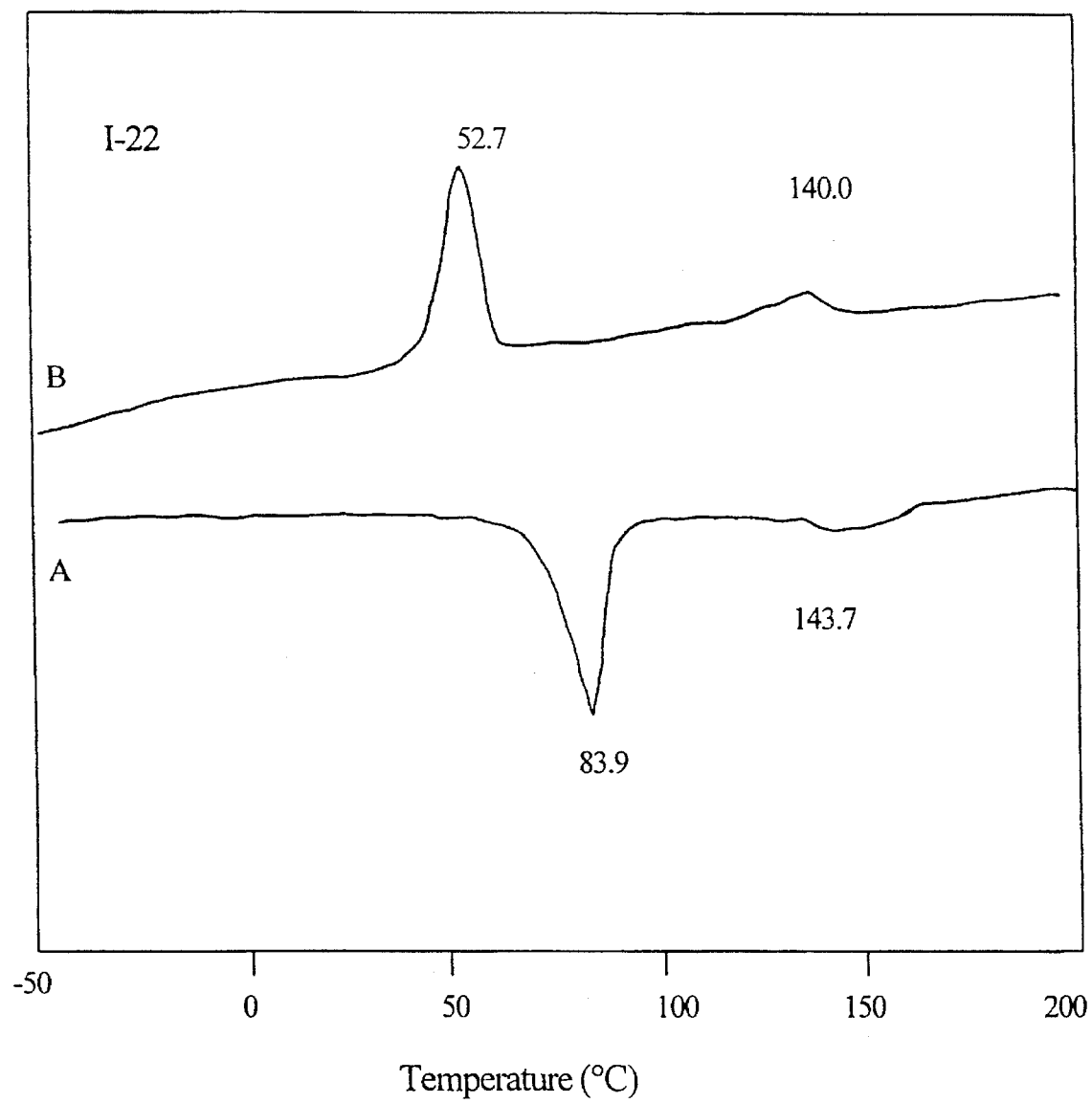
FIG. 11 is a Differential Scanning Calorimeter (DSC) thermogram (10° C./min) for monomer I-22: A) heating scan; B) cooling scan.
Figure 37:
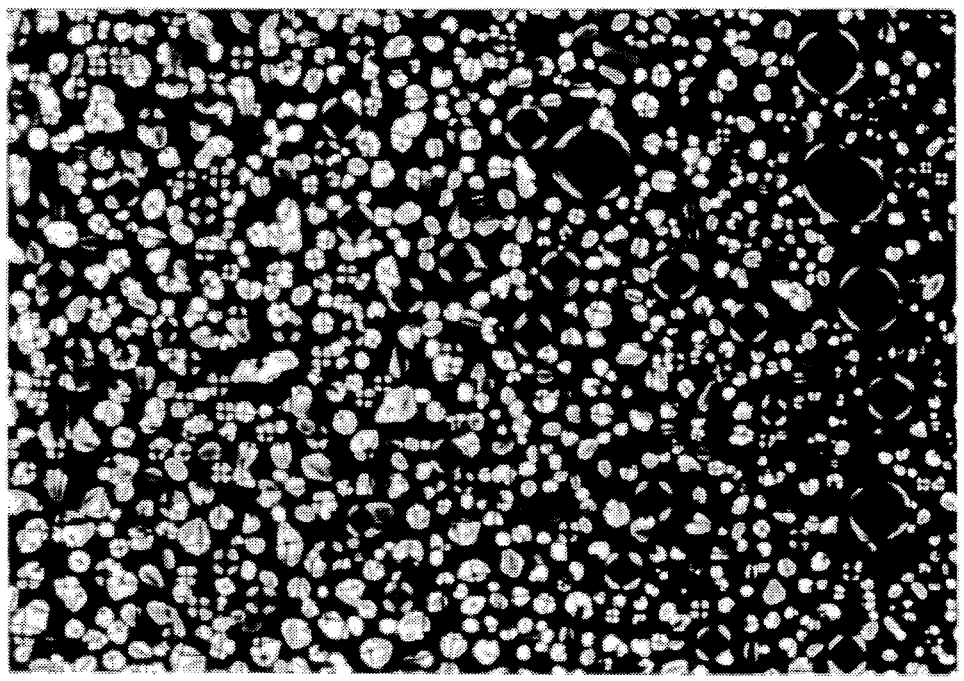
FIGS. 37(A), (B), (C), (D) are typical optical polarizing micrographs (magnification 400×) of monomer I-22: (A) fan shape texture obtained at 140° C.; (B) fan shape texture obtained at 120.3° C.; (C) fan shape texture obtained at 88.4° C.; (D) fan shape texture obtained at 52.7° C.
Figure 37:
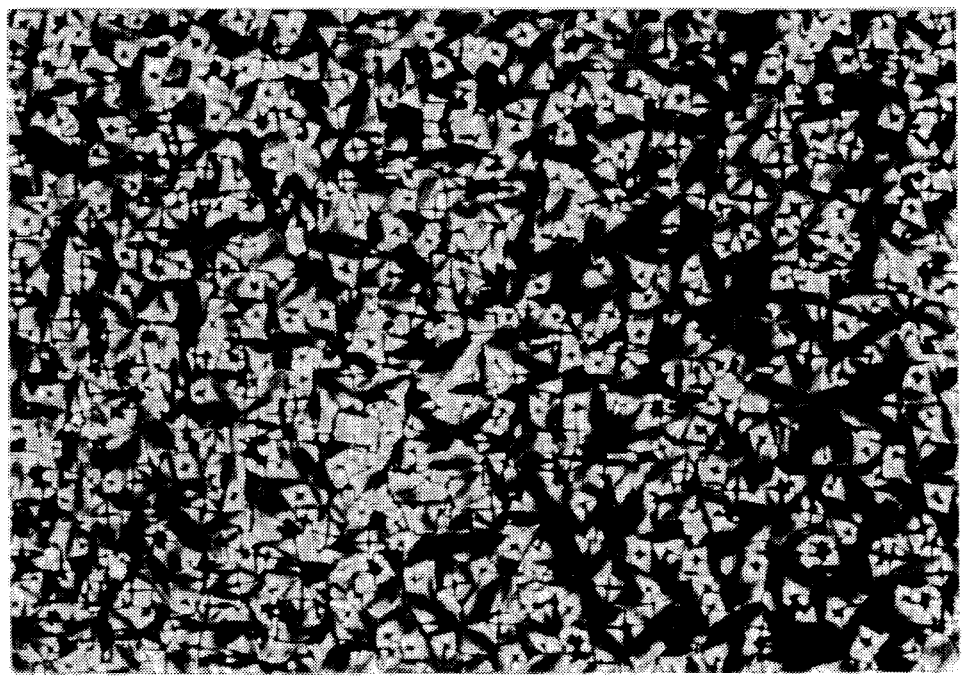
Figure 37:
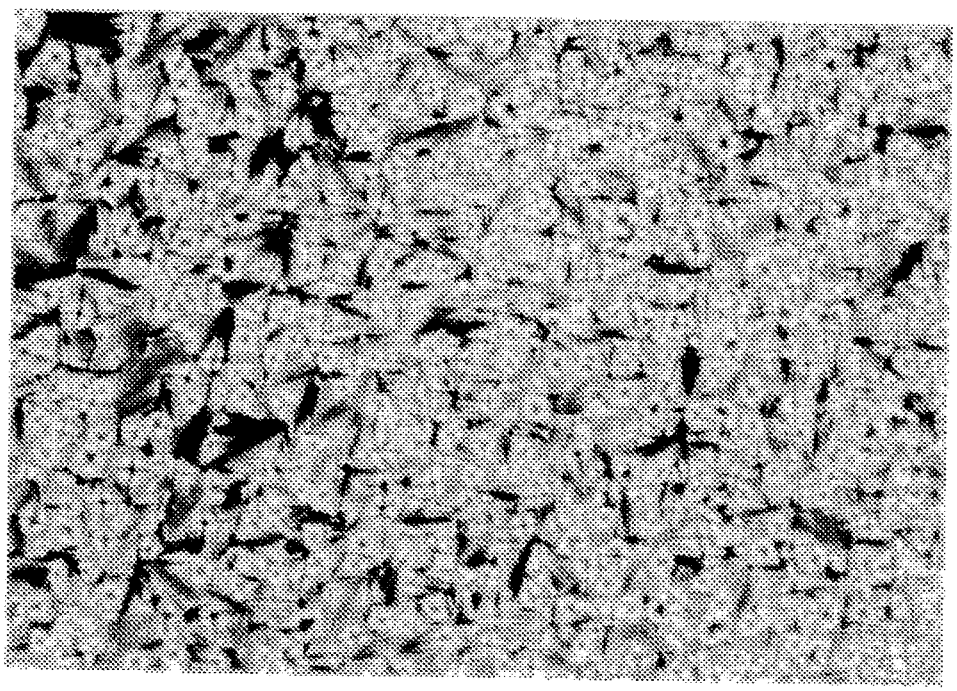
Figure 37:
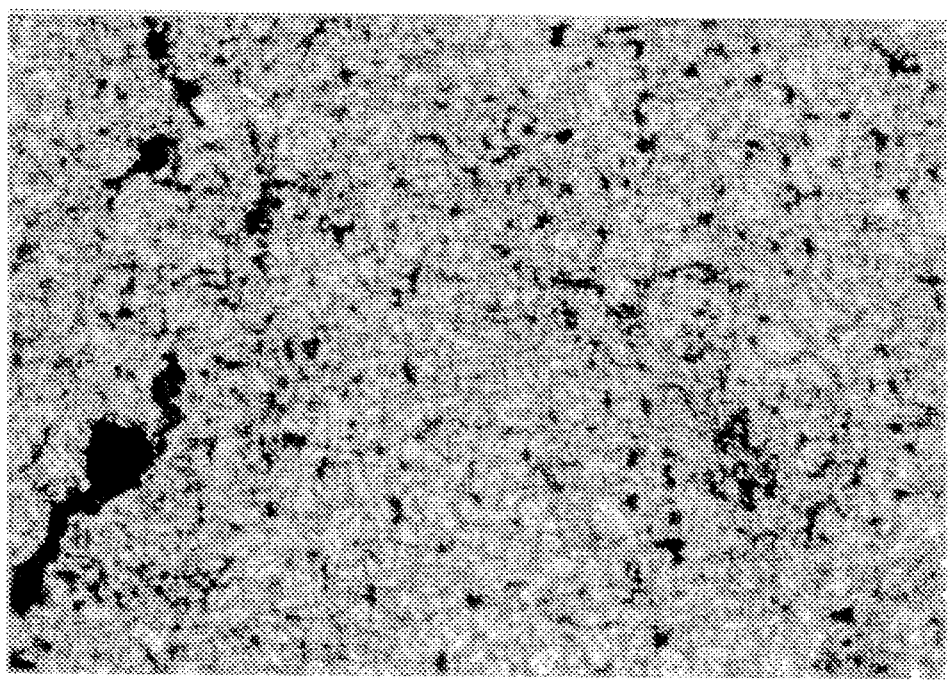

FIG. 11 presents the DSC heating and cooling traces of monomer I-22. From FIG. 1 and with the help from optical polarizing microscopy, the mesophases of monomer I-22 can be identified. The optical polarizing micrograph of monomer I-22 taken at 140.0° C. [FIG. 37(A)] displays a fan shape texture of smectic A phase. When the temperature decreases from 140.0° C., the size of the fan shape texture grows [FIGS. 37(B) and 37(C)]. Monomer I-22 crystallizes when the temperature is reduced to 52.7° C. [FIG. 37(D)].

Figure 12:
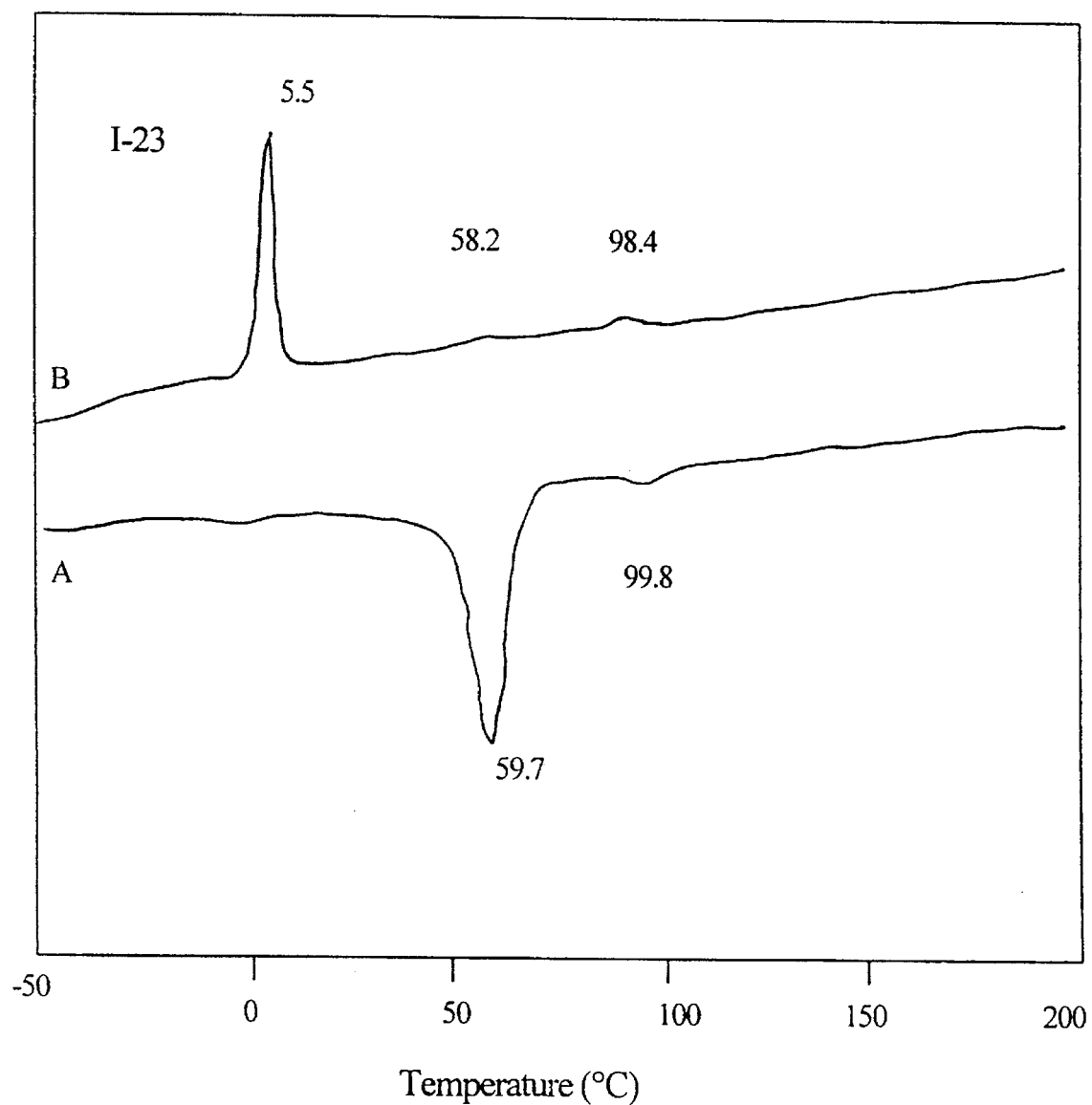
FIG. 12 is a Differential Scanning Calorimeter (DSC) thermogram (10° C./min) for monomer I-23: A) heating scan; B) cooling scan.
Figure 38:
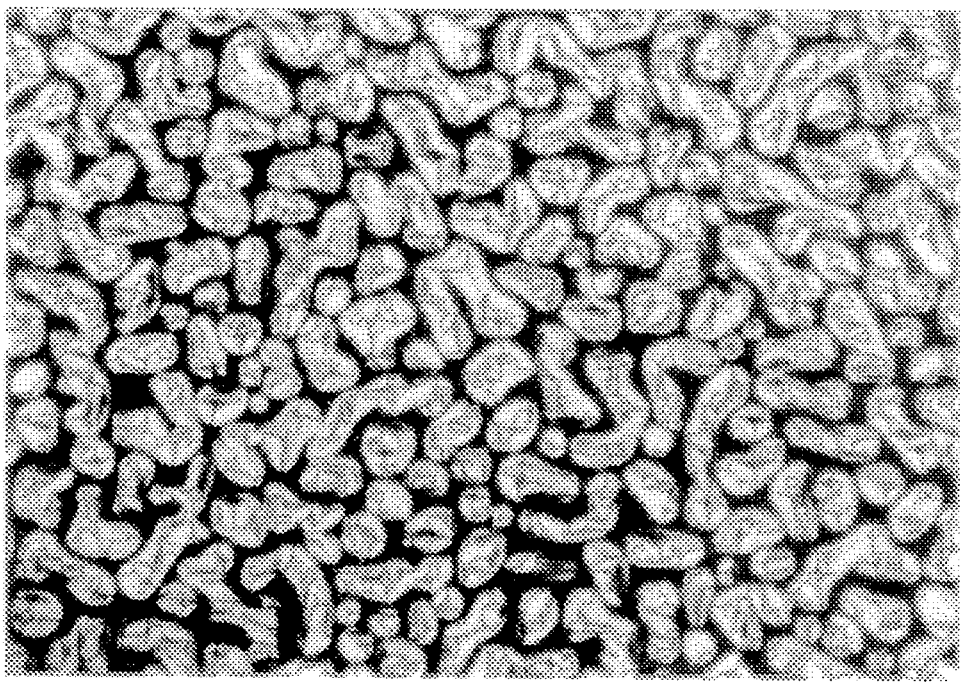
FIGS. 38(A), (B), (C) are typical optical polarizing micrographs (magnification 400×) of monomer I-23: (A) the texture obtained at 98.4° C.; (B) fan-like texture obtained at 71.2° C.; (C) bands drops texture obtained at 58.2° C.
Figure 38:
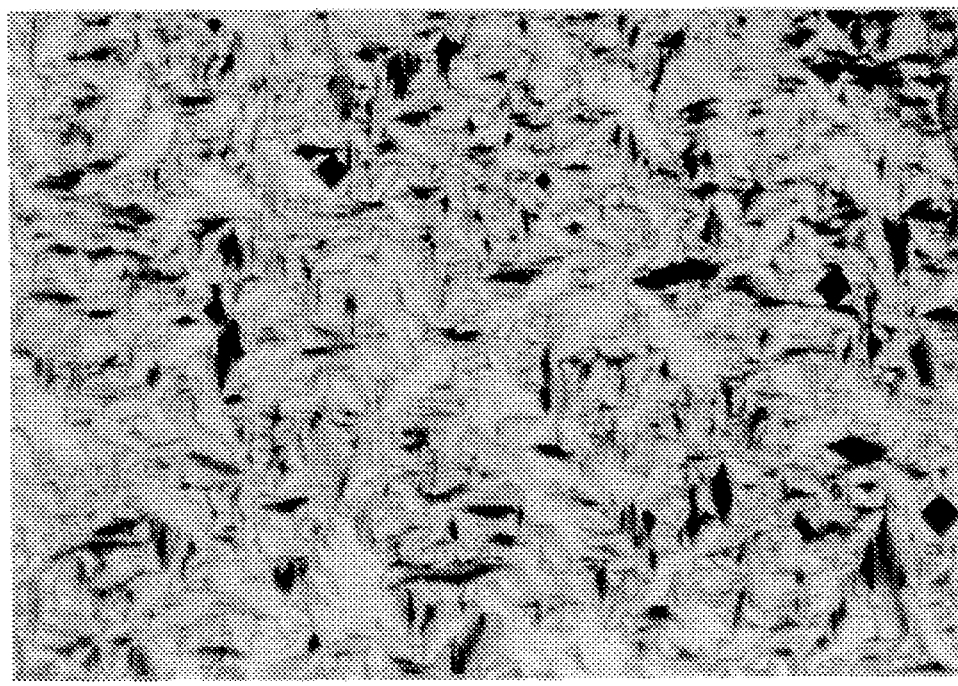
Figure 38C:
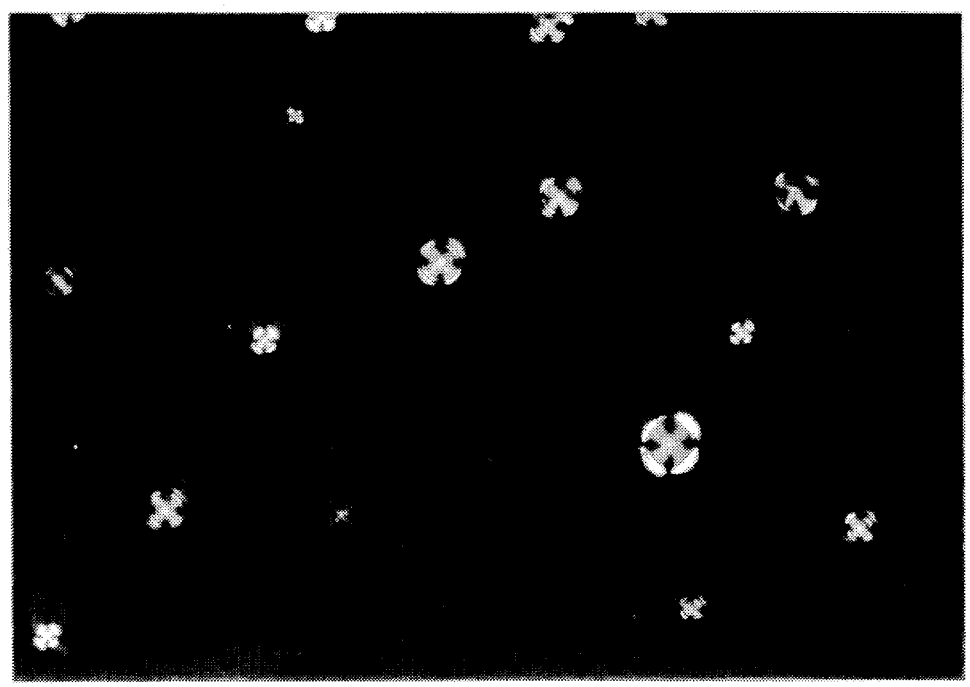

FIG. 12 presents the DSC heating and cooling traces of monomer I-23. FIG. 38(A) is an optical polarizing micrograph of monomer I-23 taken at 98.4° C. (400×). When the temperature decreases to 71.2° C., the size of the texture grows and the optical polarizing micrograph, FIG. 38(B), displays a fan-like texture of a cholesteric mesophase. As the temperature further drops to 58.2° C., the optical polarizing micrograph of the monomer I-23 [FIG. 38(C)] displays bands drops texture, which may be a chiral smectic C phase. Monomer I-23 crystallizes at 5.5° C. on the cooling scan of DSC.

Figure 13:
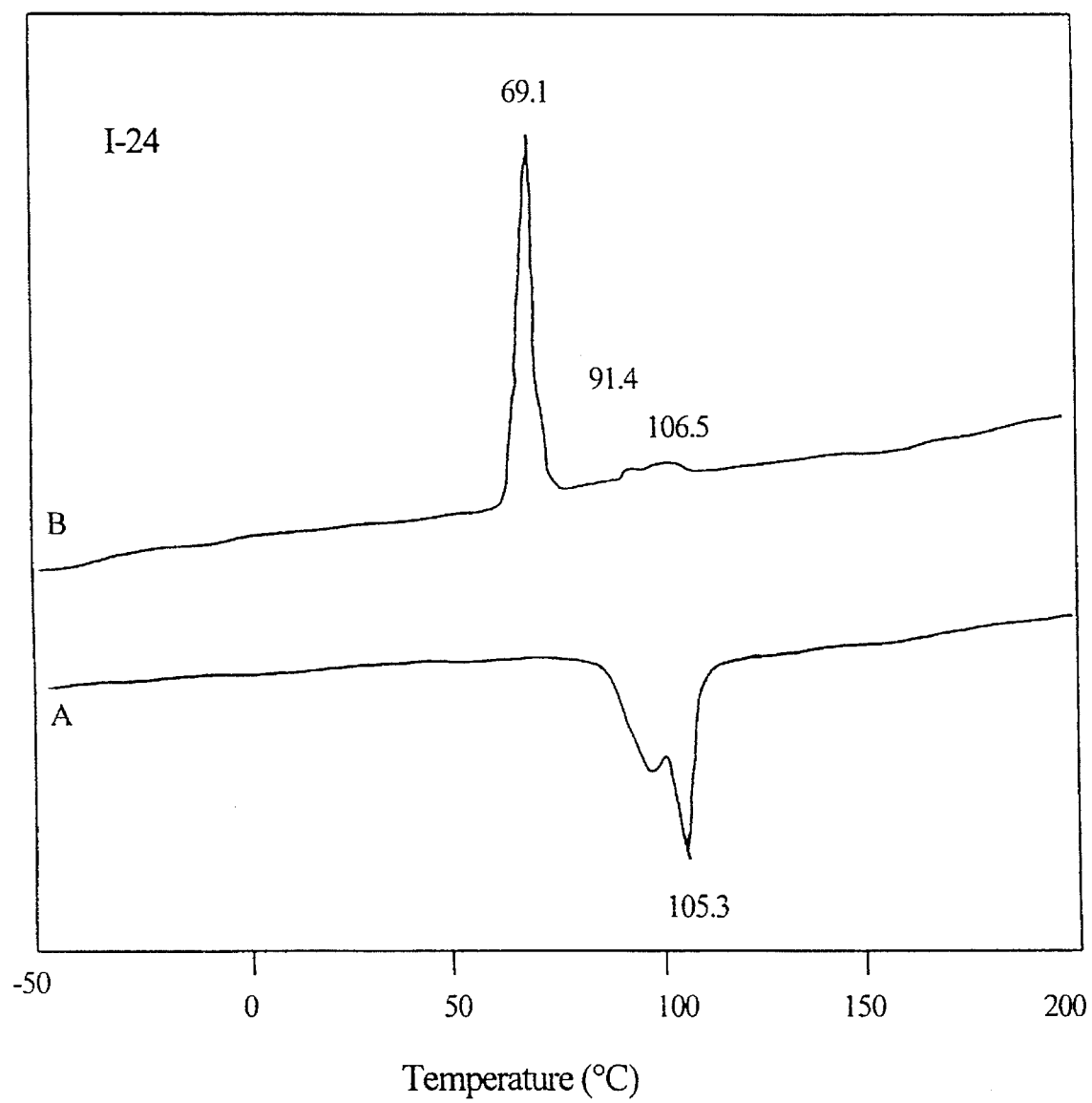
FIG. 13 is a Differential Scanning Calorimeter (DSC) thermogram (10° C./min) for monomer I-24: A) heating scan; B) cooling scan.
Figure 39:
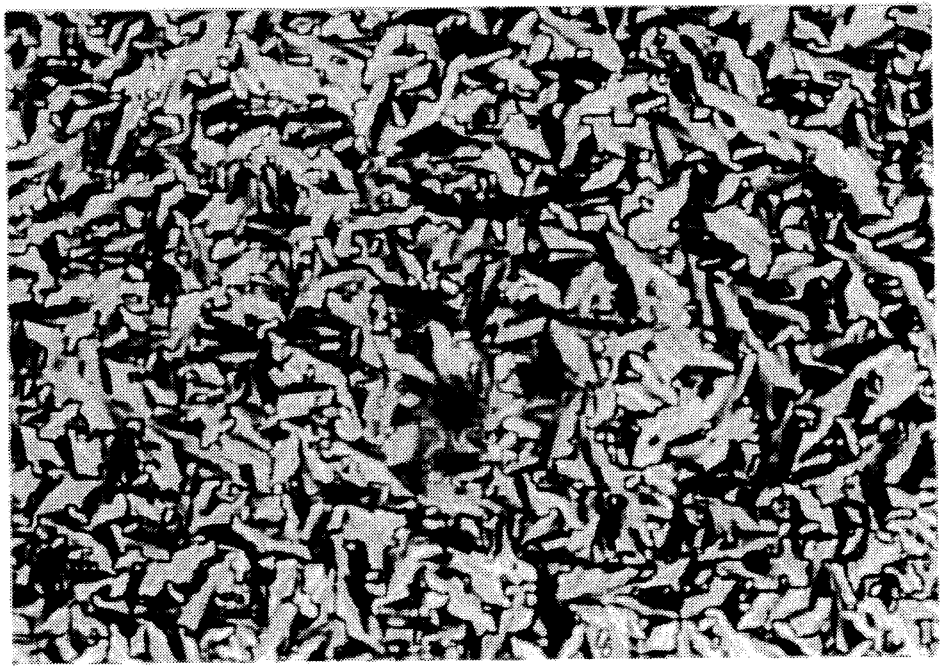
FIGS. 39(A), (B), (C), (D) are typical optical polarizing micrographs (magnification 400×) of monomer I-24: (A) cholesteric fan like texture obtained at 106.5° C.; (B) the texture obtained at 91.5° C.; (C) crystalline texture obtained at 69.1° C.
Figure 39:
Figure 39:
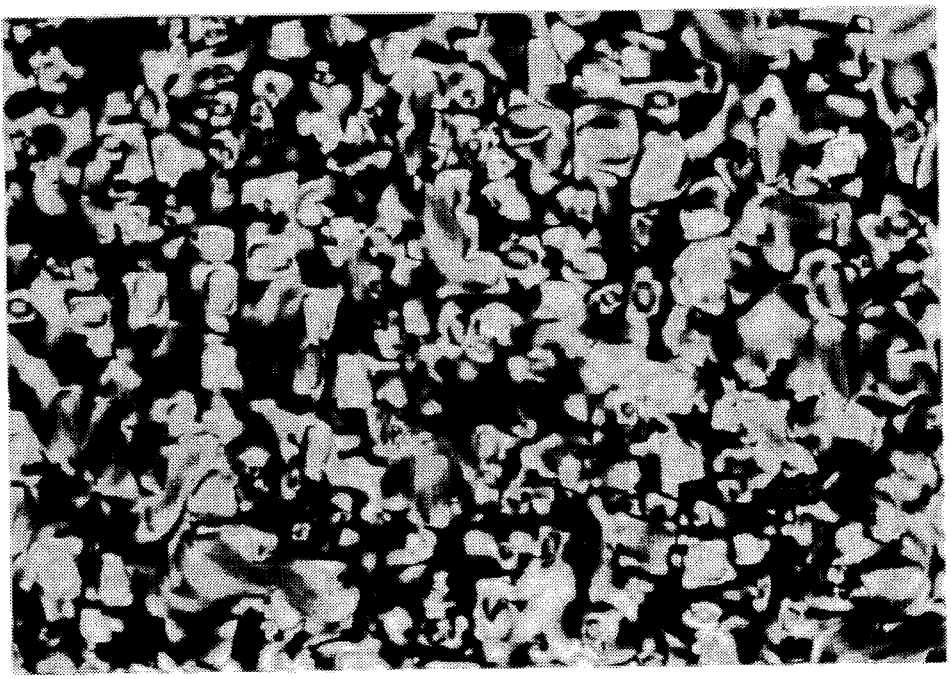
Figure 39:

FIG. 13 presents the DSC heating and cooling traces of monomer I-24. The optical polarizing micrograph of monomer I-24 taken at 106.5° C. displays a fan-like texture of a cholesteric mesophase [FIG. 39(A)]. When the temperature decreases, the color thereof gradually turns to purple [FIG. 39(B)]. When the temperature decreases to 91.1° C., the optical polarizing micrograph of monomer I-24 [FIG. 39(C)] displays a texture which may be a chiral smectic C phase. As the temperature further drops to 69.1° C., the monomer I-24 crystallizes and the optical polarizing micrograph thereof is shown in FIG. 39(D).

Figure 14:
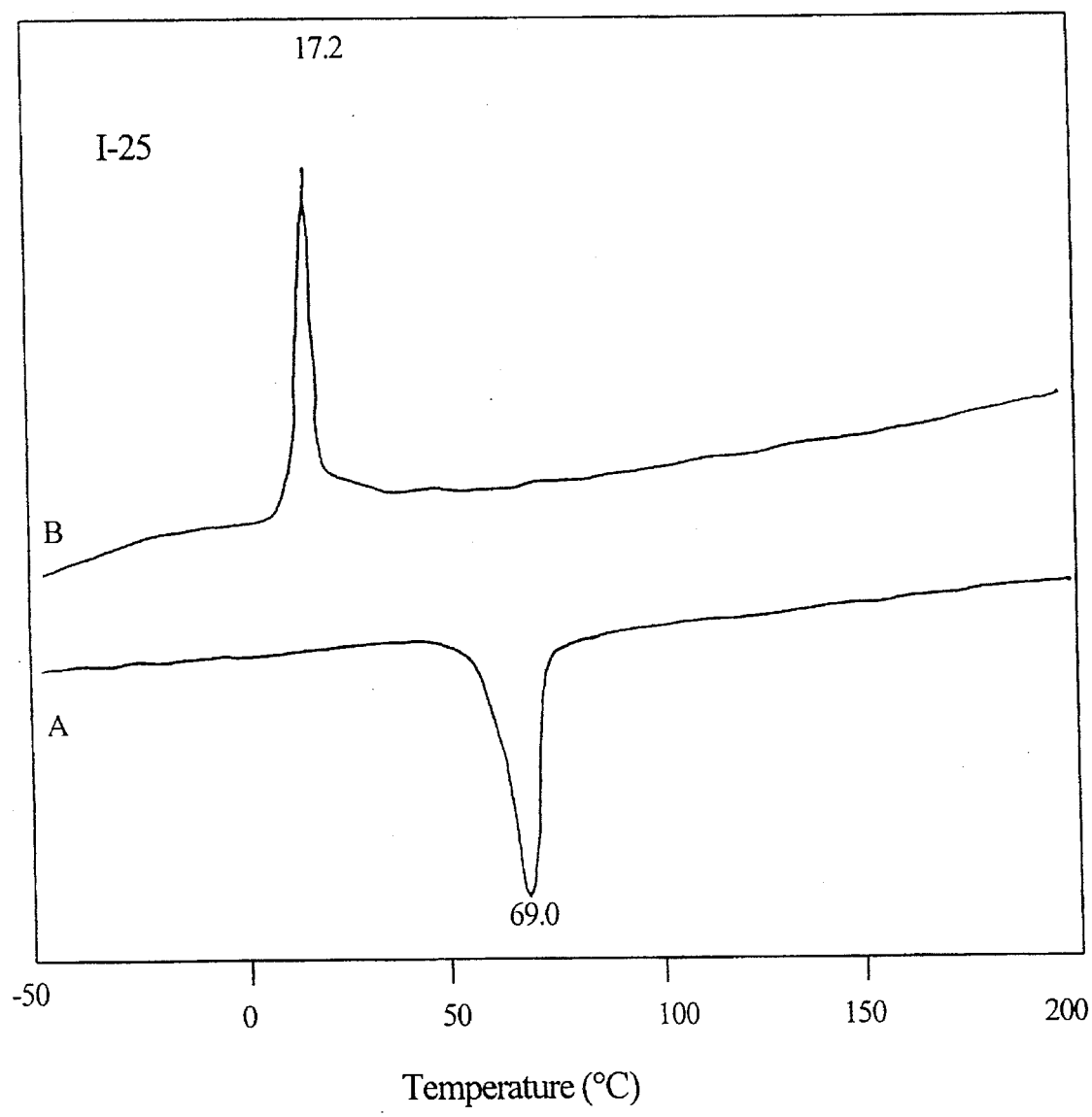
FIG. 14 is a Differential Scanning Calorimeter (DSC) thermogram (10° C./min) for monomer I-25: A) heating scan; B) cooling scan.

FIG. 14 presents the DSC heating and cooling traces of monomer I-25. The optical polarizing microscopy shows that monomer I-25 has no liquid crystalline mesophase but one melting point.

Figure 15:
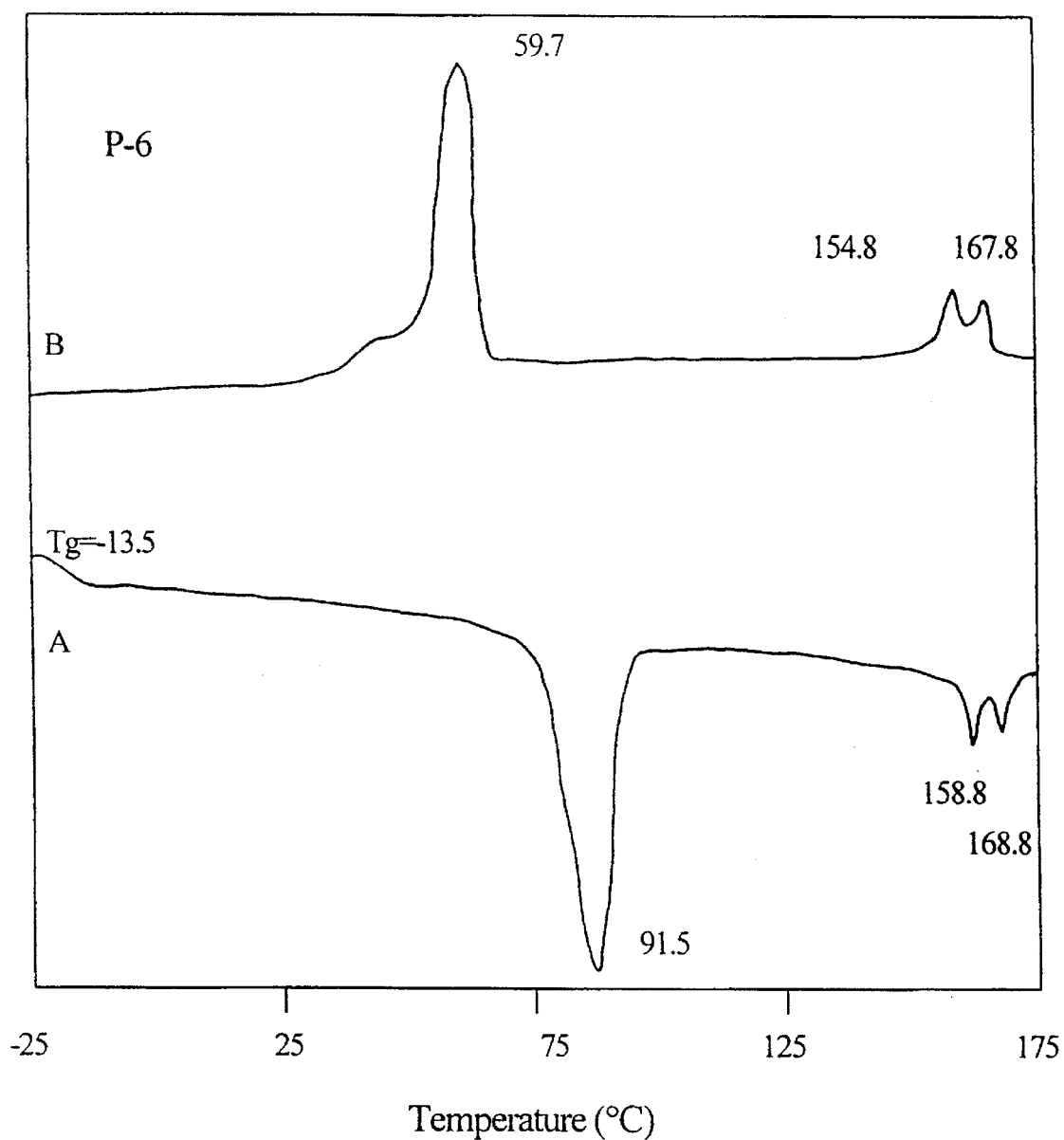
FIG. 15 is a Differential Scanning Calorimeter (DSC) thermogram (10° C./min) for polymer P-6: A) heating scan; B) cooling scan.
Figure 40:
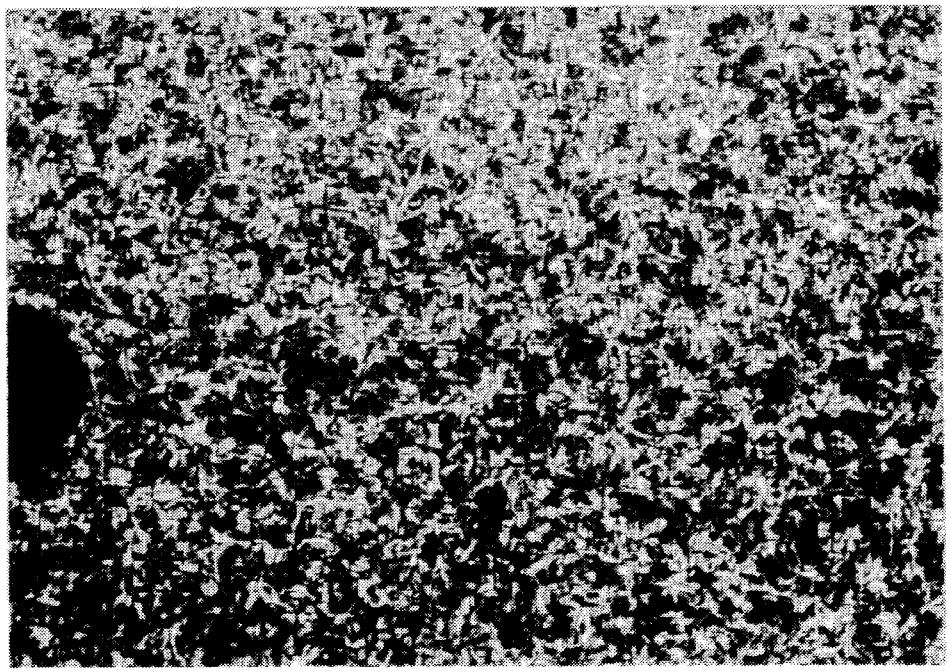
FIGS. 40(A), (B) are typical optical polarizing micrographs (magnification 400×) of polymer P-6: (A) schlieren texture obtained at 167.8° C.; (B) the texture obtained at 154.8° C.
Figure 40:
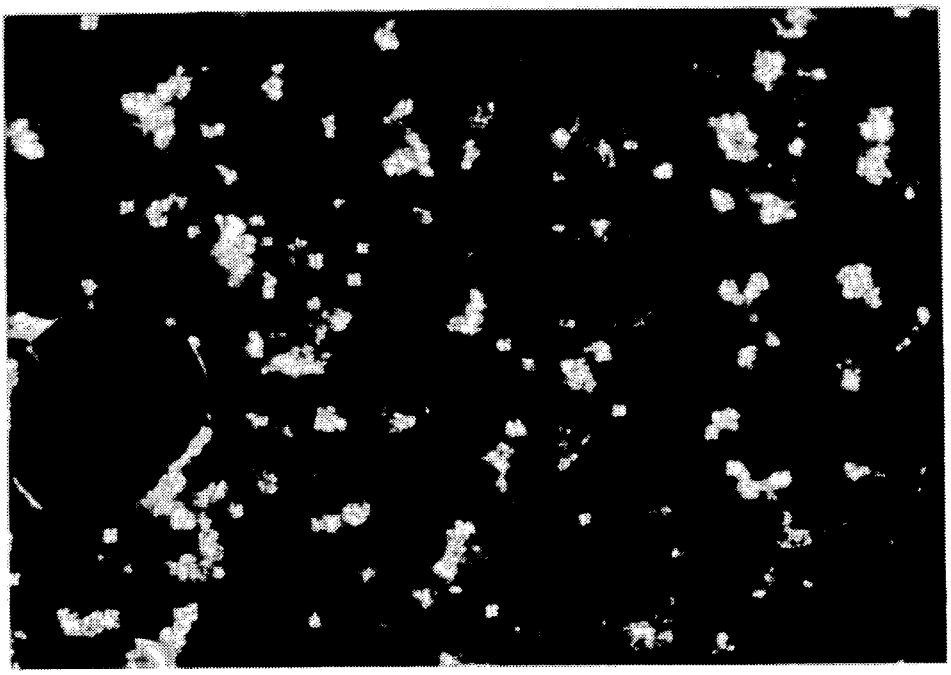

FIG. 15 presents the DSC heating and cooling traces of polymer P-6, which shows polymer P-6 has a glass transition temperature (Tg) of −13.5° C. From FIG. 15 and with the help from optical polarizing microscopy, the mesophases of polymer P-6 can be identified. The optical polarizing micrograph of polymer P-6 taken 167.8° C. displays a schlieren texture of a cholesteric mesophase [FIG. 40(A)]. When the temperature decreases to 154.8° C., the optical polarizing micrograph [FIG. 40(B)] displays a substantially homeotropi texture having a few bi-refractions, which may be a cholesteric mesophase. As the temperature further drops to 59.7° C., the polymer P-6 undergoes side chain crystallization.

Figure 16:
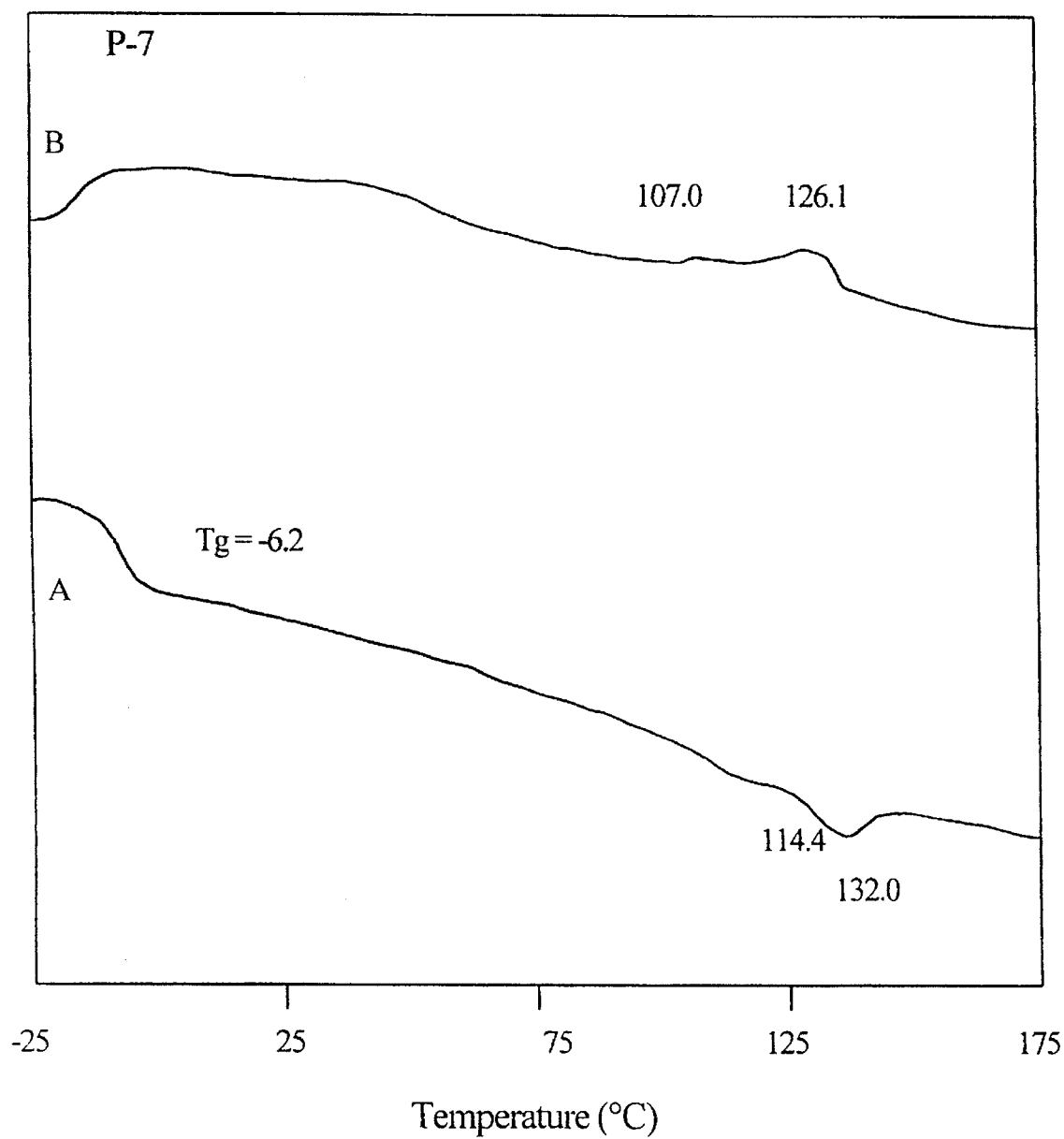
FIG. 16 is a Differential Scanning Calorimeter (DSC) thermogram (10° C./min) for polymer P-7: A) heating scan; B) cooling scan.
Figure 41:
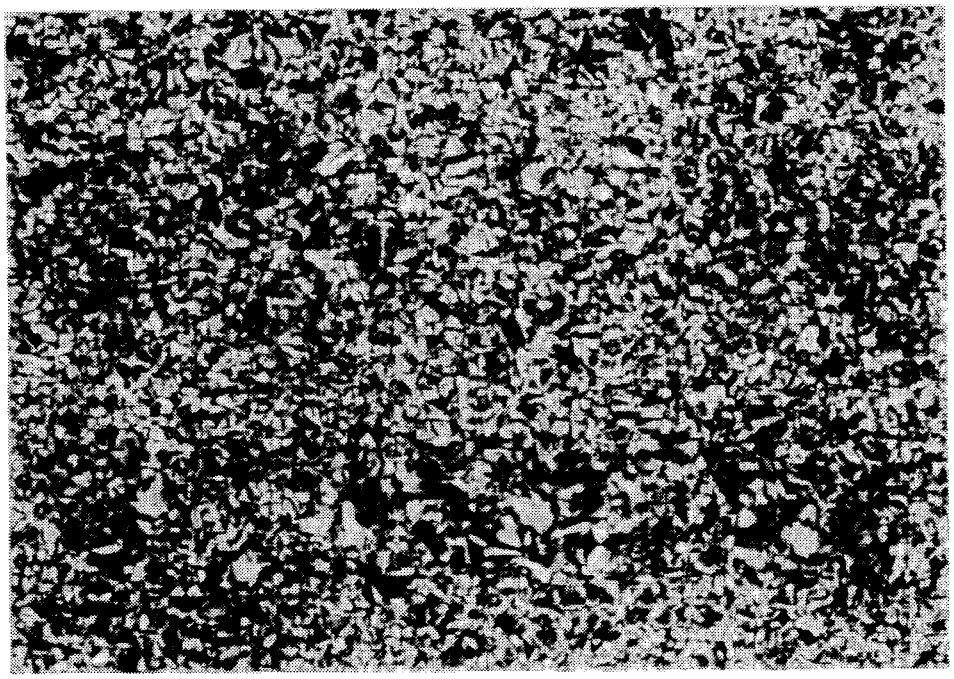
FIGS. 41(A), (B) are typical optical polarizing micrographs (magnification 400×) of polymer P-7: (A) focal-conic fan texture obtained at 126.1° C.; (B) schlieren texture obtained at 107.0° C.
Figure 41:
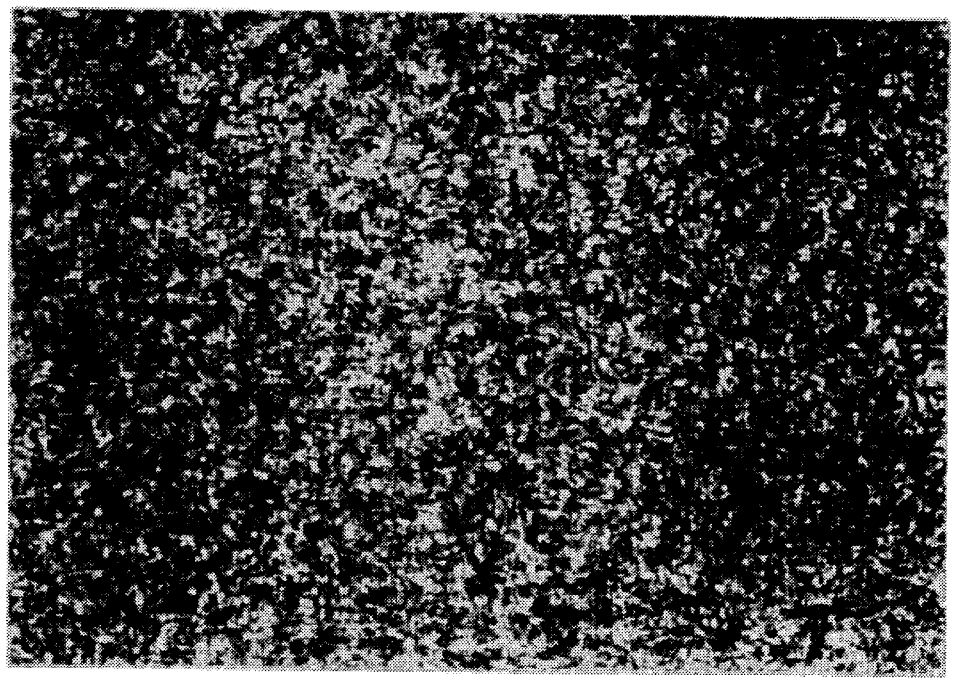

FIG. 16 presents the DSC heating and cooling traces of polymer P-7, which show that polymer P-7 has a glass transition temperature (Tg) of −6.2° C. The optical polarizing micrograph of polymer P-7 taken 126.1° C. displays a focal-conic fan texture of a smectic A phase [FIG. 41(A)]. When the temperature decreases to 107.0° C., the optical polarizing micrograph [FIG. 41(B)] displays a schlieren texture which may be a chiral smectic C phase. As the temperature further drops to room temperature, the liquid crystal line phase of polymer P-7 remains unchanged.

Figure 17:
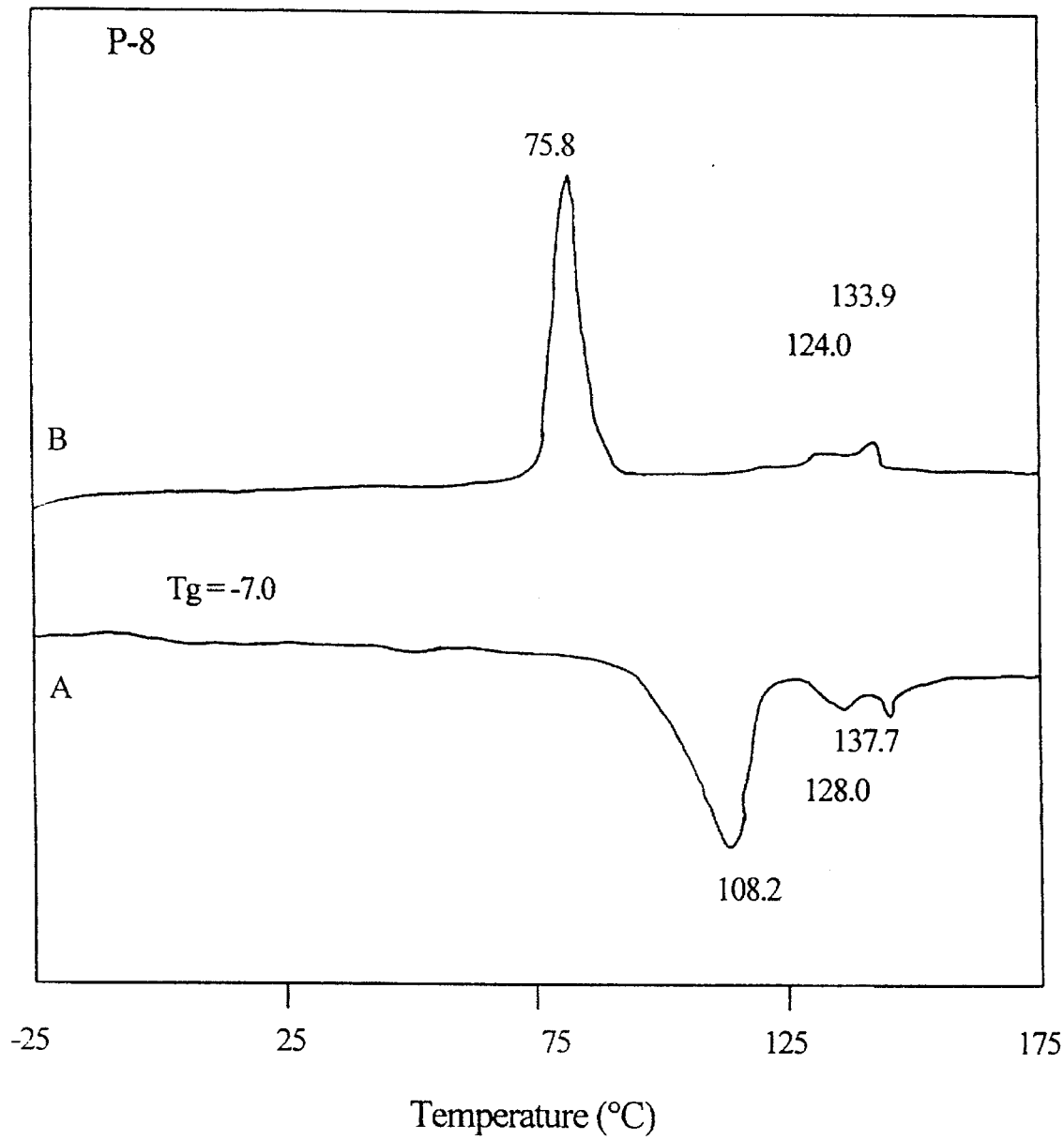
FIG. 17 is a Differential Scanning Calorimeter (DSC) thermogram (10° C./min) for polymer P-8: A) heating scan; B) cooling scan.
Figure 42:
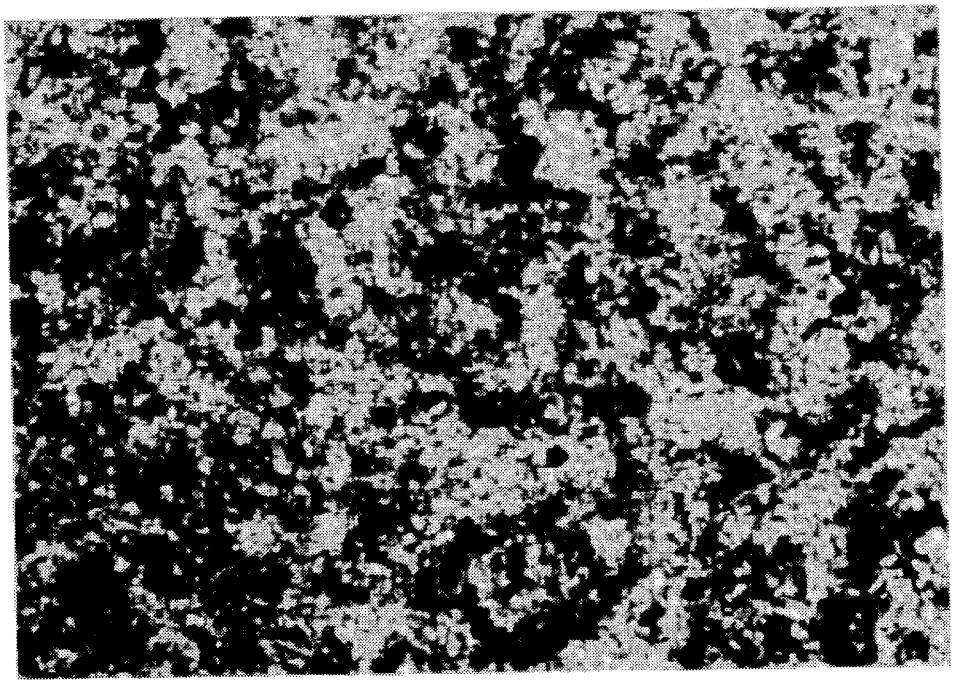
FIGS. 42(A), (B) are typical optical polarizing micrographs (magnification 400×) of polymer P-8: (A) the texture obtained at 133.9° C.; (B) the texture obtained at 124.0° C.
Figure 42:

FIG. 17 presents the DSC heating and cooling traces of polymer P-8, which show that polymer P-8 has a glass transition temperature (Tg) of −7.0° C. The optical polarizing micrograph of polymer P-8 taken 133.9° C. displays a partially homeotropi texture [FIG. 42(A)]. When the temperature decreases to 124.0° C., the optical polarizing micrograph [FIG. 42(B)] displays a texture which can not be identified what type of mesophase it belongs to. As the temperature further drops to 75.8° C., the polymer P-8 undergoes side chain crystallization.

Figure 18:
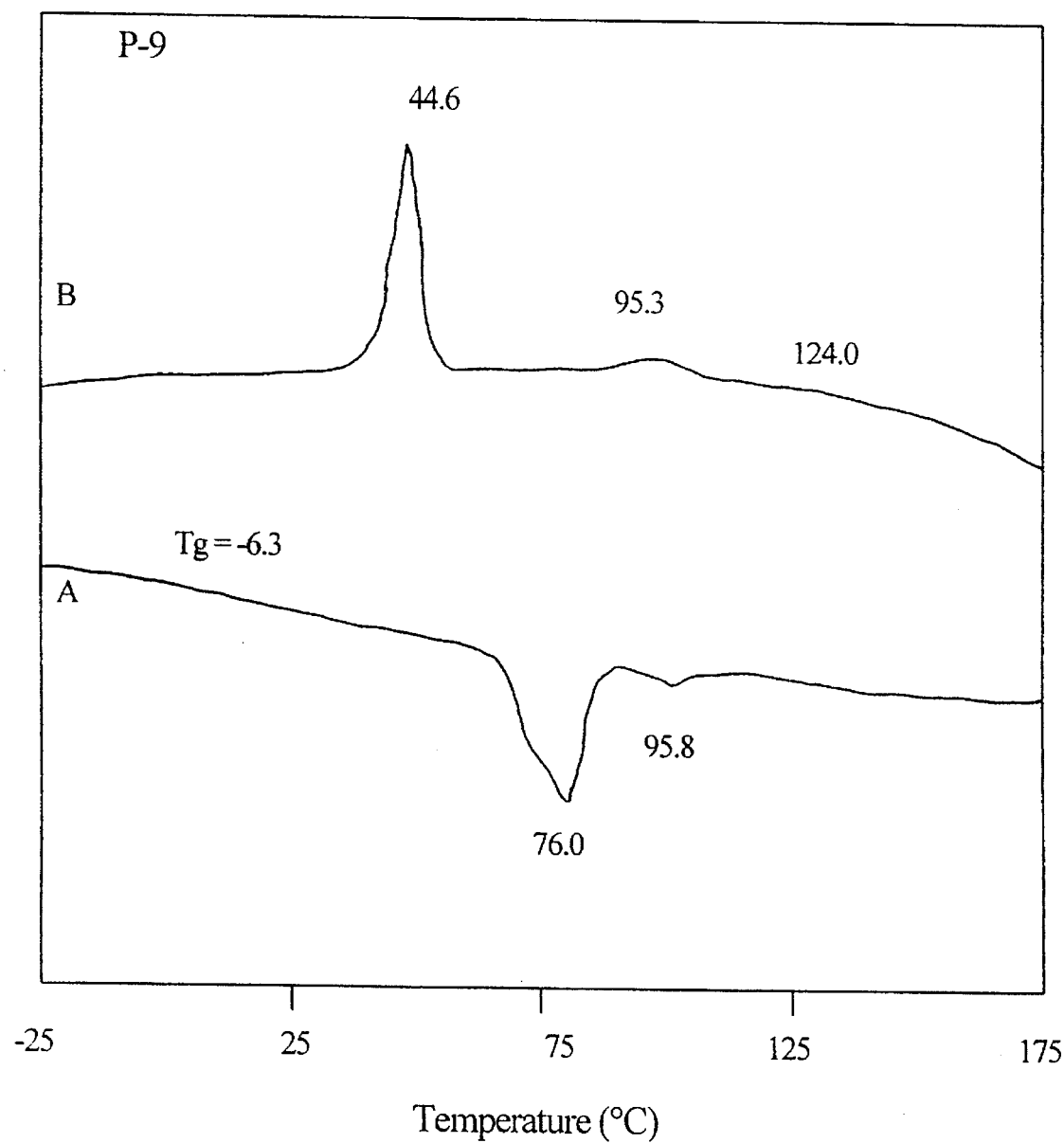
FIG. 18 is a Differential Scanning Calorimeter (DSC) thermogram (10° C./min) for polymer P-9: A) heating scan; B) cooling scan.
Figure 43:
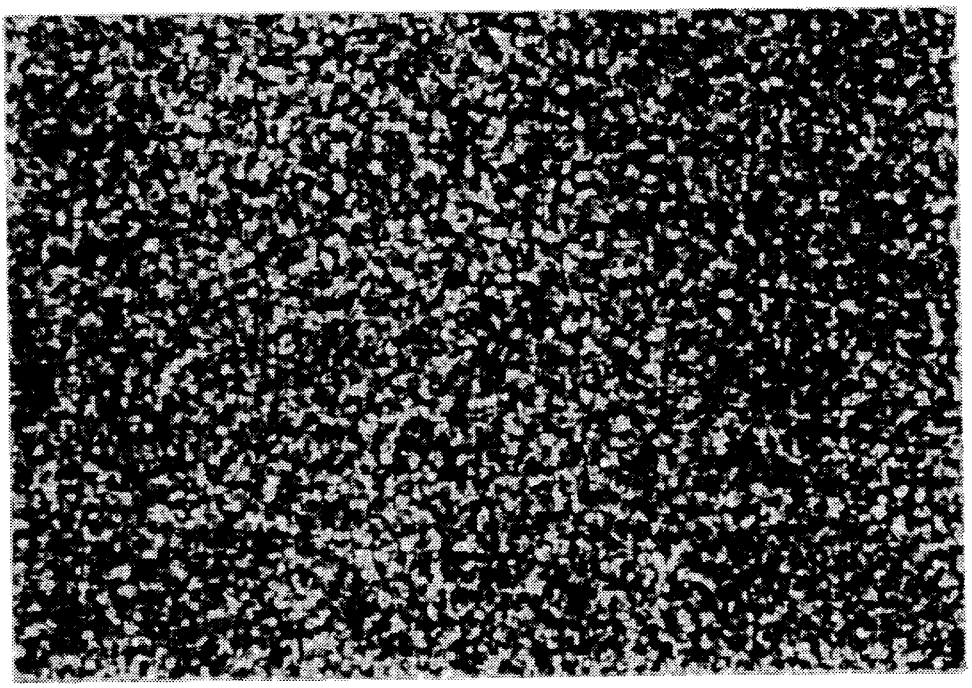
FIG. 43 is typical optical polarizing micrograph (magnification 400×) of polymer P-9: the texture obtained at 95.3° C.
Figure 44:
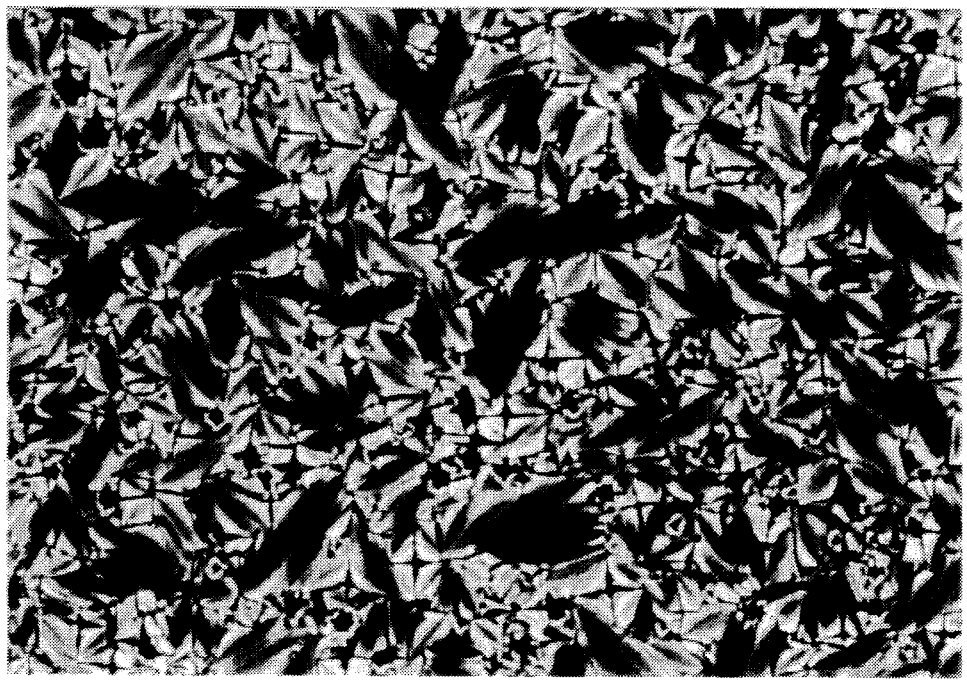
FIGS. 44(A), (B) are optical polarizing micrographs displayed by monomer I-35: (A) the focal-conic fan texture of smectic A obtained at 106° C.; (B) the broken fan texture of chiral smectic C obtained at 78° C.
Figure 44:
Figure 45:
FIGS. 45(A), (B) are optical polarizing micrographs displayed by monomer I-36: (A) the focal-conic fan texture of smectic A obtained at 125° C.; (B) the broken fan texture of chiral smectic C obtained at 30° C.
Figure 45:
Figure 46:
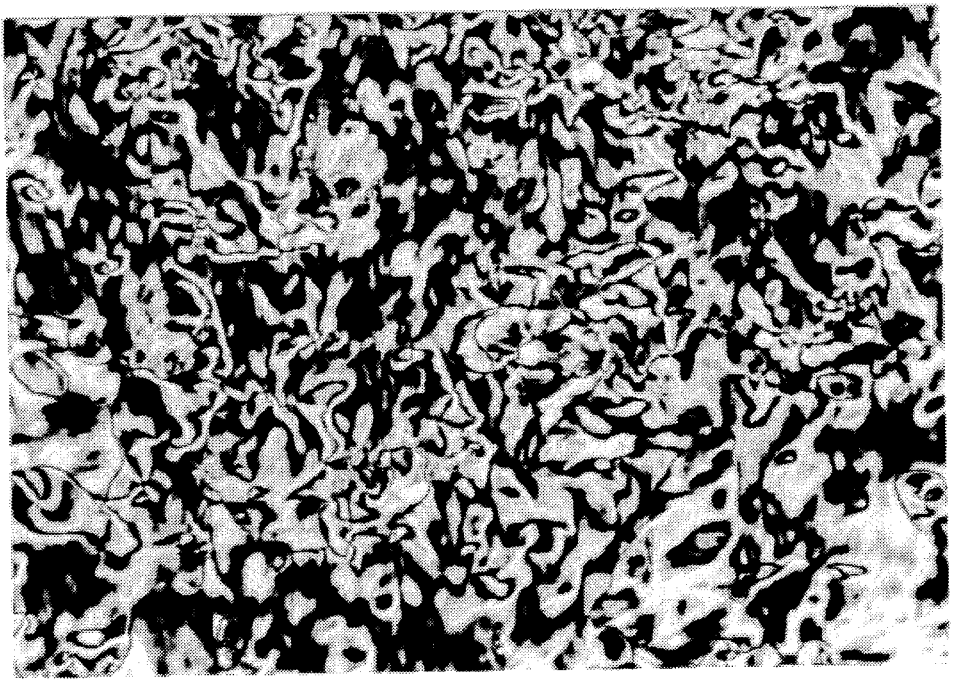
FIGS. 46(A), (B) are optical polarizing micrographs displayed by monomer I-37: (A) the schlieren texture of chiral smectic C obtained at 34° C.; (B) another texture of chiral smectic C obtained at 34° C.
Figure 46:
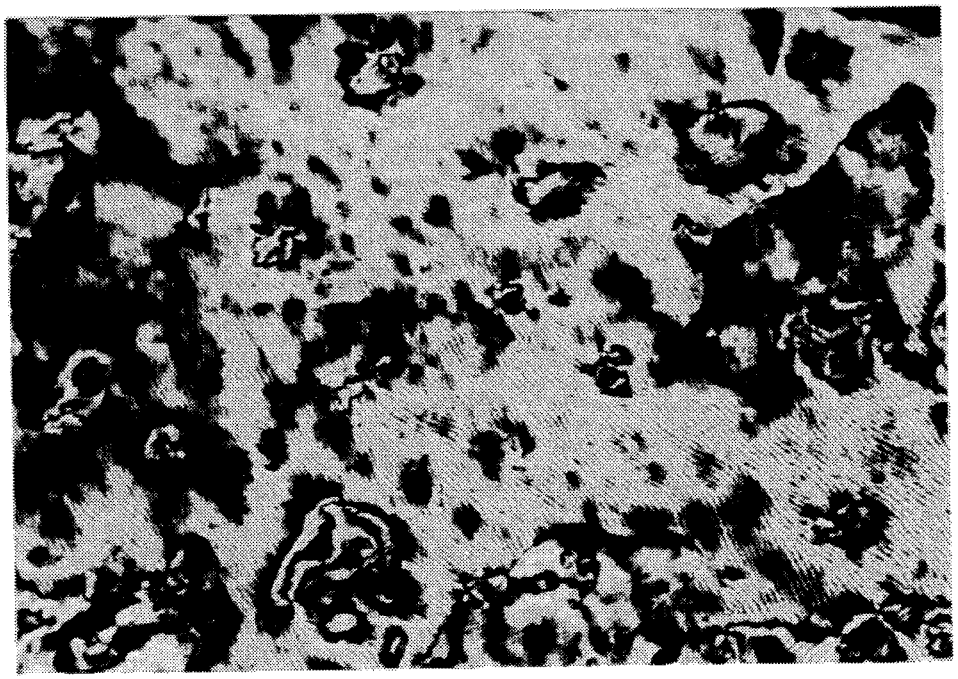
Figure 47:
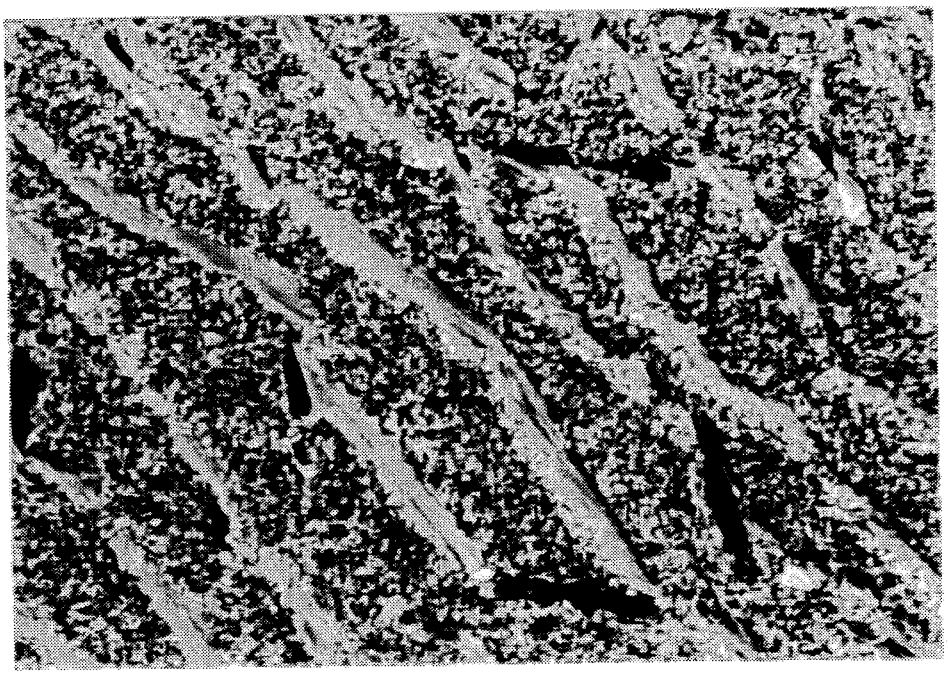
FIGS. 47(A), (B) are optical polarizing micrographs displayed by polymer P-10: (A) the focal-conic fan texture of smectic A obtained at 221° C.; (B) the broken fan texture of Chiral smectic C obtained at 178° C.
Figure 47:
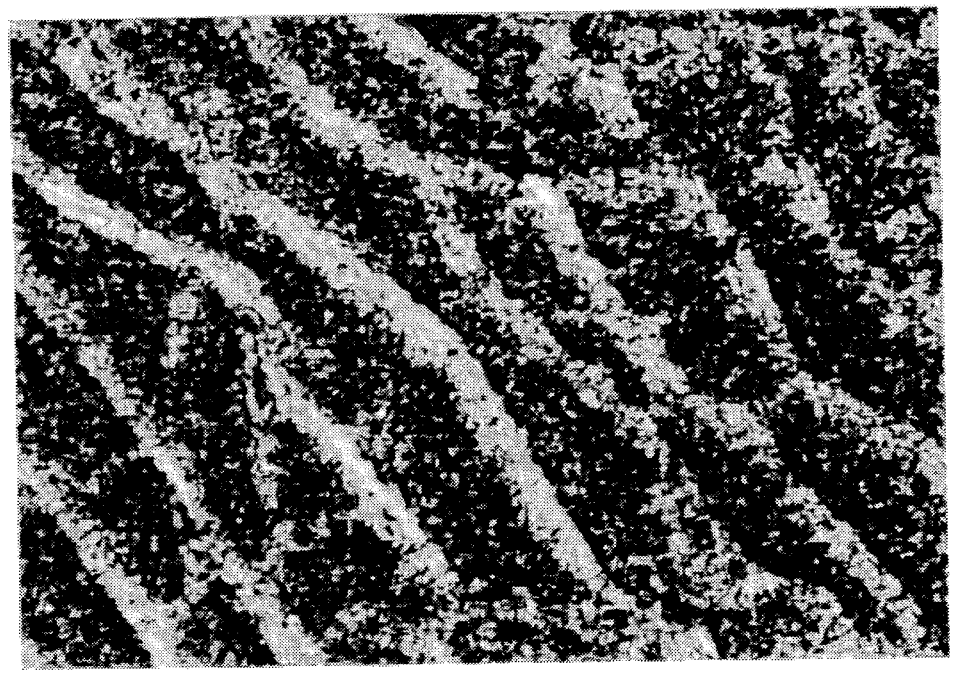
Figure 48:
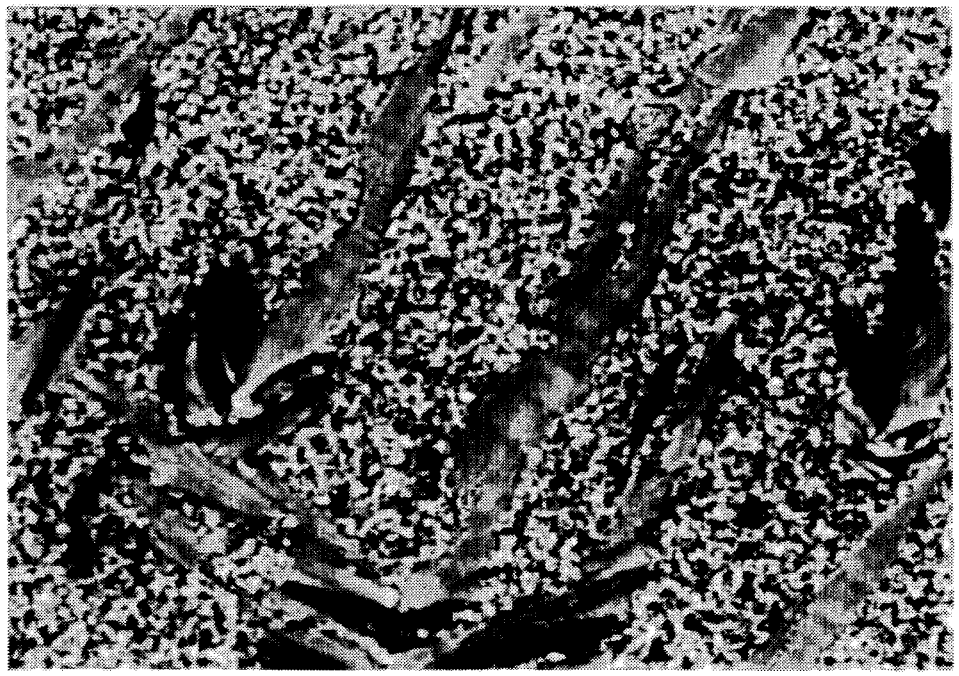
FIGS. 48(A), (B) are optical polarizing micrographs displayed by polymer P-11: (A) the broken fan texture of chiral smectic C obtained at 200° C.; (B) the broken fan texture of chiral smectic C obtained at 200° C.
Figure 48:
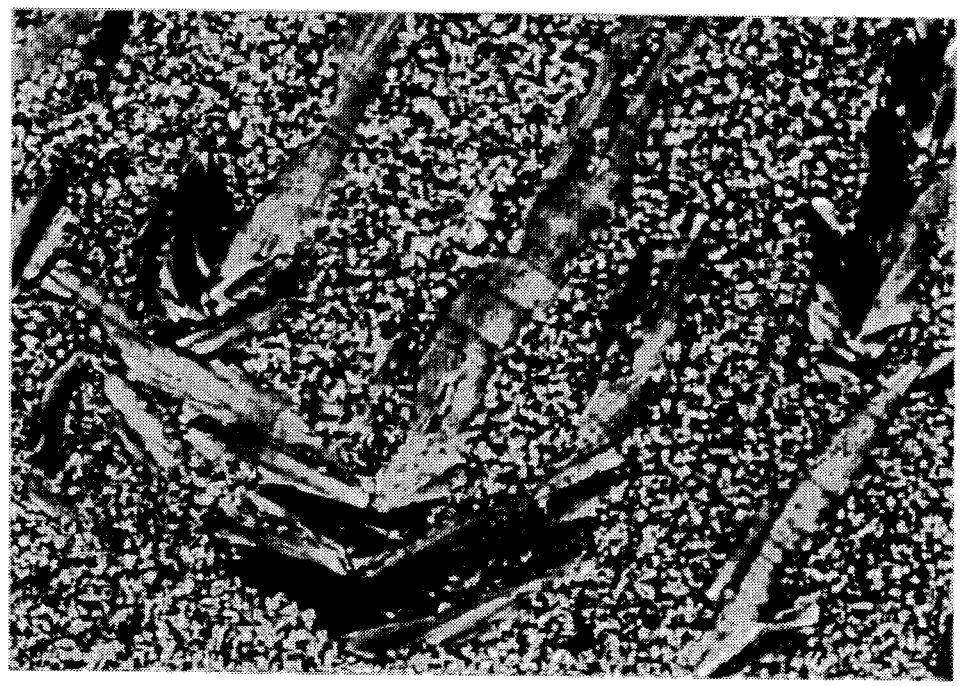
Figure 49:
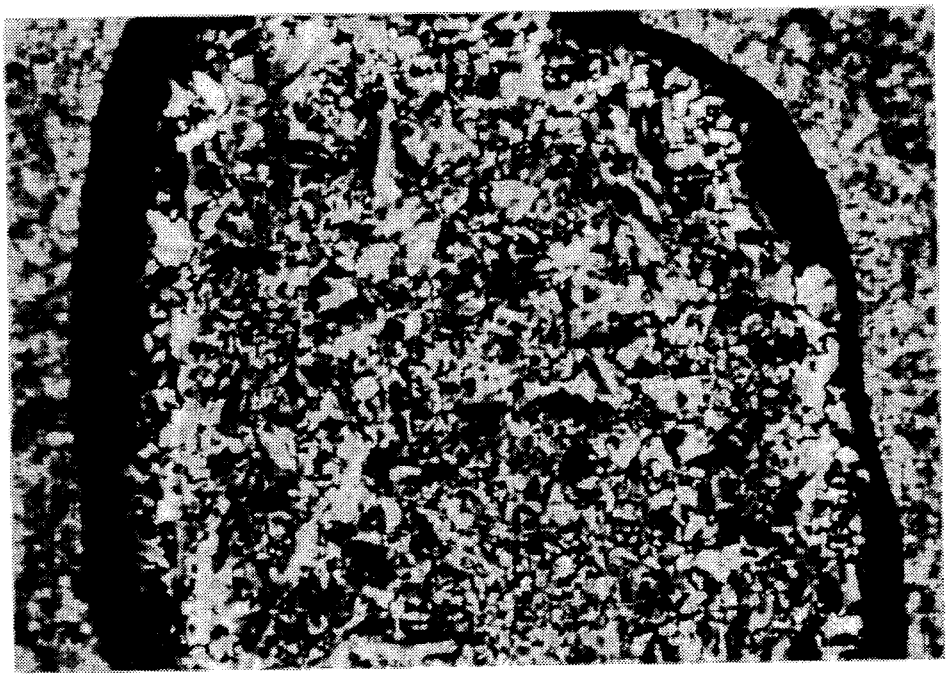
FIGS. 49(A), (B) are optical polarizing micrographs displayed by polymer P-12: (A) the focal-conic fan texture of smectic A obtained at 180° C.; (B) the broken fan texture of chiral smectic C obtained at 101° C.
Figure 49:

FIG. 18 presents the DSC heating and cooling traces of polymer P-9. The optical polarizing micrograph of polymer P-9 taken 95.3° C. displays a texture which should be a smectic mesophase (FIG. 43). As the temperature further drops to 44.6° C., the polymer P-9 undergoes side chain crystallization.

Table 6 summarizes the thermal transitions and thermodynamic parameters of the synthesized monomers I-22 to I-25. Table 7 summarizes the thermal transitions and thermodynamic parameters of the synthesized polymers P-6 to P-9

TABLE 6

Phase transitions and phase transition enthalpies for monomers I-22–I-25

Phase transitions, °C. (corresponding enthalpy changes, Kcal/mol)

| Monomer | $X_1$ | $X_2$ | heating<br>cooling |
|---|---|---|---|
| I-22 | H | H | k 83.9 (6.22) $S_A$ 143.7 (0.802) I |
| I-23 | H | Cl | I 140.0 (0.502) $S_A$ 52.7 (5.29) K<br>k 59.7 (7.08) $S_A$ 99.8 (0.153) I |
| I-24 | Cl | H | I 98.4 (0.226) $S_A$ 58.2 (0.101) $S_c^*$ 5.5 (2.93) K<br>k 105.3 (5.97) I |
| I-25 | Cl | Cl | I 106.5 (0.393) $S_A$ 91.4 (—)$^b$ $S_c^*$ 69.1 (4.51) K<br>k 69.0 (6.29) I<br>I 17.2 (4.94) K |

$^b$Enthalpy is very small.
K: crystal
$S_A$: smectic A phase
$S_c^*$ : chiral smectic C phase
I: isotropic

TABLE 7

Phase transitions and phase transition enthalpies for polymers P-6–P-9

Phase transitions, °C. (corresponding enthalpy changes, Kcal/mru$^c$)

| Polymer | $X_1$ | $X_2$ | heating<br>cooling |
|---|---|---|---|
| P-6 | H | H | G –13.5 K 91.5 (5.91) $S_c^*$ 158.8 (—)$^b$ N* 168.8 (0.991) I<br>I 167.8 (0.984) N* 154.8 (—)$^b$ $S_c^*$ 59.7 (5.27) K |
| P-7 | H | Cl | G –6.2 $S_c^*$ 114.4 (0.06) $S_A$ 132.0 (0.298) I<br>I 126.1 (0.368) $S_A$ 107.0 (0.03) $S_c^*$ |
| P-8 | Cl | H | G –7.0 K 108.2 (5.73) S 128.0 (—)$^b$ $S_A$ 137.7 (0.624) I<br>I 133.9 (0.536) $S_A$ 124.0 (—)$^b$ S 75.8 (5.30) K |
| P-9 | Cl | Cl | G –6.3 K 76.0 (3.21) S 95.8 (0.261) I<br>I 95.3 (0.328) S 44.6 (3.33) K |

$^b$Enthalpy is overlapped.
$^c$mru = mole repeating unit
G : glass transition temperature

PREPARATION EXAMPLES 26–27

Synthesis of 2-(2-Allyloxy)ethoxy ethanol (I-26)
2-[2-(2-Allyloxy)ethoxy]ethoxy ethanol (I-27)

The compounds I-26 and I-27 were synthesized by the same method. The synthesis of compound I-26 is described below as an example. In a 500 ml flask, 42.4 g (0.4 mole) diethylene glycol, 16 g (0.4 mole) NaOH and 16 ml water were mixed and heated while stirring until a clear solution was obtained. To the clear solution, 12.1 g (0.1 mole) allylbromide was added dropwise and refluxed at 100° C. for 24 hours, which was then cooled to room temperature. The cooled reaction mixture was diluted with a suitable amount of water, extracted with ethyl ether, the organic layer thereof was removed and dried over anhydrous $MgSO_4$, and concentrated to obtain a light orange liquid. The resulting light orange liquid was dried under vacuum and distilled at a pressure of 2 mmHg and 80°–82° C. to yield a colorless liquid. Yield: I -26: 55.7%; I-27: 63.4%. $^1$H-NMR:
I-26
$^1$H-NMR(CDCl$_3$, TMS, δ ppm): 3.41–3.56(m,8H,—(O—CH$_2$—CH$_2$)$_2$—),3.87(d,2H, =CH—CH$_2$—),5.06(m,2H,H$_2$C=CH—),5.74(m,1H,H$_2$C=CH—).
I-27
$^1$H-NMR(CDCl$_3$, TMS, δ ppm): 3.40–3.54(m,12H,—(O—CH$_2$—CH$_2$)$_3$—),3.83(d,2H, =CH—CH$_2$—),5.06(m,2H,H$_2$C=CH—),5.72(m,1H,H$_2$C=CH—).

PREPARATION EXAMPLES 28–30

Synthesis of

2-Allyloxyethyl tosylate (I-28)
2-(2-Allyloxy)ethoxyethyl tosylate (I-29)
2-[2-(2-Allyloxy)ethoxy]ethoxyethyl tosylate (I-30)

To 60 ml pyridine. In a flask, 15.7 g (0.082 mole) p-tolysufonyl chloride was added while stirring, and 0.075 mole of 2-allyloxyethanol, compound I-26 or compound I-27 was added slowly under nitrogen and at a temperature which was maintained at 0° C. The reaction was carried out at 0° C. for 20 hours and 70 ml ice water was poured into the reaction mixture, which was then extracted with ethyl ether. The ethyl ether layer was collected, washed with 6N HCl aqueous solution, dried over anhydrous $MgSO_4$, filtered and concentrated to yield a transparent product I-28, I-29 or I-30. Yield: I-28: 73.5; I-29: 63.6%; I-30: 71.5%. $^1$H-NMR:
I-28
$^1$H-NMR(CDCl$_3$, TMS, δ ppm): 2.45(s,3H,—CH$_3$),3.61–4.18(m,6H,—O—CH$_2$—CH$_2$—O—,=CH—CH$_2$—O—),5.18(m,2H,H$_2$C=CH—),5.82(m, 1H,H$_2$C=CH—),7.33–7.81(q,4H, aromatic H).
I-29

$^1$H-NMR (CDCl$_3$, TMS, δ ppm): 2.39(s,3H,—CH$_3$),3.46–4.12(m,10H,—(O—CH$_2$—CH$_2$)$_2$—,=CH—CH$_2$—),5.16(m,2H,H$_2$C=CH—),5.82(m,1H, H$_2$C=CH—),7.28–7.75(q,4H, aromatic H).

I-30

$^1$H-NMR (CDCl$_3$, TMS, δ ppm): 2.44(s,3H,—CH$_3$),3.58–4.17(m,14H,—(O—CH$_2$—CH$_2$)$_2$—,=CH—CH$_2$),5.19(m,2H,H$_2$C=CH—),5.89(m,1H, H$_2$C=CH—),7.33–7.80(q,4H, aromatic H).

PREPARATION EXAMPLES 31–33

4'-(2-Allyloxyethoxy) biphenyl-4-carboxylic acid (I-31)

4'-[2-(2-Allyloxyethoxy) ethoxy]biphenyl-4-carboxylic acid (I-32)

4'-{2-[2-(2-Allyloxyethoxy) ethoxy]ethoxy}biphenyl-4-carboxylic acid (I-33)

6 g 4-hydroxyl benzoic acid, 4 equivalent mole KOH, and 1.2 equivalent mole KI were dissolved in 150 ml 90% ethanol, and refluxed for one hour. 1.2 equivalent mole of compound I-28 (Preparation Example 31), I-29 (Preparation Example 32) or I-30 (Preparation Example 33) was added slowly, refluxed for 20 hours, and 30 ml of 10% KOH aqueous solution was added followed by additional 2 hours refluxing. The resulting reaction mixture was cooled and concentrated, acidified by 6N HCl aqueous solution to obtained white precipitate. The precipitate was collected by filtration and recrystallized from ethanol to yield compound I-31, I-32 or I-33. Yield: I-31: 75.6; I-32: 83.7; I-33: 79.3.

$^1$H-NMR:

I-31

$^1$H-NMR(CD$_3$COCD$_3$, TMS, δ ppm): 3.82–4.20(m,6H,=CH—CH$_2$—O—,—O—CH$_2$—CH$_2$—O—), 5.30(m,2H, H$_2$C=CH—),5.95(m,1H,H$_2$C=CH—),7.0–7.62(m, 8H, aromatic H).

I-32

$^1$H-NMR(CD$_3$COCD$_3$, TMS, δ ppm): 3.56–4.20(m,10H,=CH—CH$_2$—O—,—(O—CH$_2$—CH$_2$) $_2$,—),5.23(m,2H, H$_2$C=CH—),5.87 (m,1H,H$_2$C=CH—CH$_2$—),7.04–8.08(m,8H, aromatic H).

I-33

$^1$H-NMR(CD$_3$COCD$_3$, TMS, δ ppm): 3.50–4.16 (m,14H, =CH—CH$_2$—O—,—(O—CH$_2$—CH$_2$) $_3$,—),5.11(m,2H, H$_2$C=CH—),5.84(m,1H,H$_2$C=CH—CH$_2$—),7.04–8.08(m,8H, aromatic H).

PREPARATION EXAMPLE 34

Synthesis of (S)-2-methyl-1-butyl 4-hydroxybenzoate (I-34)

In a 10 ml flask equipped with a Dean-Stark trap 0.036 mole 4-hydroxybenzoic acid, 4.76 g (0.054 mole) (S)-2-methyl-1-butanol, 0.2 ml sulfuric acid and 15 ml anhydrous benzene were charged and refluxed for about 15 hours until all the 4-hydroxybenzoic acid was dissolved. The esterification reaction mixture was cooled to room temperature, extracted with ethyl ether, and washed with 5% (w/w) sodium hydrogen carbonate aqueous solution. The ethyl ether layer was collected, concentrated, and purified with column chromatography (ethyl acetate/n-hexane) to obtained light yellow solid. Yield: I-34: 93%.

$[\alpha]_d^{25}$=+5.50 (c=0.03 g/dl, chloroform)

$^1$H-NMR(CDCl$_3$, TMS, δ ppm):0.80–1.10 (m,6H,—CH$_3$), 1.20–1.58(m,2H,—CH$_2$—),1.78–1.91(m,1H,—CH—), 4.14(q,4H,—COOCH$_2$),6.9–7.9(m,4H, aromatic H)

PREPARATION EXAMPLES 35–37

Synthesis of 4-(S)-2-methyl-1-butyl [4-(2-allyloxyethoxy) biphenyl-4'-carbonyloxy]benzoate (I-35)

4-(S)-2-methyl-1-butyl {4-[2-(2-allyloxyethoxy) ethoxy]biphenyl-4'-carbonyloxy}benzoate (I-36)

4-(S)-2-methyl-a-butyl{4-[2-[2-(2-allyloxyethoxy) ethoxy]ethoxy]biphenyl-4'-carbonyloxy}benzoate (I-37)

To 0.0045 mole compound I-31 (Preparation Example 35), I-32 (Preparation Example 36) or I-33 (Preparation Example 37) dissolved in 10 ml dichloromethane in a 150 ml flask, several drops of dimethylformamide and 4 ml thionylchloride were added and stirred to obtain a transparent solution. The residual thionylchloride and solvent were distilled off from the solution to form a yellow oily acyl chloride. 20 ml dichloromethane was added to dissolve yellow oily acyl chloride. In a 250 ml flask 0.0055 mole compound I-34, 0.67 g DMAP [4-(dimethylamino)pyridine] and 30 ml anhydrous dichloromethane were mixed and stirred in an ice water bath of 0° C. The yellow oily acyl chloride/dichloromethane solution was then added to the mixture in the 250 ml flask dropwise, stirred at room temperature for another 12 hours after the addition being completed, and the residual solvent was distilled off. The resulting product was dissolved in dichloromethane and purified with column chromatography (ethyl ether/n-hexane as eluent) to yield white solid. The yield, optical rotation and $^1$H-NMR of the synthesized monomers I-35 to I-37 are listed in Table 8.

TABLE 8

Characterization of Monomers I-35~I-37

H$_2$C=CH—CH$_2$–(O—CH$_2$—CH$_2$)$_{\overline{n}}$O—⟨biphenyl⟩—C(=O)—O—⟨phenyl⟩—C(=O)—O—CH$_2$—CH(CH$_3$)—C$_2$H$_5$ (*)

| Monomer | Yield (%) | $[\alpha]_D^{25}$ | 400 MHz $^1$H-NMR (CDCl$_3$, δ, PPM) |
|---------|-----------|-------------------|--------------------------------------|
| I-35 | 61.8 | +6.81 | 0.95(t; 3H, —CH—CH$_3$), 1.01(d; 3H, —HCCH$_3$—CH$_2$—), 1.21–1.60(m; 2H, —CH$_2$—CH$_3$—), 185(m; 1H, —CHCH$_3$—), 3.78–4.25(m; 8H, —O—CH$_2$—CH$_2$—O—; —CH$_2$—CH= and |

TABLE 8-continued

Characterization of Monomers I-35~I-37

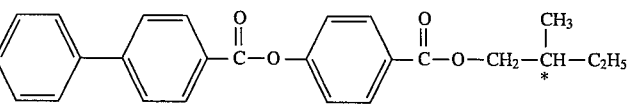

| Monomer | Yield (%) | $[\alpha]_D^{25}$ | 400 MHz $^1$H-NMR (CDCl$_3$, δ, PPM) |
|---|---|---|---|
| I-36 | 52.4 | +7.15 | $-O-CH_2-CHCH_3-$), 5.24(q; 2H, $H_2C=CH-$), 5.93(m; 1H, $H_2C=C\underline{H}-$), 6.98–8.25(m; 12H, aromatic protons). 0.93(t; 3H, $-CH-CH_3$), 1.01(d; 3H, $-HCCH_3-CH_2-$), 1.21–1.61(m; 2H, $-C\underline{H}_2-CH_3-$), 1.85(m; 1H, $-C\underline{H}CH_3-$), 3.59–4.25(m; 12H, $-(-O-C\underline{H}_2-CH_2-)_2-$; $-C\underline{H}_2-CH=$ and $-O-C\underline{H}_2-CHCH_3-$), 5.21(q; 2H, $\underline{H}_2C=CH-$), 5.91(m; 1H, $H_2C=C\underline{H}-$), 6.99–8.29(m; 12H, aromatic protons). |
| I-37 | 61.7 | +7.08 | 0.95(t; 3H, $-CH-CH_3$), 1.01(d; 3H, $-HCC\underline{H}_3-CH_2-$), 1.21–1.59(m; 2H $-C\underline{H}_2-CH_3-$), 1.85(m; 1H, $-CHCH_3-$), 3.58–4.25(m; 16H, $-(-O-C\underline{H}_2-CH_2-)_3-$, $-C\underline{H}_2-CH=$ and $-O-C\underline{H}_2-CHCH_3-$), 5.21(q; 2H, $\underline{H}_2C=CH-$), 5.89(m; 1H, $H_2C=C\underline{H}-$), 6.99–8.25(m; 12H, aromatic protons). |

EXAMPLES 10–12

Synthesis of
Poly[methyl[4-(S)-2-methyl-1-butyl[4-(2-allyloxyethoxy) biphenyl-4'-carbonyloxy]benzoate]siloxane] (P-10)
Poly[methyl[4-(S)-2-methyl-1-butyl[4-[2-(2-allyloxy-ethoxy)ethoxy]biphenyl-4'-carbonyloxy]benzoate]siloxane] (P-11)
Poly[methyl[4-(S)-2-methyl-1-butyl[4-[2-[2-(2-allyloxy-ethoxy)ethoxy]ethoxy]biphenyl-4'-carbonyloxy]benzoate]siloxane (P-12)

The monomers I-35 to I-37 were used to prepare polymers P-10 to P-12. 1.15 equivalent moles of monomer I-35 (Example 10), I-36 (Example 11) or I-37(Example 12) and polymethylhydrogensiloxane were dissolved in an suitable amount of toluene. The reactions were carried out at about 110° C. in the presence of platinum divinyltetramethyldisiloxane complex catalyst. FT-IR analysis was run to detect the absorption peak of Si—H bond (2180 cm$^{-1}$) of the reaction mixture. The hydrosilation reaction was complete when the Si—H absorption peak disappeared. The polymers were separated and purified by several reprecipitations from a tetrahydrofuran solution into methanol. The purified polymers were further subjected to preparative GPC or thin layer chromatography (TLC) to detect whether the purified polymers were free of any residual monomers or oligomers. The reprecipitation was repeated until the GPC or TLC showed no residual monomers or oligomers existing in the purified polymers.

Figure 19:
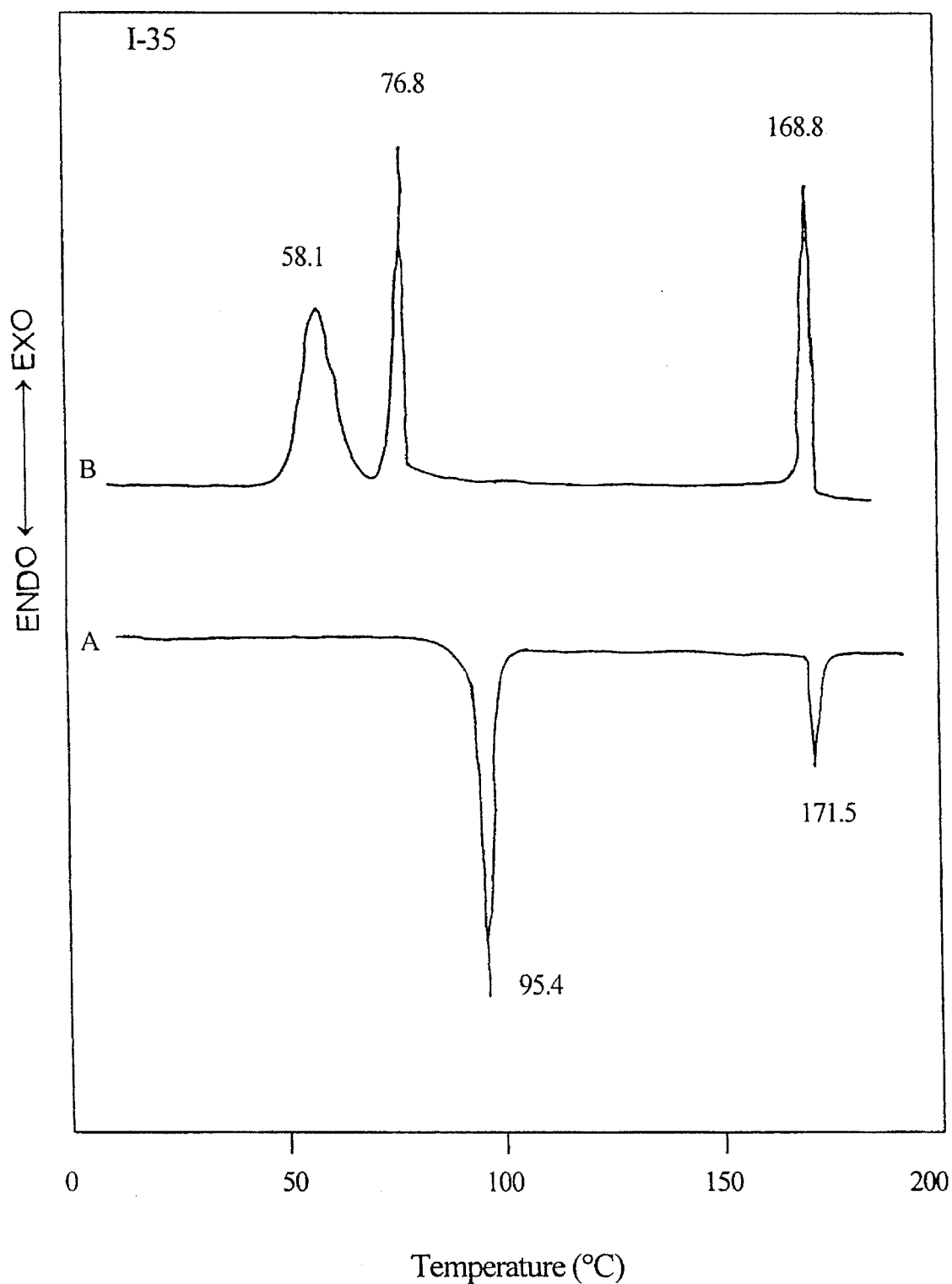
FIG. 19 is a Differential Scanning Calorimeter (DSC) thermogram (10° C./min) for monomer I-35: A) heating scan; B) cooling scan.
Figure 20:
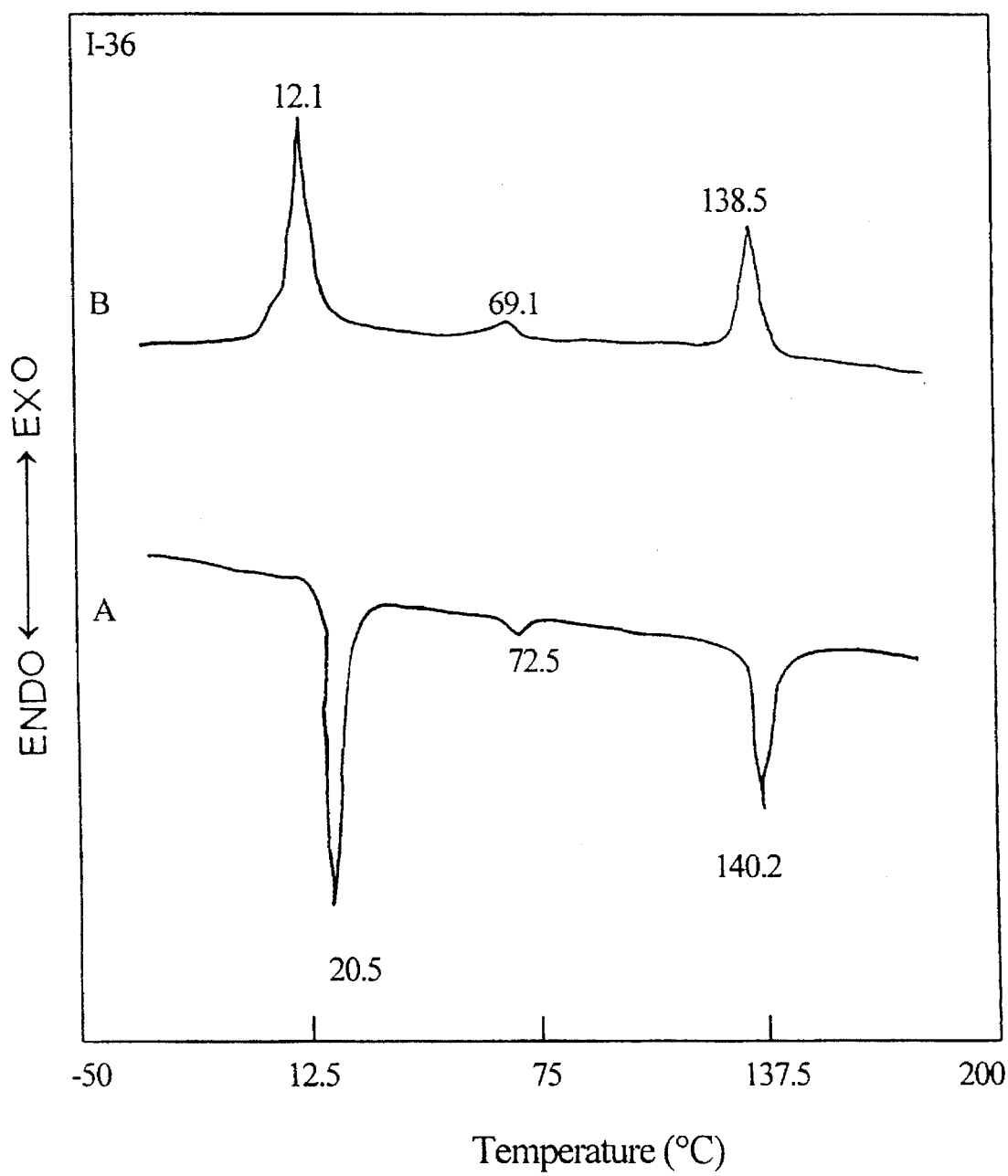
FIG. 20 is a Differential Scanning Calorimeter (DSC) thermogram (10° C./min) for monomer I-36: A) heating scan; B) cooling scan.
Figure 21:
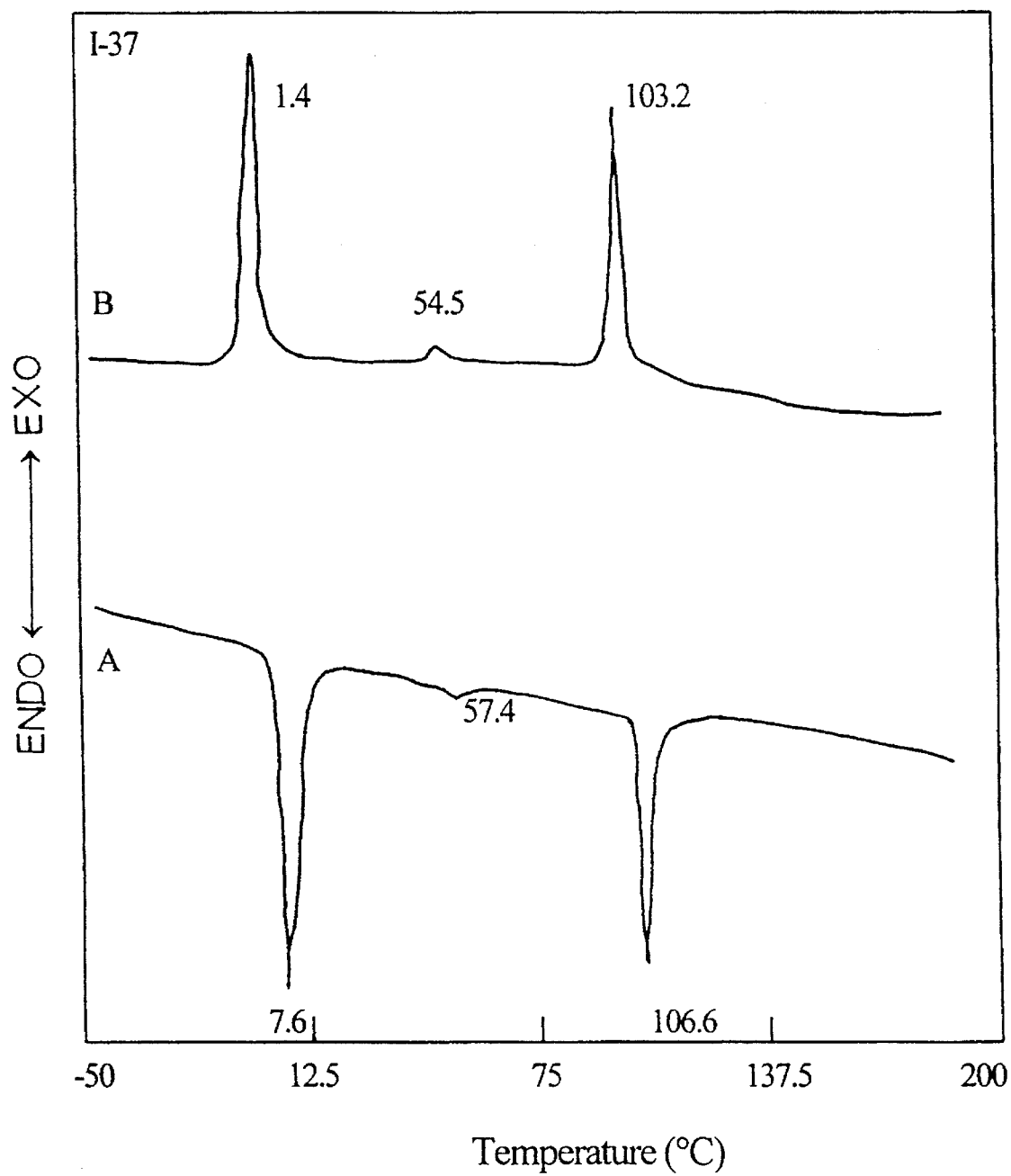
FIG. 21 is a Differential Scanning Calorimeter (DSC) thermogram (10° C./min) for monomer I-37: A) heating scan; B) cooling scan.

Table 9 summarizes the thermal transitions and corresponding enthalpy changes of monomers I-35 to I-37. These monomers have one phenylene and one biphenylene groups, and this type of aromatic ring arrangement is favorable to the formation of chiral smectic C phase. Prior to the present invention, this type of liquid crystalline monomers exhibit the liquid crystalline phases at relatively high temperatures (above 60° C.). In the present monomers I-35 to I-37, a more flexible oligooxyethylene is used as the spacer instead of the conventional alkylene. As can be seen from the data listed in Table 9, the isotropization temperature, melting temperature, and the chiral smectic A to smectic C phase transition temperature decrease by increasing the length of the oligooxyethylene spacer. The temperature range of the chiral smectic C phase is about 50° C. for each monomer of I-35 to I-37, wherein monomers I-36 and I-37 exhibit chiral smectic C phase at a temperature within the range of room temperature. The transitions from smectic A to smectic C phase of the monomers I-35 to I-37 are all observed by the optical polarizing microscopy. However, the DSC traces thereof only show the transitions from smectic A to smectic C phase of the monomers I-36 to I-37, and the enthalpy changes thereof are relatively small (about 0.03 Kcal/mol). The DSC heating and cooling traces of monomers I-35 to I-37 are shown in FIGS. 19 to 21 respectively. The optical polarizing micrographs of monomers I-35 to I-37 are shown in FIGS. 44(A) to 46(B). Among them monomer I-37 exhibits a complete dark homeotropi texture in the optical polarizing microscopy when the temperature is reduced from the isotropization temperature (103.2° C.) thereof, which is another typical characteristic pertaining to smectic A phase. The optical polarizing micrographs of monomer I-37 taken at a further cooling temperature, 34° C., display a schlieren texture of chiral smectic C phase [FIG. 46(A)] and special parallel streaks in some areas [FIG. 46(B)]. In conclusion, a longer oligooxyethylene spacer can effectively reduce the temperature at which the monomers having one phenylene and one biphenylene groups exhibit chiral smectic C phase to room temperature or even lower.

TABLE 9

Phase Transitions and Phase Transition Enthalpies for Monomers I-35–I-37

| Monomer | n | Phase transitions, °C. (corresponding enthalpy changes, Kcal/mol$^b$) |
|---|---|---|
| | | Heating |
| | | Cooling |
| I-35 | 1 | K 95.4 (5.36) S$_A$ 171.5 (1.16) I |
| | | I 168.8 (1.16) S$_A$ 76.8 (—) S$_c$* 58.1 (1.48) K |
| I-36 | 2 | K 20.5 (0.99) S$_c$* 72.5 (0.03) S$_A$ 140.2 (0.82) I |
| | | I 138.5 (0.76) SA 69.1 (0.03) S$_c$* 12.1 (0.98) K |
| I-37 | 3 | K 7.6 (0.93) S$_c$* 57.4 (0.03) S$_A$ 106.6 (0.73) I |
| | | I 103.2 (0.75) S$_A$ 54.5 (0.01) S$_c$* 1.4 (0.80) K |

$^b$K = crystalline, S$_A$ = smectic A, S$_c$* = chiral smectic C, N* = chiral nematic, I = isotropic.

Figure 22:
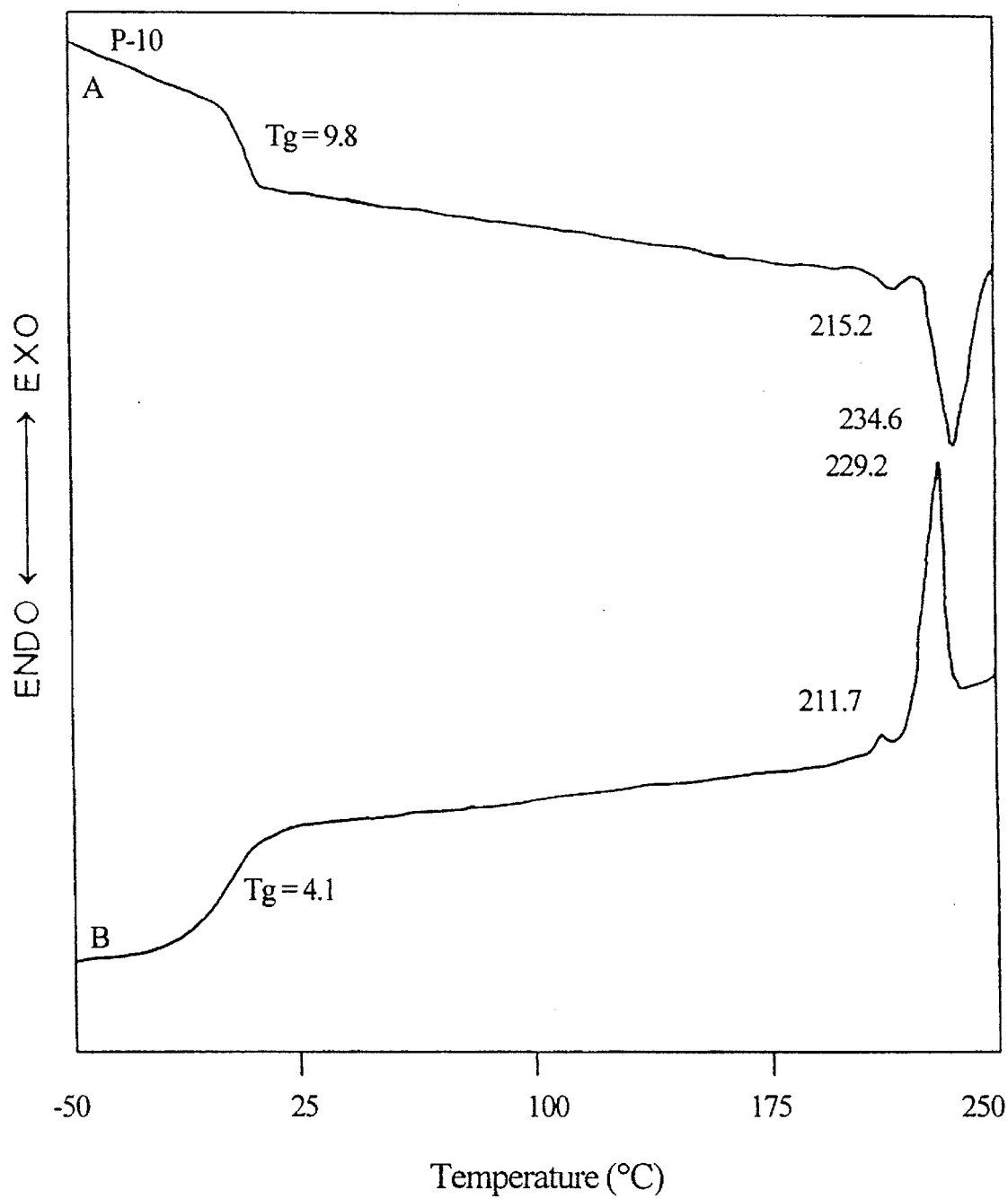
FIG. 22 is a Differential Scanning Calorimeter (DSC) thermogram (10° C./min) for polymer P-10: A) heating scan; B) cooling scan.
Figure 23:
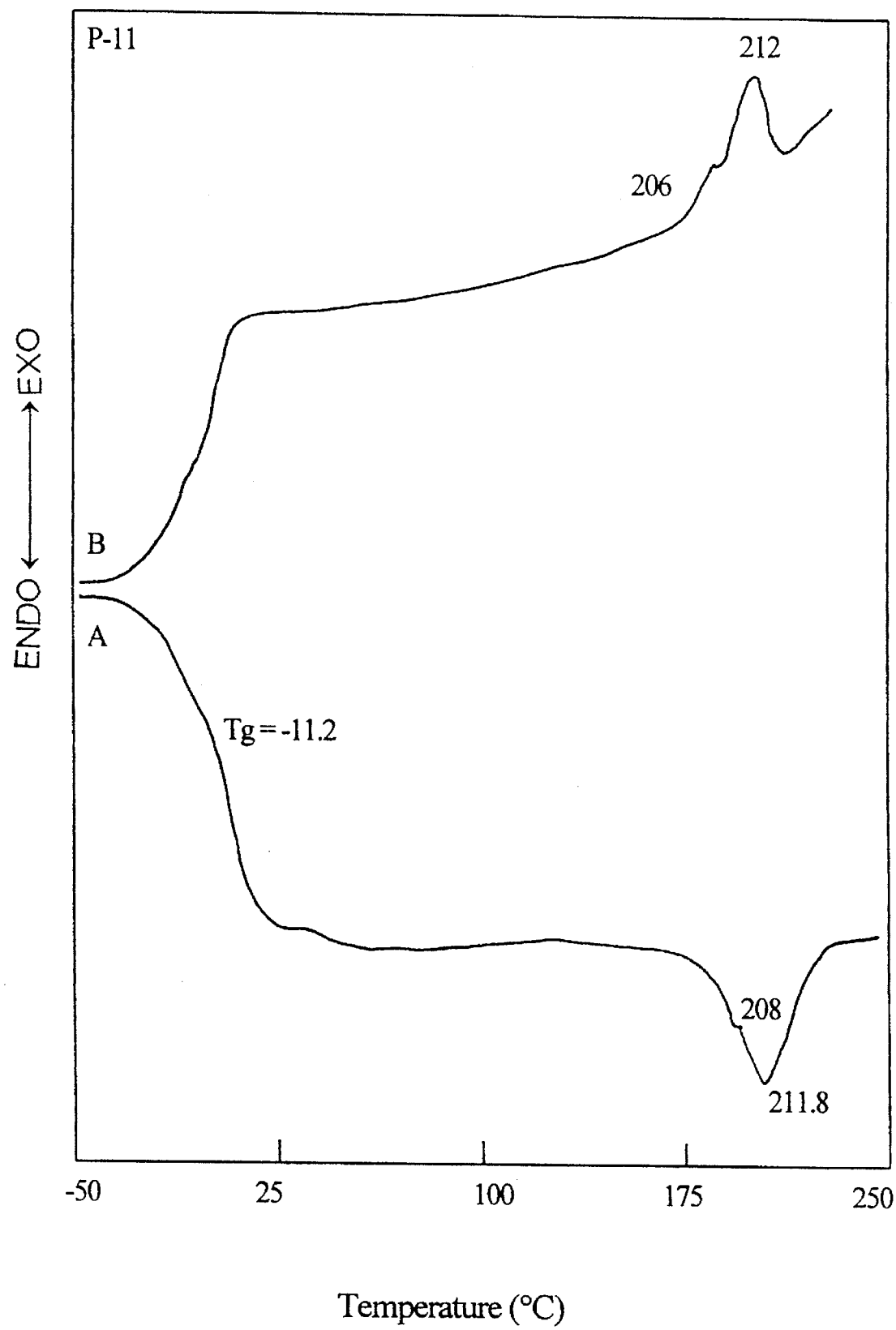
FIG. 23 is a Differential Scanning Calorimeter (DSC) thermogram (10° C./min) for polymer P-11: A) heating scan; B) cooling scan.
Figure 24:
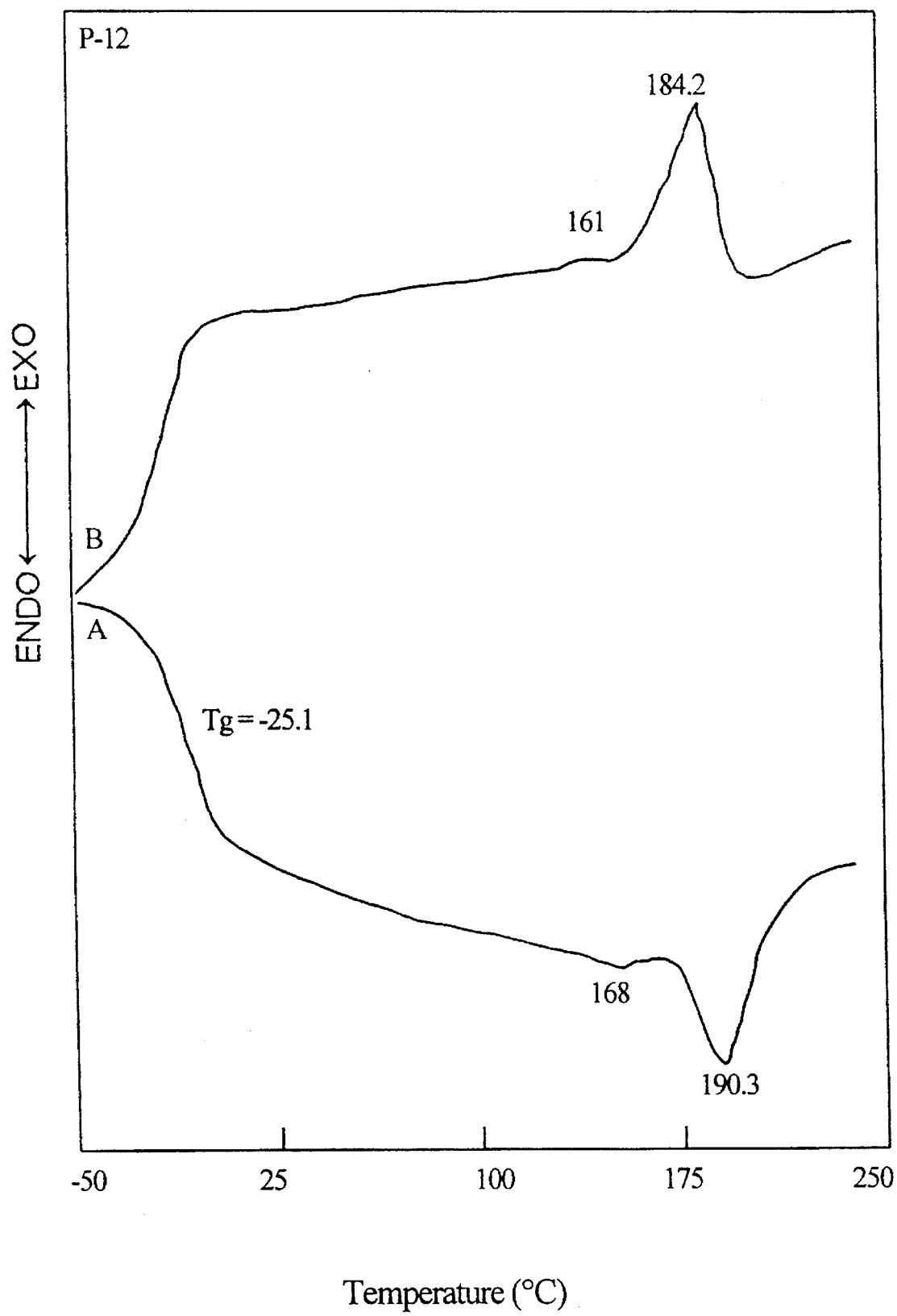
FIG. 24 is a Differential Scanning Calorimeter (DSC) thermogram (10° C./min) for polymer P-12: A) heating scan; B) cooling scan.

Table 10 summarizes the thermal transitions and corresponding enthalpy changes of polymers P-10 to P-12. Compared to the corresponding monomers, these three polymers have a broader temperature range of liquid crystalline phase. As can be seen from the data listed in Table 10, the glass transition temperature (Tg) and isotropization temperature decrease by increasing the length of the oligooxyethylene spacer. These three polymers have relatively low Tg's, because the polymer backbones and the spacers thereof are substantially very flexible. The Tg of polymer P-12 is even as low as −25° C. The mesophases of these three polymers can be maintained to a temperature which is relatively low due to the low Tg's thereof. FIGS. 22–24 present the DSC heating and cooling traces of polymers P-10 to P-12 respectively. The optical polarizing micrographs of polymers P-10 to P-12 are shown in FIGS. 47(A) to 49(B). In optical polarizing microscopy, all these three polymers exhibit a texture of fine broken pieces. However, they exhibit focal conic fan textures of smectic A phase in some areas when the cooling rate thereof is reduced. In addition, broken fan texture, color change, dots and streaks can also be observed in the optical polarizing micrographs of these three polymers. Except that polymer P-10 exhibits a relatively small phase transition at about 215° C., polymers P-11 and P-12 show no sign of phase transition in the DSC plot.

TABLE 10

| Polymers | n | Phase Transitions and Phase Transition Enthalpies for Polymers P-10–P-12 Phase transitions, °C. (corresponding enthalpy changes, Kcal/mru[b]) Heating Cooling |
|---|---|---|
| P-10 | 1 | G 9.8 S$_c$* 215.2 (0.07) S$_A$ 234.6 (0.80 I |
| | | I 229.2 (0.73) S$_A$ 211.7 (0.03) S$_c$* 4.1 G |
| P-11 | 2 | G −11.2 S$_c$* 208 (—) S$_A$ 211.8 (0.85) I |
| | | I 212.0 (0.49) S$_A$ 206 (—) S$_c$* −15.0 G |
| P-12 | 3 | G −25.1 S$_c$* 168 (—) S$_A$ 190.3 (0.94) I |
| | | I 184.2 (0.98) S$_A$ 161 (—) S$_c$* −20.8 G |

[b]mru = mole repeating unit; G = Glassy, S$_A$ = smectic A, S$_c$* = chiral smectic C, I = isotropic.

Figure 25:
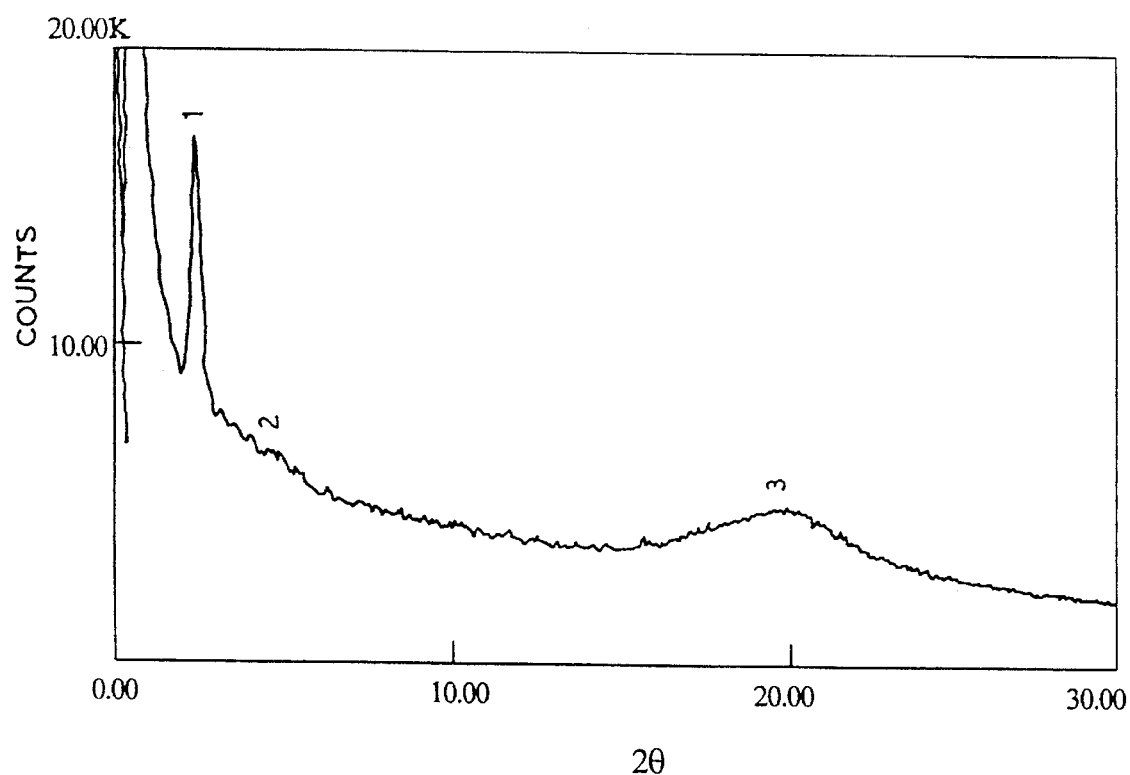
FIG. 25 is an X-ray diffraction diagram of polymer P-11.
Figure 26:
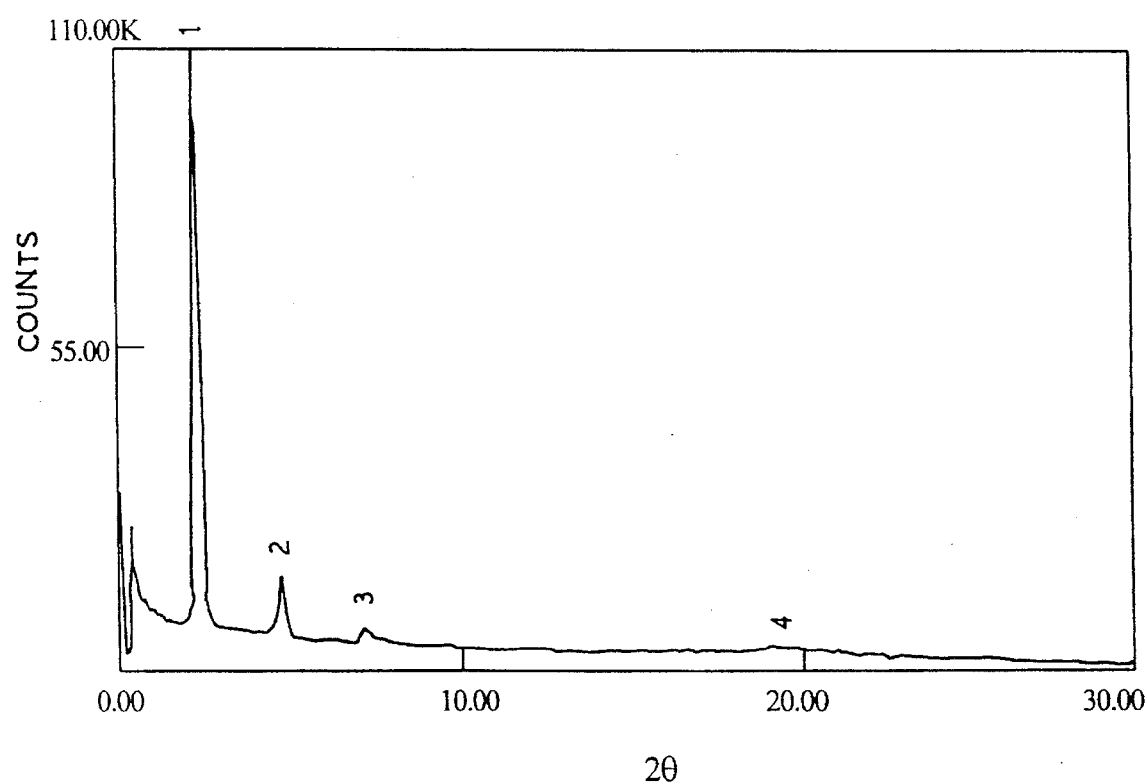
FIG. 26 is an X-ray diffraction diagram of polymer P-12.

In order to prove the existence of chiral smectic C phase, X-ray diffraction measurements were run for polymers P-11 and P-12. A polymer specimen was placed between two Mylar films, and a stress was applied to the Mylar films to give the polymer an orientation. The X-ray diffraction measurements were taken at different temperatures from 70°–160° C. FIG. 25 is an X-ray diffraction diagram of polymer P-11 at one temperature. In accordance with the Bragg's equation, $2d\sin\theta = n\lambda$, one can calculate the smectic layer spacing, ds1, from the low diffraction angle, and the lateral spacing, d1, from the outer ring diffraction of high angle. In addition, one can calculate the tilt angle of side chain from a formula: $ds1 = L\cos\theta$, wherein L is the calculated length of fully extended side chain. Table 11 summarizes the X-ray measurements of polymer P-11 at different temperatures. The data of Table 11 show that the layer spacing of polymer P-11 decreases with decreasing the measuring temperature, and the tilt angle of the side chains thereof increases with decreasing the measuring temperature. FIG. 26 is an X-ray diffraction diagram of polymer P-12 at one temperature. It can be seen from FIG. 26 that there are three extremely large diffraction holes in the low angles and there are two diffraction crescents in the high angles, which indicates that the polymer molecules are arranged in a substantially regular layered structure. Table 12 summarizes the X-ray measurements of polymer P-12 at different temperatures. The data of Table 12 show that the layer spacing of polymer P-12 decreases with decreasing the measuring temperature, and the tilt angle of the side chains thereof measured at 160° C. is greater than zero and increases with decreasing the measuring temperature. Moreover, the lateral spacings of the mesogens of both polymer P-11 and P-12 are close to 5 and decrease with decreasing the measuring temperature. Polymers P-11 and P-12 are identified as ferroelectric liquid crystalline polymers having chiral smectic C phase by comparing the above X-ray diffraction analysis results with the X-ray diffraction analysis results of ferroelectric liquid crystalline polymers found in the literature.

TABLE 11

Temperature dependent X-ray measurements of polymer P-11

| T/°C. | dsl/Å | dl/Å | tilt angle/° |
|---|---|---|---|
| 160 | 37.72 | 4.81 | 0 |
| 130 | 37.70 | 4.71 | 0 |
| 100 | 36.78 | 4.62 | 13 |
| 70 | 35.45 | 4.51 | 20 |

Calculated length of fully extended side chain: 37.78Å
dsl: Smectic layer spacing
dl: lateral spacing of the mesogens

TABLE 12

Temperature dependent X-ray measurements of polymer P-12

| T/°C. | dsl/Å | dl/Å | tilt angle/° |
|---|---|---|---|
| 160 | 38.05 | 4.84 | 22 |
| 130 | 38.05 | 4.75 | 22 |
| 100 | 36.78 | 4.62 | 27 |
| 70 | 36.78 | 4.57 | 27 |

Calculated length of fully extended side chain: 41.15Å
dsl and dl are defined same as in Table 11.

What is claimed is:

1. A liquid crystalline polymer having the following formula:

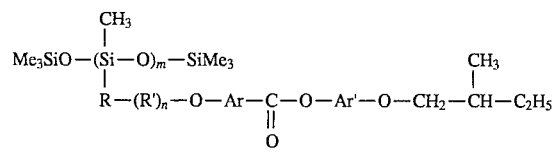

wherein Me is methyl;

m is an integer of about 40–80;

n is an integer of about 1–9;

R is ethylene or trimethylene;

R' is methylene;

Ar is

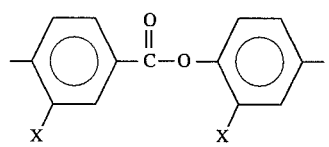

wherein x is chlorine or hydrogen; and

Ar' is phenylene or phenylenecarbonyl.
2. A liquid crystalline compound having the following formula:
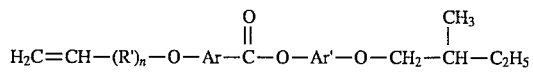
wherein n is an integer of about 1–12;
R' is oxyethylene;
Ar is
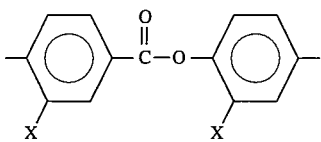
wherein x is chlorine or hydrogen; and
Ar' is phenylene or phenylenecarbonyl.
* * * * *

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Col. 1, line 33, delete "Crys.." and insert therefore -- Crys. --.

Col. 1, line 41, delete ".S. Esselin" and insert therefore -- S. Esselin --.

Col. 5, line 24, delete "Chiral smectic C" and insert therefore -- chiral smectic C --.

Col. 6, line 44, delete "sent multiplier" and insert therefore -- sent multiplet --.

Col. 7, line 43, following "(s;3H, C$\underline{H}_3$-Ph-)" delete "0".

Col. 9, line 40, delete "-C$\underline{H}$=C$\underline{H}_2$)" and insert therefore -- -C$\underline{H}$=C$\underline{H}_2$) --.

Col. 10, line 2, delete "-C$\underline{H}$=C$\underline{H}_2$)" and insert therefore -- -C$\underline{H}$=C$\underline{H}_2$) --.

Cols. 9 and 10, in Table 1, line 1 following the headings, delete "0.88 (t, 3H, -CH$_2$-CH$_3$), 0.96 [(d, 3H, -CH(CH$_3$)-], 1.21-1.52 (m, 2H," and insert therefore -- 0.88 (t, 3H, -CH$_2$-CH$_3$), 0.96 [(d, 3H, -CH(CH$_3$)-], 1.21-1.52 (m, 2H, --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Cols. 9 and 10, in Table 1, line 2 following the headings, delete "-$CH_2$-$CH_3$), 1.86 [m, 1 H, -CH($CH_3$)-], 3.72 [m, 2H, -$OCH_2$-" and insert therefore -- -$CH_2$-$CH_3$), 1.86 [m, 1H, -C$\underline{H}$($CH_3$)-], 3.72 [m, 2H, -O$CH_2$- --.

Cols. 9 and 10, in Table 1, line 3 following the headings, delete "CH($CH_3$)-], 4.54 (d, 2H, -$CH_2$-0Ph), 5.03 (m, 2H. $CH_2$=), 5,80" and insert therefore -- CH($CH_3$)-], 4.54 (d, 2H, -$CH_2$-0Ph), 5.03 (m, 2H, $CH_2$=), 5.80 --.

Cols. 9 and 10, in Table 1, line 4 following the headings, delete "(m, 1 H, =CH-), 6.86-8.17 (m, 12H aromatic protons)" and insert therefore -- (m, 1H, =C$\underline{H}$-), 6.86-8.17 (m, 12H aromatic protons) --.

Cols. 9 and 10, in Table 1, line 5 following the headings, delete "0.88 (t. 3H, -$CH_2$-$CH_3$), 0.96 [t, 3H, -CH($CH_3$)-], 1.19-1.53" and insert therefore -- 0.88 (t, 3H, -$CH_2$-$CH_3$), 0.96 [t, 3H, -CH($CH_3$)-], 1.19 - 1.53 --.

Cols. 9 and 10, in Table 1, line 6 following the headings, delete "(m, 2H, -$CH_2$-$CH_3$), 1.80 [m, 1H, -CH($CH_3$)-]," and insert therefore -- (m, 2H, -$CH_2$-$CH_3$), 1.80 [m, 1H, -C$\underline{H}$($CH_3$)-], --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Cols. 9 and 10, in Table 1, line 7 following the headings, delete "2.52 (m, 2H, -$CH_2$-CH=), 3.73[m, 2H," and insert therefore -- 2.52 (m, 2H, -$C\underline{H}_2$-CH=), 3.73[m, 2H, --.

Cols. 9 and 10, in Table 1, line 8 following the headings, delete "-$OCH_2$-CH($CH_3$)-], 4.01 (t, 2H, -$CH_2$-OPh), 5.10 (m, 2H, CH@m), 5.88 (m," and insert therefore -- -$OC\underline{H}_2$-CH($CH_3$)-], 4.01 (t, 2H, -$CH_2$-OPh), 5.10 (m, 2H, $C\underline{H}_2$=), 5.88 (m, --.

Cols. 9 and 10, in Table 1, line 9 following the headings, delete "1H, =CH-), 6.86-8.17 (m, 12H aromatic protons)" and insert therefore -- 1H, =$C\underline{H}$-), 6.86 - 8.17 (m, 12H aromatic protons) --.

Cols. 9 and 10, in Table 1, line 10 following the headings, delete "0.88 (t, 3H, -$CH_2$-$CH_3$), 0.96 [t, 3H, -CH(CH-3)-], 1.17-1.89 [m, 5H, -$CH_2$-" and insert therefore -- 0.88 (t, 3H, -$CH_2$-$C\underline{H}_3$), 0.96 [t, 3H, -CH($C\underline{H}_3$)-], 1.17-1.89 [m, 5H, -$C\underline{H}_2$- --.

Cols. 9 and 10, in Table 1, line 11 following the headings, delete "and -CH($CH_3$)-$CH_2$-], 2.20(m, 2H, -$CH_2$-CH=), 3.72 [m, 2H, -$OCH_2$-" and insert therefore -- and -$C\underline{H}$($CH_3$)-$CH_2$-], 2.20(m, 2H, -$C\underline{H}_2$-CH=), 3.72 [m, 2H, -$OC\underline{H}_2$- --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Cols. 9 and 10, in Table 1, line 12 following the headings, delete "CH(CH$_3$)-], 3.97 (t, 2H, -CH$_2$-OPh), 4.99 (m, 2H, CH$_2$=), 5.81 (m, 1H," and insert therefore -- CH(CH$_3$)-], 3.97 (t, 2H, -CH$_2$-OPh), 4.99 (m, 2H, C$\underline{H}$$_2$=), 5.81 (m, 1H, --.

Cols. 9 and 10, in Table 1, line 13 following the headings, delete "=CH-), 6.86-8.17 (m, 12H aromatic protons)" and insert therefore -- =C$\underline{H}$-), 6.86-8.17 (m, 12H aromatic protons) --.

Cols. 9 and 10, in Table 1, line 14 following the headings, delete "0.88 (t, 3H, -CH$_2$-CH$_3$), 0.95 [(d, 3H, -CH(CH$_3$)-], 1.14-1.81 [m, 7H," and insert therefore -- 0.88 (t, 3H, -CH$_2$-C$\underline{H}$$_3$), 0.95 [(d, 3H, -CH(C$\underline{H}$$_3$)-], 1.14 - 1.81 [m, 7H, --.

Cols. 9 and 10, in Table 1, line 15 following the headings, delete "-(CH$_2$)$_2$- and -CH(CH$_3$)-CH$_2$-], 2.07 (m, 2H, -CH$_2$-CH=)," and substitute therefore -- -(C$\underline{H}$$_2$)$_2$- and -C$\underline{H}$(CH$_3$)-CH$_2$-], 2.07 (m, 2H, -C$\underline{H}$$_2$-CH=), --.

Cols. 9 and 10, in Table 1, line 17 following the headings, delete "(t, 2H, -CH$_2$-OPh), 5.10 (m, 2H, CH$_2$=), 5.86 (m," and insert therefore -- (t, 2H, -C$\underline{H}$$_2$-OPh), 5.10 (m, 2H, C$\underline{H}$$_2$=), 5.86 (m, --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Cols. 11 and 12, in Table 1, line 1 following the headings, delete "1H, =CH-), 6.86-8.16 (m, 12H aromatic protons)" and insert therefore -- 1H, =C$\underline{H}$-), 6.86-8.16 (m, 12H aromatic protons) --.

Cols. 11 and 12, in Table 1, line 2 following the headings, delete "0.86 (t, 3H, -CH$_2$-CH$_3$), 0.94 [(d, 3H, -CH(CH$_3$)-], 1.18-1.80 [m, 17H," and insert therefore -- 0.86 (t, 3H, -CH$_2$-C$\underline{H}_3$), 0.94 [(d, 3H, -CH(C$\underline{H}_3$)-], 1.18 - 1.80 [m, 17H, --.

Cols. 11 and 12, in Table 1, line 3 following the headings, delete "-(CH$_2$)$_7$- and -CH(CH$_3$)-CH$_2$-], 2.03 (m, 2H, -CH$_2$-CH=), 3.91 [m, 2H," and insert therefore -- -(CH$_2$)$_7$- and -C$\underline{H}$(CH$_3$)-C$\underline{H}_2$-], 2.03 (m, 2H, -C$\underline{H}_2$-CH=), 3.91 [m, 2H, --.

Cols. 11 and 12, in Table 1, line 4 following the headings, delete "-OCH$_2$-CH(CH$_3$)-], 4.11 (m, 2H, -CH$_2$-OPh), 4.90 (m, 2H, CH$_2$=), 5.76" and insert therefore -- -OC$\underline{H}_2$-CH(CH$_3$)-], 4.11 (m, 2H, -C$\underline{H}_2$-OPh), 4.90 (m, 2H, C$\underline{H}_2$=), 5.76 --.

Col. 12, line 28, following "C$\underline{H}$-" insert -- and two -C$\underline{H}_3$) --.

Col. 12, line 28, delete "(s; 1H, -OH)" and insert therefore -- (s; 1H, -O$\underline{H}$) --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Col. 12, line 29, delete "and two-$CH_3$)".

Col. 12, line 31, following "$CH$-" insert
-- and two -$CH_3$) --.

Col. 12, line 32, delete "and two-$CH_3$)".

Cols. 11 and 12, in Table 2, line 1 following the headings, delete "1.99-0.76 (m, 25H, -$CH_2$-$CH_2$-$CH_2$, -CH- and -$CH_3$)," and insert therefore -- 1.99-0.76 (m; 25H, -$CH_2$-$CH_2$-$CH_2$, -$CH$- and -$CH_3$), --.

Cols. 11 and 12, in Table 2, line 2 following the headings, delete "3.76-3.68 (m; 2H, -O-$CH_2$-$CHCH_3$-)," and insert therefore -- 3.76-3.68 (m; 2H, -$CH_2$-$CHCH_3$-), --.

Cols. 11 and 12, in Table 2, line 3 following the headings, delete "4.00-3.97 (t, 2H, -O-$CH_2$-$CH_2$-) 4.96-4.86 [q, 2H, $H_2C=CH$-)," and insert therefore -- 4.00-3.97 (t, 2H, -O-$CH_2$-$CH_2$-) 4.96-4.86 [q, 2H, $H_2C=CH$-), --.

Cols. 11 and 12, in Table 2, line 4 following the headings, delete "5.82-5.73 (m, 1H, $H_2C=CH$-), 8.21-6.86 (m, 12H aromatic protons)" and insert therefore -- 5.82-5.73 (m, 1H, $H_2C=CH$-), 8.21-6.86 (m, 12H aromatic protons) --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Col. 12, line 29, delete "and two-C$\underline{H}_3$)".

Cols. 11 and 12, in Table 2, line 5 following the headings, delete "2.00-0.76 (m; 25H, -CH$_2$-CH$_2$CH$_2$, -CH- and -CH$_3$)," and insert therefore -- 2.00-0.76 ($\underline{m}$; 25H, -CH$_2$-C$\underline{H}_2$-CH$_2$, -C$\underline{H}$- and -C$\underline{H}_3$), --.

Cols. 11 and 12, in Table 2, line 6 following the headings, delete "3.78-3.67 (m; 2H, -O-CH$_2$-CHCH$_3$-), 4.01-3.97 (t, 2H, -O-CH$_2$-CH$_2$-)" and insert therefore -- 3.78-3.67 (m; 2H, -O-C$\underline{H}_2$-CHCH$_3$-), 4.01-3.97 (t, 2H, -O-C$\underline{H}_2$-CH$_2$-) --.

Cols. 11 and 12, in Table 2, line 7 following the headings, delete "4.96-4.86 [q, 2H, H$_2$C=CH-)," and insert therefore -- 4.96-4.86 [q, 2H, $\underline{H}_2$C=CH-), --.

Cols. 13 and 14, in Table 2, line 1 following the headings, delete "5.82-5.68 (m, 1H, H$_2$C=CH-), 8.28-6.86 (m, 11H aromatic protons)" and insert therefore -- 5.82-5.68 (m, 1H, H$_2$C=C$\underline{H}$-), 8.28-6.86 (m, 11H aromatic protons) --.

Cols. 13 and 14, in Table 2, line 2 following the headings, delete "2.01-0.76 (m; 25H, -CH$_2$-CH$_2$-CH$_2$, -CH- and -CH$_3$), 3.78-3.66" and insert therefore -- 2.01-0.76 (m; 25H, -CH$_2$-C$\underline{H}_2$-CH$_2$, -C$\underline{H}$- and -C$\underline{H}_3$), 3.78-3.66 --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Cols. 13 and 14, in Table 2, line 3 following the headings, delete "(m; 2H, -O-CH$_2$-CHCH$_3$-), 4.08-4.05 (t, 2H, -O-CH$_2$-CH$_2$-) 4.95-4.86" and insert therefore -- (m; 2H, -O-C$\underline{H}$$_2$-CHCH$_3$-), 4.08-4.05 (t, 2H, -O-C$\underline{H}$$_2$-CH$_2$-) 4.95-4.86 --.

Cols. 13 and 14, in Table 2, line 4 following the headings, delete "[q, 2H, H$_2$C=CH-), 5.82-5,69 (m, 1H, H$_2$C=CH-), 8.21-6.86 (m, 11H aromatic protons)" and insert therefore -- [q, 2H, $\underline{H}$$_2$C=CH-), 5.82-5.69 (m, 1H, H$_2$C=C$\underline{H}$-), 8.21-6.86 (m, 11H aromatic protons) --.

Cols. 13 and 14, in Table 2, line 5 following the headings, delete "1.99-0.73 (m; 25H, -CH$_2$-CH$_2$-CH$_2$, -CH- and -CH$_3$), 3.78-3.65" and insert therefore -- 1.99-0.73 (m; 25H, -CH$_2$-CH$_2$-CH$_2$, -C$\underline{H}$- and -C$\underline{H}$$_3$), 3.78-3.65 --.

Cols. 13 and 14, in Table 2, line 6 following the headings, delete "(m; 2H, -O-CH$_2$-CHCH$_3$-), 4.08-4.05 (t, 2H, -O-CH$_2$-CH$_2$-) 4.96-4.86" and insert therefore -- (m; 2H, -O-C$\underline{H}$$_2$-CHCH$_3$-), 4.08 - 4.05 (t, 2H, -O-C$\underline{H}$$_2$-CH$_2$-) 4.96-4.86 --.

Cols. 13 and 14, in Table 2, line 7 following the headings, delete "[q, 2H, H$_2$C=CH-), 5.81-5.69 (m, 1H, H$_2$C=CH-), 8.28-6.85 (m, 10H aromatic protons)" and insert therefore -- [q, 2H, $\underline{H}$$_2$C=CH-), 5.81 - 5.69 (m, 1H, H$_2$C=C$\underline{H}$-), 8.28-6.85 (m, 10H aromatic protons) --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Col. 17, in Table 5, line 3 following the headings, delete "g 18 $S_A$ 94(0.73) I" and insert therefore -- g 18 $S_A$ 84(0.78) I --.

Col. 17, in Table 5, line 5 following the headings, delete "g 22 $S_B$ 99(0.39)$S_A$212(0.86) I" and insert therefore -- g 22 $S_B$ 99(0.89)$S_A$212(0.86) I --.

Col. 17, in Table 5, line 9 following the headings, delete "g 20 $S_B$ 109(0.73) $S_c$* 143 (-)$^c$ $S_A$ 218(0.36) I" and insert therefore -- g 20 $S_B$ 109(0.78) $S_c$* 143 (-)$^c$ $S_A$ 218(0.86) I --.

Col. 17, following Table 5, insert the following

"mru = mole repeating unit
Enthalpy is very small."

Col. 18, line 51, delete "crystal line" and insert therefore -- crystalline --.

Col. 20, line 66, delete "CH" and insert therefore -- C$\underline{H}$ --.

UNITED STATES PATENT AND TRADEMARK OFFICE
CERTIFICATE OF CORRECTION

PATENT NO. : 5,563,230
DATED : October 8, 1996
INVENTOR(S) : Hsu et al.

It is certified that error appears in the above-indentified patent and that said Letters Patent is hereby corrected as shown below:

Col. 21, line 8, delete "$\underline{H}_2$)" and insert therefore -- $\underline{H}_2$-) --.

Col. 21, line 34, delete "(m, 1H, $H_2C=CH-$)" and insert therefore -- (m, 1H, $H_2C=C\underline{H}-$) --.

Cols. 21 and 22, in Table 8, line 3 following the headings, delete "185" and insert therefore -- 1.85 --.

Col. 25, in Table 10, line 1 following the headings, delete "(0.80 I" and insert therefore -- (0.80) I --.

Col. 26, line 11, delete "close to 5" and insert therefore -- close to 5Å --.

Signed and Sealed this

Eighth Day of July, 1997

Attest:

*Attesting Officer*

BRUCE LEHMAN
*Commissioner of Patents and Trademarks*